US012239333B2

(12) United States Patent
Quick et al.

(10) Patent No.: US 12,239,333 B2
(45) Date of Patent: Mar. 4, 2025

(54) SINGLE INSERTION DELIVERY SYSTEM FOR TREATING EMBOLISM AND ASSOCIATED SYSTEMS AND METHODS

(71) Applicant: Inari Medical, Inc., Irvine, CA (US)

(72) Inventors: Richard Quick, Mission Viejo, CA (US); Benjamin Edward Merritt, San Clemente, CA (US); John Coleman Thress, Capistrano Beach, CA (US); Paul Lubock, Monarch Beach, CA (US); Thomas M. Tu, Louisville, KY (US)

(73) Assignee: Inari Medical, Inc., Irvine, CA (US)

( * ) Notice: Subject to any disclaimer, the term of this patent is extended or adjusted under 35 U.S.C. 154(b) by 0 days.

(21) Appl. No.: 18/497,249

(22) Filed: Oct. 30, 2023

(65) Prior Publication Data

US 2024/0074771 A1    Mar. 7, 2024

Related U.S. Application Data

(63) Continuation of application No. 17/865,307, filed on Jul. 14, 2022, now Pat. No. 11,849,963, which is a
(Continued)

(51) Int. Cl.
*A61B 17/22* (2006.01)
*A61B 17/221* (2006.01)
(Continued)

(52) U.S. Cl.
CPC ........ *A61B 17/22031* (2013.01); *A61B 17/22* (2013.01); *A61B 17/221* (2013.01);
(Continued)

(58) Field of Classification Search
CPC .... A61M 1/60; A61M 1/0001; A61M 1/0003; A61M 1/0281; A61M 39/0613;
(Continued)

(56) References Cited

U.S. PATENT DOCUMENTS 1,101,890 A    6/1914    Tunstead
2,502,639 A    2/1948    Blake
(Continued)

FOREIGN PATENT DOCUMENTS

AU    2015210338    8/2015
CN    102186427    9/2011
(Continued)

OTHER PUBLICATIONS

US 12,114,876 B2, 10/2024, Quick et al. (withdrawn)
(Continued)

*Primary Examiner* — Tuan V Nguyen
(74) *Attorney, Agent, or Firm* — Perkins Coie LLP

(57) ABSTRACT

Systems and methods for the intravascular treatment of clot material within a blood vessel of a human patient are disclosed herein. A method in accordance with embodiments of the present technology can include, for example, engaging an interventional device of a catheter system with clot material in a blood vessel and withdrawing the interventional device and the portion of the clot material through a guide catheter. In some embodiments, the catheter system can include an attachment/valve member coupled to a proximal portion of the guide catheter, and the method can include unsealing the attachment/valve member to facilitate withdrawing the interventional device through the attachment/valve member without significant retention of clot material within the attachment/valve member. The method can further include resealing and aspirating the guide catheter before advancing another interventional device to the clot material to again engage and remove clot material from the blood vessel.

28 Claims, 20 Drawing Sheets

Related U.S. Application Data continuation of application No. 17/498,642, filed on Oct. 11, 2021, now Pat. No. 12,016,580, which is a continuation of application No. 16/258,344, filed on Jan. 25, 2019, now Pat. No. 11,154,314.

(60) Provisional application No. 62/622,691, filed on Jan. 26, 2018.

(51) Int. Cl.
   *A61M 25/00* (2006.01)
   *A61M 39/06* (2006.01)
   *A61B 17/00* (2006.01)

(52) U.S. Cl.
   CPC ........ *A61M 25/0082* (2013.01); *A61M 39/06* (2013.01); *A61B 2017/00907* (2013.01); *A61B 2017/22034* (2013.01); *A61B 2017/22042* (2013.01); *A61B 2017/22079* (2013.01); *A61B 2017/22094* (2013.01); *A61B 2217/005* (2013.01); *A61M 2210/12* (2013.01)

(58) Field of Classification Search
   CPC ...... A61M 2039/027; A61M 2039/062; A61M 25/0122; A61B 17/22031; A61B 2017/22035; A61B 17/22; A61B 17/221; A61B 17/220758; A61B 17/320725; A61B 17/22034; A61B 17/22042; A61B 17/22079; A61B 17/22094
   See application file for complete search history.

(56) References Cited

U.S. PATENT DOCUMENTS

| | | |
|---|---|---|
| 2,707,954 A | 5/1955 | Kas, Sr. |
| 2,784,717 A | 3/1957 | Thompson |
| 2,846,179 A | 8/1958 | Monckton |
| 2,955,592 A | 10/1960 | Maclean |
| 3,088,363 A | 5/1963 | Sparks |
| 3,197,173 A | 7/1965 | Taubenheim |
| 3,383,131 A | 5/1968 | Rosfelder |
| 3,416,531 A | 12/1968 | Edwards |
| 3,435,826 A | 4/1969 | Fogarty |
| 3,438,607 A | 4/1969 | Williams et al. |
| 3,515,137 A | 6/1970 | Santomieri |
| 3,661,144 A * | 5/1972 | Jensen .................. A61M 1/79 606/160 |
| 3,675,657 A | 7/1972 | Gauthier |
| 3,785,380 A * | 1/1974 | Brumfield ............... A61M 1/76 604/902 |
| 3,860,006 A | 1/1975 | Patel |
| 3,863,624 A * | 2/1975 | Gram ..................... A61M 1/79 604/191 |
| 3,892,161 A | 7/1975 | Sokol |
| 3,923,065 A | 12/1975 | Nozick et al. |
| 4,030,503 A | 6/1977 | Clark, III |
| 4,034,642 A | 7/1977 | Iannucci et al. |
| 4,036,232 A | 7/1977 | Genese |
| 4,187,849 A | 2/1980 | Stim |
| 4,222,380 A | 9/1980 | Terayama |
| 4,243,040 A | 1/1981 | Beecher |
| 4,287,808 A | 9/1981 | Leonard et al. |
| 4,324,262 A | 4/1982 | Hall |
| 4,393,872 A | 7/1983 | Reznik et al. |
| 4,401,107 A | 8/1983 | Harber et al. |
| 4,469,100 A | 9/1984 | Hardwick |
| 4,523,738 A | 6/1985 | Raftis et al. |
| 4,551,862 A | 11/1985 | Haber |
| 4,604,094 A | 8/1986 | Shook |
| 4,611,594 A | 9/1986 | Grayhack et al. |
| 4,634,421 A | 1/1987 | Hegemann |
| 4,643,184 A | 2/1987 | Mobin-Uddin |
| 4,646,736 A | 3/1987 | Auth et al. |
| 4,650,466 A | 3/1987 | Luther |
| 4,693,257 A | 9/1987 | Markham |
| 4,705,518 A | 11/1987 | Baker et al. |
| 4,776,337 A | 10/1988 | Palmaz |
| 4,790,812 A | 12/1988 | Hawkins, Jr. et al. |
| 4,826,483 A | 5/1989 | Molnar, IV |
| 4,863,440 A | 9/1989 | Chin et al. |
| 4,870,953 A | 10/1989 | DonMichael et al. |
| 4,880,408 A | 11/1989 | Cumes et al. |
| 4,883,458 A | 11/1989 | Shiber |
| 4,886,062 A | 12/1989 | Wiktor |
| 4,890,611 A | 1/1990 | Monfort et al. |
| 4,898,575 A | 2/1990 | Fischell et al. |
| 4,946,440 A | 8/1990 | Hall |
| 4,960,259 A | 10/1990 | Sunnanvader et al. |
| 4,978,341 A | 12/1990 | Niederhauser |
| 4,981,478 A | 1/1991 | Evard et al. |
| 5,030,201 A | 7/1991 | Palestrant |
| 5,053,008 A | 10/1991 | Bajaj |
| 5,059,178 A | 10/1991 | Ya |
| 5,100,423 A | 3/1992 | Fearnot |
| 5,127,626 A | 7/1992 | Hilal et al. |
| 5,129,910 A | 7/1992 | Phan et al. |
| 5,135,484 A | 8/1992 | Wright |
| 5,154,724 A | 10/1992 | Andrews |
| 5,158,533 A | 10/1992 | Strauss et al. |
| 5,158,564 A | 10/1992 | Schnepp-Pesch et al. |
| 5,192,274 A | 3/1993 | Bierman |
| 5,192,286 A | 3/1993 | Phan et al. |
| 5,192,290 A | 3/1993 | Hilal |
| 5,197,485 A | 3/1993 | Grooters |
| 5,234,403 A | 8/1993 | Yoda et al. |
| 5,242,461 A | 9/1993 | Kortenbach et al. |
| 5,244,619 A | 9/1993 | Burnham |
| 5,246,011 A | 9/1993 | Caillouette |
| 5,323,514 A | 6/1994 | Masuda et al. |
| 5,329,923 A | 7/1994 | Lundquist |
| 5,360,417 A | 11/1994 | Gravener et al. |
| 5,364,345 A | 11/1994 | Lowery et al. |
| 5,376,071 A | 12/1994 | Henderson |
| 5,376,101 A | 12/1994 | Green et al. |
| 5,383,887 A | 1/1995 | Nadal |
| 5,389,100 A | 2/1995 | Bacich et al. |
| 5,391,152 A | 2/1995 | Patterson et al. |
| 5,419,774 A | 5/1995 | Willard et al. |
| 5,421,824 A | 6/1995 | Clement et al. |
| 5,429,610 A | 7/1995 | Vaillancourt |
| 5,429,616 A | 7/1995 | Schaffer |
| 5,443,443 A | 8/1995 | Shiber |
| 5,456,667 A | 10/1995 | Ham et al. |
| 5,476,450 A | 12/1995 | Ruggio |
| 5,484,418 A | 1/1996 | Quiachon et al. |
| 5,490,859 A | 2/1996 | Mische et al. |
| 5,496,365 A | 3/1996 | Sgro |
| 5,527,326 A | 6/1996 | Hermann et al. |
| 5,549,626 A | 8/1996 | Miller et al. |
| 5,591,137 A | 1/1997 | Stevens |
| 5,639,276 A | 6/1997 | Weinstock et al. |
| 5,653,684 A | 8/1997 | Laptewicz et al. |
| 5,662,703 A | 9/1997 | Yurek et al. |
| 5,746,758 A | 5/1998 | Nordgren et al. |
| 5,749,858 A | 5/1998 | Cramer |
| 5,769,816 A | 6/1998 | Barbut et al. |
| 5,782,817 A | 7/1998 | Franzel et al. |
| 5,800,457 A | 9/1998 | Gelbfish |
| 5,827,229 A | 10/1998 | Auth et al. |
| 5,846,251 A | 12/1998 | Hart |
| 5,860,938 A | 1/1999 | Lafontaine et al. |
| 5,873,866 A | 2/1999 | Kondo et al. |
| 5,873,882 A | 2/1999 | Straub et al. |
| 5,867,385 A | 3/1999 | Ikari et al. |
| 5,876,414 A | 3/1999 | Straub |
| 5,895,406 A | 4/1999 | Gray et al. |
| 5,908,435 A | 6/1999 | Samuels |
| 5,911,710 A | 6/1999 | Barry et al. |
| 5,911,728 A | 6/1999 | Sepetka et al. |
| 5,911,733 A | 6/1999 | Parodi |
| 5,911,754 A | 6/1999 | Kanesaka et al. |
| 5,938,645 A | 8/1999 | Gordon |

(56) References Cited

U.S. PATENT DOCUMENTS

| | | |
|---|---|---|
| 5,941,869 A | 8/1999 | Patterson et al. |
| 5,947,985 A | 9/1999 | Imram |
| 5,951,539 A | 9/1999 | Nita et al. |
| 5,954,737 A | 9/1999 | Lee |
| 5,971,938 A | 10/1999 | Hart et al. |
| 5,971,958 A | 10/1999 | Zhang |
| 5,972,019 A | 10/1999 | Engelson et al. |
| 5,974,938 A | 11/1999 | Lloyd |
| 5,989,233 A | 11/1999 | Yoon |
| 5,993,483 A | 11/1999 | Gianotti |
| 6,017,335 A | 1/2000 | Burnham |
| 6,030,397 A | 2/2000 | Moneti et al. |
| 6,059,745 A | 5/2000 | Gelbfish |
| 6,059,814 A | 5/2000 | Ladd |
| 6,066,158 A | 5/2000 | Engelson et al. |
| 6,068,645 A | 5/2000 | Tu |
| 6,126,635 A | 10/2000 | Simpson et al. |
| 6,142,987 A | 11/2000 | Tsugita |
| 6,146,396 A | 11/2000 | Konya et al. |
| 6,146,403 A | 11/2000 | St. Germain |
| 6,152,144 A | 11/2000 | Lesh et al. |
| 6,152,909 A | 11/2000 | Bagaoisan et al. |
| 6,152,946 A | 11/2000 | Broome et al. |
| 6,156,055 A | 12/2000 | Ravenscroft |
| 6,159,230 A | 12/2000 | Samuels |
| 6,165,196 A | 12/2000 | Stack et al. |
| 6,168,579 B1 | 1/2001 | Tsugita |
| 6,179,859 B1 | 1/2001 | Bates et al. |
| 6,221,006 B1 | 4/2001 | Dubrul et al. |
| 6,228,060 B1 | 5/2001 | Howell |
| 6,238,412 B1 | 5/2001 | Dubrul et al. |
| 6,245,078 B1 | 6/2001 | Ouchi |
| 6,245,089 B1 | 6/2001 | Daniel et al. |
| 6,254,571 B1 | 7/2001 | Hart |
| 6,258,115 B1 | 7/2001 | Dubrul |
| 6,264,663 B1 | 7/2001 | Cano |
| 6,306,163 B1 | 10/2001 | Fitz |
| 6,322,572 B1 | 11/2001 | Lee |
| 6,350,271 B1 | 2/2002 | Kurz et al. |
| 6,361,545 B1 | 3/2002 | Macoviak et al. |
| 6,364,895 B1 | 4/2002 | Greenhalgh |
| 6,368,339 B1 | 4/2002 | Amplatz |
| 6,383,205 B1 | 5/2002 | Samson et al. |
| 6,402,771 B1 | 6/2002 | Palmer et al. |
| 6,413,235 B1 | 7/2002 | Parodi |
| 6,423,032 B2 | 7/2002 | Parodi |
| 6,432,122 B1 | 8/2002 | Gilson et al. |
| 6,436,085 B1 | 8/2002 | Lauer |
| 6,451,036 B1 | 9/2002 | Heitzmann et al. |
| 6,458,103 B1 | 10/2002 | Albert et al. |
| 6,475,236 B1 | 11/2002 | Roubin et al. |
| 6,481,439 B1 | 11/2002 | Lewis et al. |
| 6,485,502 B2 | 11/2002 | Don Michael |
| 6,508,782 B1 | 1/2003 | Evans et al. |
| 6,511,492 B1 | 1/2003 | Rosenbluth et al. |
| 6,514,273 B1 | 2/2003 | Voss et al. |
| 6,530,923 B1 | 3/2003 | Dubrul et al. |
| 6,530,935 B2 | 3/2003 | Wensel et al. |
| 6,540,722 B1 | 4/2003 | Boyle et al. |
| 6,544,276 B1 | 4/2003 | Azizi |
| 6,544,278 B1 | 4/2003 | Vrba et al. |
| 6,544,279 B1 | 4/2003 | Hopkins et al. |
| 6,551,342 B1 | 4/2003 | Shen et al. |
| 6,564,828 B1 | 5/2003 | Ishida |
| 6,569,181 B1 | 5/2003 | Burns |
| 6,575,995 B1 | 6/2003 | Huter et al. |
| 6,589,263 B1 | 7/2003 | Hopkins et al. |
| 6,589,264 B1 | 7/2003 | Barbut et al. |
| 6,596,011 B2 | 7/2003 | Johnson et al. |
| 6,602,271 B2 | 8/2003 | Adams et al. |
| 6,605,074 B2 | 8/2003 | Zadno-azizi et al. |
| 6,605,102 B1 | 8/2003 | Mazzocchi et al. |
| 6,610,077 B1 | 8/2003 | Hancock et al. |
| 6,620,148 B1 | 9/2003 | Tsugita |
| 6,620,179 B2 | 9/2003 | Brook et al. |
| 6,620,182 B1 | 9/2003 | Khosravi et al. |
| 6,623,460 B1 | 9/2003 | Heck |
| 6,635,068 B1 | 10/2003 | Dubrul et al. |
| 6,645,222 B1 | 11/2003 | Parodi et al. |
| 6,660,013 B2 | 12/2003 | Rabiner et al. |
| 6,660,014 B2 | 12/2003 | Demarais et al. |
| 6,663,650 B2 | 12/2003 | Sepetka et al. |
| 6,692,504 B2 | 2/2004 | Kurz et al. |
| 6,699,260 B2 | 3/2004 | Dubrul et al. |
| 6,702,830 B1 | 3/2004 | Demarais et al. |
| 6,719,717 B1 | 4/2004 | Johnson et al. |
| 6,755,847 B2 | 6/2004 | Eskuri |
| 6,767,353 B1 | 7/2004 | Shiber |
| 6,776,770 B1 | 8/2004 | Trerotola |
| 6,790,204 B2 | 9/2004 | Zadno-azizi et al. |
| 6,800,080 B1 | 10/2004 | Bates |
| 6,818,006 B2 | 11/2004 | Douk et al. |
| 6,824,545 B2 | 11/2004 | Sepetka et al. |
| 6,824,550 B1 | 11/2004 | Noriega et al. |
| 6,824,553 B1 | 11/2004 | Gene et al. |
| 6,830,561 B2 | 12/2004 | Jansen et al. |
| 6,846,029 B1 | 1/2005 | Ragner et al. |
| 6,902,540 B2 | 6/2005 | Dorros et al. |
| 6,908,455 B2 * | 6/2005 | Hajianpour ............ A61M 1/84 604/266 |
| 6,939,361 B1 | 9/2005 | Kleshinski |
| 6,942,682 B2 | 9/2005 | Vrba et al. |
| 6,945,977 B2 | 9/2005 | Demarais et al. |
| 6,960,189 B2 | 11/2005 | Bates et al. |
| 6,960,222 B2 | 11/2005 | Vo et al. |
| 7,004,931 B2 | 2/2006 | Hogendijk |
| 7,004,954 B1 | 2/2006 | Voss et al. |
| 7,036,707 B2 | 5/2006 | Aota et al. |
| 7,041,084 B2 | 5/2006 | Fotjik |
| 7,052,500 B2 | 5/2006 | Bashiri et al. |
| 7,056,328 B2 | 6/2006 | Arnott |
| 7,063,707 B2 | 6/2006 | Bose et al. |
| 7,069,835 B2 | 7/2006 | Nishri et al. |
| 7,094,249 B1 | 8/2006 | Thomas et al. |
| 7,122,034 B2 | 10/2006 | Belhe et al. |
| 7,128,073 B1 | 10/2006 | van der Burg et al. |
| 7,152,605 B2 | 12/2006 | Khairkhahan et al. |
| 7,179,273 B1 | 2/2007 | Palmer et al. |
| 7,223,253 B2 | 5/2007 | Hogendijk |
| 7,232,432 B2 | 6/2007 | Fulton, III et al. |
| 7,244,243 B2 | 7/2007 | Lary |
| 7,285,126 B2 | 10/2007 | Sepetka et al. |
| 7,300,458 B2 | 11/2007 | Henkes et al. |
| 7,306,618 B2 | 12/2007 | Demond et al. |
| 7,320,698 B2 | 1/2008 | Eskuri |
| 7,323,002 B2 | 1/2008 | Johnson et al. |
| 7,331,980 B2 | 2/2008 | Dubrul et al. |
| 7,481,805 B2 | 1/2009 | Magnusson |
| 7,534,234 B2 | 5/2009 | Fotjik |
| 7,578,830 B2 | 8/2009 | Kusleika et al. |
| 7,621,870 B2 | 11/2009 | Berrada et al. |
| 7,674,247 B2 | 3/2010 | Fotjik |
| 7,678,131 B2 | 3/2010 | Muller |
| 7,691,121 B2 | 4/2010 | Rosenbluth et al. |
| 7,695,458 B2 | 4/2010 | Belley et al. |
| 7,713,282 B2 | 5/2010 | Frazier et al. |
| 7,722,641 B2 | 5/2010 | van der Burg et al. |
| 7,763,010 B2 | 7/2010 | Evans et al. |
| 7,766,934 B2 | 8/2010 | Pal et al. |
| 7,775,501 B2 | 8/2010 | Kees |
| 7,780,696 B2 | 8/2010 | Daniel et al. |
| 7,815,608 B2 | 10/2010 | Schafersman et al. |
| 7,837,630 B2 * | 11/2010 | Nicoson ............ A61B 10/025 600/562 |
| 7,905,877 B1 | 3/2011 | Jilnenez et al. |
| 7,905,896 B2 | 3/2011 | Straub |
| 7,938,809 B2 | 5/2011 | Lampropoulos et al. |
| 7,938,820 B2 | 5/2011 | Webster et al. |
| 7,967,790 B2 | 6/2011 | Whiting et al. |
| 7,976,511 B2 | 7/2011 | Fotjik |
| 7,993,302 B2 | 8/2011 | Hebert et al. |
| 7,993,363 B2 | 8/2011 | Demond et al. |
| 7,998,104 B2 | 8/2011 | Chang |
| 8,021,351 B2 | 9/2011 | Boldenow et al. |

(56) References Cited

U.S. PATENT DOCUMENTS

| | | |
|---|---|---|
| 8,043,313 B2 | 10/2011 | Krolik et al. |
| 8,052,640 B2 | 11/2011 | Fiorella et al. |
| 8,057,496 B2 | 11/2011 | Fischer, Jr. |
| 8,057,497 B1 | 11/2011 | Raju et al. |
| 8,066,757 B2 | 11/2011 | Ferrera et al. |
| 8,070,694 B2 | 12/2011 | Galdonik et al. |
| 8,070,769 B2 | 12/2011 | Broome |
| 8,070,791 B2 | 12/2011 | Ferrera et al. |
| 8,075,510 B2 | 12/2011 | Aklog et al. |
| 8,080,032 B2 | 12/2011 | van Der Burg et al. |
| 8,088,140 B2 | 1/2012 | Ferrera et al. |
| 8,092,486 B2 | 1/2012 | Berrada et al. |
| 8,100,935 B2 | 1/2012 | Rosenbluth et al. |
| 8,109,962 B2 | 2/2012 | Pal |
| 8,118,275 B2 | 2/2012 | Mialhe |
| 8,118,829 B2 | 2/2012 | Carrison et al. |
| 8,157,760 B2 | 4/2012 | Criado et al. |
| 8,187,465 B2 | 5/2012 | Nierich |
| 8,197,493 B2 | 6/2012 | Ferrera et al. |
| 8,246,641 B2 | 8/2012 | Osborne et al. |
| 8,261,648 B1 | 9/2012 | Marchand et al. |
| 8,267,897 B2 | 9/2012 | Wells |
| 8,298,257 B2 | 10/2012 | Sepetka et al. |
| 8,317,748 B2 | 11/2012 | Fiorella et al. |
| 8,337,450 B2 | 12/2012 | Fotjik |
| RE43,902 E | 1/2013 | Hopkins et al. |
| 8,343,167 B2 | 1/2013 | Henson |
| 8,357,178 B2 | 1/2013 | Grandfield et al. |
| 8,361,104 B2 | 1/2013 | Jones et al. |
| 8,409,215 B2 | 4/2013 | Sepetka et al. |
| 8,439,858 B2 | 5/2013 | Huang et al. |
| 8,480,708 B2 | 7/2013 | Kassab et al. |
| 8,486,105 B2 | 7/2013 | Demond et al. |
| 8,491,539 B2 | 7/2013 | Fotjik |
| 8,512,352 B2 | 8/2013 | Martin |
| 8,523,897 B2 | 9/2013 | van Der Burg et al. |
| 8,529,596 B2 | 9/2013 | Grandfield et al. |
| 8,535,283 B2 | 9/2013 | Heaton et al. |
| 8,535,334 B2 | 9/2013 | Martin |
| 8,535,343 B2 | 9/2013 | van Der Burg et al. |
| 8,545,526 B2 | 10/2013 | Martin et al. |
| 8,568,432 B2 | 10/2013 | Straub |
| 8,568,465 B2 | 10/2013 | Freudenthal et al. |
| 8,574,262 B2 | 11/2013 | Ferrera et al. |
| 8,579,915 B2 | 11/2013 | French et al. |
| 8,585,713 B2 | 11/2013 | Ferrera et al. |
| 8,608,754 B2 | 12/2013 | Wensel et al. |
| 8,613,717 B2 | 12/2013 | Aklog et al. |
| 8,632,584 B2 | 1/2014 | Henkes et al. |
| 8,647,367 B2 | 2/2014 | Kassab et al. |
| 8,657,867 B2 | 2/2014 | Dorn et al. |
| 8,696,622 B2 | 4/2014 | Fiorella et al. |
| 8,715,314 B1 | 5/2014 | Janardhan et al. |
| 8,721,714 B2 | 5/2014 | Kelley |
| 8,734,374 B2 | 5/2014 | Aklog et al. |
| 8,753,322 B2 | 6/2014 | Hu et al. |
| 8,764,730 B2 | 7/2014 | Taber |
| 8,771,289 B2 | 7/2014 | Mohiuddin et al. |
| 8,777,893 B2 | 7/2014 | Malewicz |
| 8,784,441 B2 | 7/2014 | Rosenbluth et al. |
| 8,784,442 B2 | 7/2014 | Jones et al. |
| 8,784,469 B2 | 7/2014 | Kassab |
| 8,795,305 B2 | 8/2014 | Martin et al. |
| 8,795,317 B2 | 8/2014 | Grandfield et al. |
| 8,795,345 B2 | 8/2014 | Grandfield et al. |
| 8,801,748 B2 | 8/2014 | Martin |
| 8,808,259 B2 | 8/2014 | Walton et al. |
| 8,814,927 B2 | 8/2014 | Shin et al. |
| 8,820,207 B2 | 9/2014 | Marchand et al. |
| 8,826,791 B2 | 9/2014 | Thompson et al. |
| 8,828,044 B2 | 9/2014 | Aggerholm et al. |
| 8,833,224 B2 | 9/2014 | Thompson et al. |
| 8,834,519 B2 | 9/2014 | van Der Burg et al. |
| 8,845,621 B2 | 9/2014 | Fotjik |
| 8,852,205 B2 | 10/2014 | Brady et al. |
| 8,852,226 B2 | 10/2014 | Gilson et al. |
| 8,939,991 B2 | 1/2015 | Krolik et al. |
| 8,945,143 B2 | 2/2015 | Ferrera et al. |
| 8,945,172 B2 | 2/2015 | Ferrera et al. |
| 8,956,384 B2 | 2/2015 | Berrada et al. |
| 8,992,504 B2 | 3/2015 | Castella et al. |
| 9,005,172 B2 | 4/2015 | Chung |
| 9,011,551 B2 | 4/2015 | Oral et al. |
| 9,028,401 B1 | 5/2015 | Bacich et al. |
| 9,044,575 B2 | 6/2015 | Beasley et al. |
| 9,072,537 B2 | 7/2015 | Grandfield et al. |
| 9,078,682 B2 | 7/2015 | Lenker et al. |
| 9,101,382 B2 | 8/2015 | Krolik et al. |
| 9,125,683 B2 | 9/2015 | Farhangnia et al. |
| 9,126,016 B2 | 9/2015 | Fulton |
| 9,126,020 B2 | 9/2015 | Farhangnia et al. |
| 9,149,609 B2 | 10/2015 | Ansel et al. |
| 9,155,552 B2 | 10/2015 | Ulm, III |
| 9,161,766 B2 | 10/2015 | Slee et al. |
| 9,168,043 B2 | 10/2015 | van Der Burg et al. |
| 9,173,668 B2 | 11/2015 | Ulm, III |
| 9,186,487 B2 | 11/2015 | Dubrul et al. |
| D744,639 S | 12/2015 | Aklog et al. |
| 9,204,887 B2 | 12/2015 | Cully et al. |
| 9,216,277 B2 | 12/2015 | Myers |
| 9,241,669 B2 | 1/2016 | Pugh et al. |
| 9,358,037 B2 | 1/2016 | Farhangnia et al. |
| 9,254,352 B2 | 2/2016 | Kumar et al. |
| 9,259,237 B2 | 2/2016 | Quick et al. |
| 9,265,512 B2 | 2/2016 | Carrison et al. |
| 9,283,066 B2 | 3/2016 | Hopkins et al. |
| 9,301,769 B2 | 4/2016 | Brady et al. |
| 9,351,747 B2 | 5/2016 | Kugler et al. |
| 9,402,938 B2 | 8/2016 | Aklog et al. |
| 9,439,664 B2 | 9/2016 | Sos |
| 9,439,751 B2 | 9/2016 | White et al. |
| 9,456,834 B2 | 10/2016 | Folk |
| 9,463,035 B1 | 10/2016 | Greenhalgh et al. |
| 9,463,036 B2 | 10/2016 | Brady et al. |
| 9,492,635 B2 | 11/2016 | Beasley et al. |
| 9,526,864 B2 | 12/2016 | Quick |
| 9,526,865 B2 | 12/2016 | Quick |
| 9,532,792 B2 | 1/2017 | Galdonik et al. |
| 9,545,464 B2 | 1/2017 | Roche et al. |
| 9,566,073 B2 | 2/2017 | Kassab et al. |
| 9,566,179 B2 | 2/2017 | Andreas et al. |
| 9,566,424 B2 | 2/2017 | Pessin |
| 9,579,116 B1 | 2/2017 | Nguyen et al. |
| 9,581,942 B1 | 2/2017 | Shippert |
| 9,616,213 B2 | 4/2017 | Furnish et al. |
| 9,636,206 B2 | 5/2017 | Nguyen et al. |
| 9,643,035 B2 | 5/2017 | Mastenbroek |
| 9,662,129 B2 | 5/2017 | Galdonik et al. |
| 9,700,332 B2 | 7/2017 | Marchand et al. |
| 9,717,488 B2 | 8/2017 | Kassab et al. |
| 9,717,514 B2 | 8/2017 | Martin et al. |
| 9,717,519 B2 | 8/2017 | Rosenbluth et al. |
| 9,744,024 B2 | 8/2017 | Nguyen et al. |
| 9,757,137 B2 | 9/2017 | Krolik et al. |
| 9,827,084 B2 | 11/2017 | Bonnette et al. |
| 9,827,364 B2 | 11/2017 | Peticca et al. |
| 9,844,386 B2 | 12/2017 | Nguyen et al. |
| 9,844,387 B2 | 12/2017 | Marchand et al. |
| 9,844,643 B2 | 12/2017 | Beasley et al. |
| 9,848,975 B2 | 12/2017 | Hauser |
| 9,849,014 B2 | 12/2017 | Kusleika |
| 9,884,387 B2 | 2/2018 | Plha |
| 9,937,321 B2 | 4/2018 | Welch et al. |
| 9,962,178 B2 | 5/2018 | Greenhalgh et al. |
| 9,980,813 B2 | 5/2018 | Eller |
| 9,999,493 B2 | 6/2018 | Nguyen et al. |
| 10,004,531 B2 | 6/2018 | Rosenbluth et al. |
| 10,010,335 B2 | 7/2018 | Greenhalgh et al. |
| 10,016,206 B1 | 7/2018 | Yang |
| 10,016,266 B2 | 7/2018 | Hauser |
| 10,028,759 B2 | 7/2018 | Wallace et al. |
| 10,045,790 B2 | 8/2018 | Cox et al. |
| 10,058,339 B2 | 8/2018 | Galdonik et al. |
| 10,098,651 B2 | 10/2018 | Marchand et al. |

(56) References Cited

U.S. PATENT DOCUMENTS

| | | |
|---|---|---|
| 10,130,385 B2 | 11/2018 | Farhangnia et al. |
| 10,130,795 B2 | 11/2018 | Parhangnia et al. |
| 10,179,224 B2 | 1/2019 | Yang et al. |
| 10,183,147 B2 | 1/2019 | Yang et al. |
| 10,183,159 B2 | 1/2019 | Nobles et al. |
| 10,188,829 B2 | 1/2019 | Beasley et al. |
| 10,195,320 B2 | 2/2019 | Fisher et al. |
| 10,226,263 B2 | 3/2019 | Look et al. |
| 10,238,406 B2 | 3/2019 | Cox et al. |
| 10,271,864 B2 | 4/2019 | Greenhalgh et al. |
| 10,327,883 B2 | 6/2019 | Yachia |
| 10,335,186 B2 | 7/2019 | Rosenbluth et al. |
| 10,342,571 B2 | 7/2019 | Marchand et al. |
| 10,349,960 B2 | 7/2019 | Quick |
| 10,383,644 B2 | 8/2019 | Molael et al. |
| 10,383,983 B2 | 8/2019 | Aklog et al. |
| 10,384,034 B2 | 8/2019 | Carrison et al. |
| 10,426,510 B2 | 10/2019 | Farhangnia et al. |
| 10,426,644 B2 | 10/2019 | Shrivastava et al. |
| 10,441,745 B2 | 10/2019 | Yang et al. |
| 10,456,151 B2 | 10/2019 | Slee et al. |
| 10,456,555 B2 | 10/2019 | Carrison et al. |
| 10,471,234 B2 | 11/2019 | Taber |
| 10,478,535 B2 | 11/2019 | Ogle |
| 10,485,952 B2 | 11/2019 | Carrison et al. |
| 10,492,805 B2 | 12/2019 | Culbert et al. |
| 10,524,811 B2 | 1/2020 | Marchand et al. |
| 10,531,883 B1 | 1/2020 | Deville et al. |
| 10,537,710 B2 | 1/2020 | Jalgaonkar et al. |
| 10,561,440 B2 | 2/2020 | Look et al. |
| 10,588,655 B2 | 3/2020 | Rosenbluth et al. |
| 10,648,268 B2 | 5/2020 | Jaffrey et al. |
| 10,661,053 B2 | 5/2020 | Yang et al. |
| 10,695,159 B2 | 6/2020 | Hauser |
| 10,709,471 B2 | 7/2020 | Rosenbluth et al. |
| 10,729,455 B2 | 8/2020 | Goyal et al. |
| 10,743,907 B2 | 8/2020 | Bruzzi et al. |
| 10,772,636 B2 | 9/2020 | Kassab et al. |
| 10,779,852 B2 | 9/2020 | Bruzzi et al. |
| 10,779,855 B2 | 9/2020 | Garrison |
| 10,799,331 B2 | 10/2020 | Hauser |
| 10,799,671 B2 | 10/2020 | Shimada et al. |
| 10,813,663 B2 | 10/2020 | Bruzzi et al. |
| 10,828,061 B2 | 11/2020 | Bonnette et al. |
| 10,835,711 B2 | 11/2020 | Yang et al. |
| 10,874,421 B2 | 12/2020 | Bruzzi et al. |
| 10,912,577 B2 | 2/2021 | Marchand et al. |
| 10,926,060 B2 | 2/2021 | Stern et al. |
| 10,939,932 B1 | 3/2021 | Yang |
| 10,953,195 B2 | 3/2021 | Jalgaonkar et al. |
| 10,960,114 B2 | 3/2021 | Goisis |
| 10,967,111 B2 | 4/2021 | Iida |
| 10,994,063 B2 | 5/2021 | Fisher et al. |
| 11,000,682 B2 | 5/2021 | Merritt et al. |
| 11,013,523 B2 | 5/2021 | Arad Hadar |
| 11,058,445 B2 | 7/2021 | Cox et al. |
| 11,058,451 B2 | 7/2021 | Marchand et al. |
| 11,065,019 B1 | 7/2021 | Chou et al. |
| 11,065,028 B2 | 7/2021 | Parhangnia et al. |
| 11,147,571 B2 | 10/2021 | Cox et al. |
| 11,147,948 B2 | 10/2021 | Beasley et al. |
| 11,147,949 B2 | 10/2021 | Yang et al. |
| 11,154,314 B2 | 10/2021 | Quick |
| 11,166,703 B2 | 11/2021 | Kassab et al. |
| 11,185,664 B2 | 11/2021 | Carrison et al. |
| 11,197,684 B1 | 12/2021 | Ngo et al. |
| 11,213,356 B2 | 1/2022 | Tanner et al. |
| 11,224,450 B2 | 1/2022 | Chou et al. |
| 11,224,721 B2 | 1/2022 | Carrison et al. |
| 11,253,277 B2 | 2/2022 | Buck et al. |
| 11,259,821 B2 | 3/2022 | Buck et al. |
| 11,266,825 B2 | 3/2022 | Peter et al. |
| 11,278,307 B2 | 3/2022 | Bruzzi et al. |
| 11,305,094 B2 | 4/2022 | Carrison et al. |
| 11,317,939 B2 | 5/2022 | Bruzzi et al. |
| 11,337,714 B2 | 5/2022 | Ferrera et al. |
| 11,383,064 B2 | 7/2022 | Carrison et al. |
| 11,395,903 B2 | 7/2022 | Carrison et al. |
| 11,406,418 B2 | 8/2022 | Bruzzi et al. |
| 11,406,801 B2 | 8/2022 | Fojtik et al. |
| 11,419,621 B2 | 8/2022 | Goyal et al. |
| 11,433,218 B2 | 9/2022 | Quick et al. |
| 11,439,799 B2 | 9/2022 | Buck et al. |
| 11,457,936 B2 | 10/2022 | Buck et al. |
| 11,478,262 B2 | 10/2022 | Ngo et al. |
| 11,529,158 B2 | 12/2022 | Hauser |
| 11,553,935 B2 | 1/2023 | Buck et al. |
| 11,553,942 B2 | 1/2023 | Bonnette et al. |
| 11,554,005 B2 | 1/2023 | Merritt et al. |
| 11,559,382 B2 | 1/2023 | Merritt et al. |
| 11,576,691 B2 | 2/2023 | Chou et al. |
| 11,589,880 B2 | 2/2023 | Aklog et al. |
| 11,596,768 B2 | 3/2023 | Stern et al. |
| 11,607,483 B2 | 3/2023 | Iida |
| 11,633,272 B2 | 4/2023 | Buck et al. |
| 11,638,637 B2 | 5/2023 | Buck et al. |
| 11,642,209 B2 | 5/2023 | Merritt et al. |
| 11,648,028 B2 | 5/2023 | Rosenbluth et al. |
| 11,672,561 B2 | 6/2023 | Look et al. |
| 11,697,011 B2 | 7/2023 | Merritt et al. |
| 11,697,012 B2 | 7/2023 | Merritt et al. |
| 11,744,691 B2 | 9/2023 | Merritt et al. |
| 11,806,033 B2 | 11/2023 | Marchand et al. |
| 11,819,228 B2 | 11/2023 | Buck et al. |
| 11,832,837 B2 | 12/2023 | Hauser |
| 11,832,838 B2 | 12/2023 | Hauser |
| 11,833,023 B2 | 12/2023 | Hauser |
| 11,839,393 B2 | 12/2023 | Hauser |
| 11,844,921 B2 | 12/2023 | Merritt et al. |
| 11,849,963 B2 | 12/2023 | Quick |
| 11,865,291 B2 | 1/2024 | Merritt et al. |
| 11,890,180 B2 | 2/2024 | Merritt et al. |
| 11,918,243 B2 | 3/2024 | Marchand et al. |
| 11,918,244 B2 | 3/2024 | Marchand et al. |
| 11,925,369 B2 | 3/2024 | Hauser |
| 11,937,834 B2 | 3/2024 | Dinh |
| 11,937,838 B2 | 3/2024 | Cox et al. |
| 11,963,861 B2 | 4/2024 | Strauss et al. |
| 11,969,178 B2 | 4/2024 | Hauser |
| 11,969,331 B2 | 4/2024 | Merritt et al. |
| 11,969,332 B2 | 4/2024 | Merritt et al. |
| 11,969,333 B2 | 4/2024 | Merritt et al. |
| 11,974,909 B2 | 5/2024 | Merritt et al. |
| 11,974,910 B2 | 5/2024 | Merritt et al. |
| 11,980,537 B2 | 5/2024 | Merritt et al. |
| 11,986,382 B2 | 5/2024 | Merritt et al. |
| 11,998,436 B2 | 6/2024 | Merritt et al. |
| 12,016,580 B2 | 6/2024 | Quick et al. |
| 12,023,057 B2 | 7/2024 | Hauser |
| 12,102,343 B2 | 10/2024 | Quick |
| 12,109,384 B2 | 10/2024 | Merritt et al. |
| 2001/0004699 A1 | 6/2001 | Gittings et al. |
| 2001/0031981 A1 | 10/2001 | Evans et al. |
| 2001/0041881 A1 | 11/2001 | Sarge et al. |
| 2001/0041909 A1 | 11/2001 | Tsugita et al. |
| 2001/0049486 A1 | 12/2001 | Evans et al. |
| 2001/0051810 A1 | 12/2001 | Dubrul et al. |
| 2002/0022858 A1 | 2/2002 | Demond et al. |
| 2002/0022859 A1 | 2/2002 | Hogendijk |
| 2002/0026211 A1 | 2/2002 | Khosravi et al. |
| 2002/0032455 A1 | 3/2002 | Boock et al. |
| 2002/0049452 A1 | 4/2002 | Kurz et al. |
| 2002/0095161 A1 | 7/2002 | Dhindsa |
| 2002/0095171 A1 | 7/2002 | Belef |
| 2002/0111648 A1 | 8/2002 | Kusleika et al. |
| 2002/0120277 A1 | 8/2002 | Hauschild et al. |
| 2002/0147458 A1 | 10/2002 | Hiblar et al. |
| 2002/0151918 A1 | 10/2002 | Lafontaine et al. |
| 2002/0156457 A1 | 10/2002 | Fisher |
| 2002/0161392 A1 | 10/2002 | Dubrul |
| 2002/0169474 A1 | 11/2002 | Kusleika |
| 2002/0173819 A1 | 11/2002 | Leeflang et al. |
| 2002/0188276 A1 | 12/2002 | Evans et al. |
| 2003/0004536 A1 | 1/2003 | Boylan et al. |

(56) References Cited

U.S. PATENT DOCUMENTS

| | | |
|---|---|---|
| 2003/0023263 A1 | 1/2003 | Krolik et al. |
| 2003/0069601 A1 | 4/2003 | Nowakowski et al. |
| 2003/0083693 A1 | 5/2003 | Daniel et al. |
| 2003/0100919 A1 | 5/2003 | Hopkins et al. |
| 2003/0114875 A1 | 6/2003 | Sjostrom |
| 2003/0116731 A1 | 6/2003 | Hartley |
| 2003/0125663 A1 | 7/2003 | Coleman et al. |
| 2003/0135151 A1 | 7/2003 | Deng |
| 2003/0135230 A1 | 7/2003 | Massey et al. |
| 2003/0135258 A1 | 7/2003 | Andreas et al. |
| 2003/0153873 A1 | 8/2003 | Luther et al. |
| 2003/0153973 A1 | 8/2003 | Soun et al. |
| 2003/0168068 A1 | 9/2003 | Poole et al. |
| 2003/0176884 A1 | 9/2003 | Berrada et al. |
| 2003/0191425 A1 | 10/2003 | Rosenblatt et al. |
| 2003/0191516 A1 | 10/2003 | Weldon et al. |
| 2003/0208224 A1 | 11/2003 | Broome |
| 2003/0216774 A1 | 11/2003 | Larson |
| 2003/0225379 A1 | 12/2003 | Schaffer et al. |
| 2004/0019310 A1 | 1/2004 | Hogendijk |
| 2004/0039351 A1 | 2/2004 | Barrett |
| 2004/0039412 A1 | 2/2004 | Isshiki et al. |
| 2004/0068288 A1 | 4/2004 | Palmer et al. |
| 2004/0073243 A1 | 4/2004 | Sepetka et al. |
| 2004/0098033 A1 | 5/2004 | Leeflang et al. |
| 2004/0102807 A1 | 5/2004 | Kusleika et al. |
| 2004/0122359 A1 | 6/2004 | Wenz et al. |
| 2004/0127936 A1 | 7/2004 | Salahieh et al. |
| 2004/0133232 A1 | 7/2004 | Rosenbluth et al. |
| 2004/0138525 A1 | 7/2004 | Saadat et al. |
| 2004/0138692 A1 | 7/2004 | Phung et al. |
| 2004/0167567 A1 | 8/2004 | Cano et al. |
| 2004/0199201 A1 | 10/2004 | Kellett et al. |
| 2004/0199202 A1 | 10/2004 | Dubrul et al. |
| 2004/0260344 A1 | 12/2004 | Lyons et al. |
| 2004/0267272 A1 | 12/2004 | Henniges et al. |
| 2005/0004534 A1 | 1/2005 | Lockwood et al. |
| 2005/0033172 A1 | 2/2005 | Dubrul et al. |
| 2005/0038468 A1 | 2/2005 | Panetta et al. |
| 2005/0054995 A1 | 3/2005 | Barzell et al. |
| 2005/0055047 A1 | 3/2005 | Greenhalgh |
| 2005/0080398 A1 | 4/2005 | Markel et al. |
| 2005/0085769 A1 | 4/2005 | MacMahon et al. |
| 2005/0085826 A1 | 4/2005 | Nair et al. |
| 2005/0085846 A1 | 4/2005 | Carrison et al. |
| 2005/0085849 A1 | 4/2005 | Sepetka et al. |
| 2005/0119668 A1 | 6/2005 | Teague et al. |
| 2005/0131387 A1 | 6/2005 | Pursley |
| 2005/0177132 A1 | 8/2005 | Lentz et al. |
| 2005/0187570 A1 | 8/2005 | Nguyen et al. |
| 2005/0203605 A1 | 9/2005 | Dolan |
| 2005/0283165 A1 | 12/2005 | Gadberry |
| 2005/0283166 A1 | 12/2005 | Greenhalgh et al. |
| 2005/0283186 A1 | 12/2005 | Berrada et al. |
| 2006/0020286 A1 | 1/2006 | Niermann |
| 2006/0042786 A1 | 3/2006 | West |
| 2006/0047286 A1 | 3/2006 | West |
| 2006/0074401 A1 | 4/2006 | Ross |
| 2006/0079787 A1 | 4/2006 | Whiting et al. |
| 2006/0085952 A1 | 4/2006 | Kaneko et al. |
| 2006/0089533 A1 | 4/2006 | Ziegler et al. |
| 2006/0100662 A1 | 5/2006 | Daniel et al. |
| 2006/0149219 A1 | 7/2006 | Calderon |
| 2006/0155305 A1 | 7/2006 | Freudenthal et al. |
| 2006/0173525 A1 | 8/2006 | Behl et al. |
| 2006/0195137 A1 | 8/2006 | Sepetka et al. |
| 2006/0200221 A1 | 9/2006 | Malewicz |
| 2006/0217664 A1 | 9/2006 | Hattler et al. |
| 2006/0224177 A1 | 10/2006 | Finitsis |
| 2006/0229645 A1 | 10/2006 | Bonnette et al. |
| 2006/0247500 A1 | 11/2006 | Voegele et al. |
| 2006/0253145 A1 | 11/2006 | Lucas |
| 2006/0264905 A1 | 11/2006 | Eskridge et al. |
| 2006/0276874 A1 | 12/2006 | Wilson et al. |
| 2006/0282111 A1 | 12/2006 | Morsi |
| 2006/0293696 A1 | 12/2006 | Fahey et al. |
| 2007/0010787 A1 | 1/2007 | Hackett et al. |
| 2007/0038225 A1 | 2/2007 | Osborne |
| 2007/0093744 A1 | 4/2007 | Elmaleh |
| 2007/0112374 A1 | 5/2007 | Paul, Jr. et al. |
| 2007/0118165 A1 | 5/2007 | DeMello et al. |
| 2007/0149996 A1 | 6/2007 | Coughlin |
| 2007/0161963 A1 | 7/2007 | Smalling |
| 2007/0179513 A1 | 8/2007 | Deutsch |
| 2007/0191866 A1 | 8/2007 | Palmer et al. |
| 2007/0198028 A1 | 8/2007 | Miloslavski et al. |
| 2007/0208361 A1 | 9/2007 | Okushi et al. |
| 2007/0208367 A1 | 9/2007 | Fiorella et al. |
| 2007/0213753 A1 | 9/2007 | Waller |
| 2007/0213765 A1 | 9/2007 | Adams et al. |
| 2007/0233043 A1 | 10/2007 | Dayton et al. |
| 2007/0255252 A1 | 11/2007 | Mehta |
| 2007/0288054 A1 | 12/2007 | Tanaka et al. |
| 2008/0015541 A1 | 1/2008 | Rosenbluth et al. |
| 2008/0087853 A1 | 4/2008 | Kees |
| 2008/0088055 A1 | 4/2008 | Ross |
| 2008/0157017 A1 | 7/2008 | Macatangay et al. |
| 2008/0167678 A1 | 7/2008 | Morsi |
| 2008/0183136 A1 | 7/2008 | Lenker et al. |
| 2008/0228209 A1 | 9/2008 | DeMello et al. |
| 2008/0234715 A1 | 9/2008 | Pesce et al. |
| 2008/0234722 A1 | 9/2008 | Bonnette et al. |
| 2008/0262528 A1 | 10/2008 | Martin |
| 2008/0269798 A1 | 10/2008 | Ramzipoor et al. |
| 2008/0294096 A1 | 11/2008 | Uber, III et al. |
| 2008/0300466 A1 | 12/2008 | Gresham |
| 2008/0312681 A1 | 12/2008 | Ansel et al. |
| 2009/0018566 A1 | 1/2009 | Escudero et al. |
| 2009/0054918 A1 | 2/2009 | Henson |
| 2009/0062841 A1 | 3/2009 | Amplatz et al. |
| 2009/0069828 A1 | 3/2009 | Martin et al. |
| 2009/0076417 A1 | 3/2009 | Jones |
| 2009/0082857 A1 | 3/2009 | Lashinski et al. |
| 2009/0160112 A1 | 6/2009 | Ostrovsky |
| 2009/0163846 A1 | 6/2009 | Aklog et al. |
| 2009/0182362 A1 | 7/2009 | Thompson et al. |
| 2009/0192495 A1 | 7/2009 | Ostrovsky et al. |
| 2009/0281525 A1 | 11/2009 | Harding et al. |
| 2009/0292307 A1 | 11/2009 | Razack |
| 2009/0299393 A1 | 12/2009 | Martin et al. |
| 2009/0312786 A1 | 12/2009 | Trask et al. |
| 2010/0016837 A1 | 1/2010 | Howat |
| 2010/0030256 A1 | 2/2010 | Dubrul et al. |
| 2010/0042118 A1 | 2/2010 | Garrison et al. |
| 2010/0042136 A1 | 2/2010 | Berrada et al. |
| 2010/0087844 A1 | 4/2010 | Fischer, Jr. |
| 2010/0087850 A1 | 4/2010 | Razack |
| 2010/0094201 A1 | 4/2010 | Mallaby |
| 2010/0106081 A1 | 4/2010 | Brandeis |
| 2010/0114017 A1 | 5/2010 | Lenker et al. |
| 2010/0114113 A1 | 5/2010 | Dubrul et al. |
| 2010/0121312 A1 | 5/2010 | Gielenz et al. |
| 2010/0137846 A1 | 6/2010 | Desaletal |
| 2010/0190156 A1 | 7/2010 | Van Wordragen et al. |
| 2010/0204712 A1 | 8/2010 | Mallaby |
| 2010/0217276 A1 | 8/2010 | Garrison et al. |
| 2010/0249815 A1 | 9/2010 | Jantzen et al. |
| 2010/0268264 A1 | 10/2010 | Bonnette et al. |
| 2010/0318178 A1 | 12/2010 | Rapaport et al. |
| 2011/0009950 A1 | 1/2011 | Grandfield et al. |
| 2011/0034986 A1 | 2/2011 | Chou et al. |
| 2011/0034987 A1 | 2/2011 | Kennedy |
| 2011/0054405 A1 | 3/2011 | Whiting et al. |
| 2011/0060212 A1 | 3/2011 | Slee et al. |
| 2011/0071503 A1 | 3/2011 | Takagi et al. |
| 2011/0087173 A1 | 4/2011 | Sibbitt, Jr. et al. |
| 2011/0118817 A1 | 5/2011 | Gunderson et al. |
| 2011/0125181 A1 | 5/2011 | Brady et al. |
| 2011/0144592 A1 | 6/2011 | Wong et al. |
| 2011/0152823 A1 | 6/2011 | Mohluddin et al. |
| 2011/0152889 A1 | 6/2011 | Ashland |
| 2011/0152993 A1 | 6/2011 | Marchand et al. |
| 2011/0160742 A1 | 6/2011 | Ferrera et al. |
| 2011/0160763 A1 | 6/2011 | Ferrera et al. |

(56) References Cited

U.S. PATENT DOCUMENTS

| | | |
|---|---|---|
| 2011/0190806 A1 | 8/2011 | Wittens |
| 2011/0196309 A1 | 8/2011 | Wells |
| 2011/0196414 A1 | 8/2011 | Porter et al. |
| 2011/0213290 A1 | 9/2011 | Chin et al. |
| 2011/0213403 A1 | 9/2011 | Aboytes |
| 2011/0224707 A1 | 9/2011 | Miloslavski et al. |
| 2011/0245807 A1 | 10/2011 | Sakata et al. |
| 2011/0251629 A1 | 10/2011 | Galdonik et al. |
| 2011/0264132 A1 | 10/2011 | Strauss et al. |
| 2011/0264133 A1 | 10/2011 | Hanlon et al. |
| 2011/0265681 A1 | 11/2011 | Allen et al. |
| 2011/0288529 A1 | 11/2011 | Fulton |
| 2011/0288572 A1 | 11/2011 | Martin |
| 2011/0309037 A1 | 12/2011 | Lee |
| 2011/0319917 A1 | 12/2011 | Ferrera et al. |
| 2012/0059309 A1 | 3/2012 | di Palma et al. |
| 2012/0059356 A1 | 3/2012 | di Palma et al. |
| 2012/0083824 A1 | 4/2012 | Berrada et al. |
| 2012/0083868 A1 | 4/2012 | Shrivastava |
| 2012/0089216 A1 | 4/2012 | Rapaport et al. |
| 2012/0095448 A1 | 4/2012 | Kajii |
| 2012/0101480 A1 | 4/2012 | Ingle et al. |
| 2012/0101510 A1 | 4/2012 | Lenker et al. |
| 2012/0109109 A1 | 5/2012 | Kajii |
| 2012/0138832 A1 | 6/2012 | Townsend |
| 2012/0143123 A1 | 6/2012 | Agnew |
| 2012/0143239 A1 | 6/2012 | Aklog et al. |
| 2012/0165919 A1 | 6/2012 | Cox et al. |
| 2012/0172918 A1 | 7/2012 | Fifer et al. |
| 2012/0179181 A1 | 7/2012 | Straub et al. |
| 2012/0197277 A1 | 8/2012 | Stinis |
| 2012/0232655 A1 | 9/2012 | Lorrison et al. |
| 2012/0271105 A1 | 10/2012 | Nakamura et al. |
| 2012/0271231 A1 | 10/2012 | Agrawal |
| 2012/0277788 A1 | 11/2012 | Cattaneo |
| 2012/0310166 A1 | 12/2012 | Huff |
| 2013/0030460 A1 | 1/2013 | Marks et al. |
| 2013/0035628 A1 | 2/2013 | Garrison et al. |
| 2013/0046332 A1 | 2/2013 | Jones et al. |
| 2013/0066348 A1 | 3/2013 | Fiorella et al. |
| 2013/0092012 A1 | 4/2013 | Marchand et al. |
| 2013/0096571 A1 | 4/2013 | Massicotte et al. |
| 2013/0102996 A1 | 4/2013 | Strauss |
| 2013/0116708 A1 | 5/2013 | Ziniti et al. |
| 2013/0116721 A1 | 5/2013 | Takagi et al. |
| 2013/0123705 A1 | 5/2013 | Holm et al. |
| 2013/0126559 A1 | 5/2013 | Cowan et al. |
| 2013/0144326 A1 | 6/2013 | Brady et al. |
| 2013/0150793 A1 | 6/2013 | Beissel et al. |
| 2013/0165871 A1 | 6/2013 | Fiorella et al. |
| 2013/0184703 A1 | 7/2013 | Shireman et al. |
| 2013/0190701 A1 | 7/2013 | Kirn |
| 2013/0197454 A1 | 8/2013 | Shibata et al. |
| 2013/0197567 A1 | 8/2013 | Brady et al. |
| 2013/0204297 A1 | 8/2013 | Melsheimer et al. |
| 2013/0226196 A1 | 8/2013 | Smith |
| 2013/0270161 A1 | 10/2013 | Kumar et al. |
| 2013/0281788 A1 | 10/2013 | Garrison |
| 2013/0289608 A1 | 10/2013 | Tanaka et al. |
| 2013/0317589 A1 | 11/2013 | Martin et al. |
| 2013/0345739 A1 | 12/2013 | Brady et al. |
| 2014/0005712 A1 | 1/2014 | Martin |
| 2014/0005713 A1 | 1/2014 | Bowman |
| 2014/0005715 A1 | 1/2014 | Castella et al. |
| 2014/0005717 A1 | 1/2014 | Martin et al. |
| 2014/0025048 A1 | 1/2014 | Ward |
| 2014/0031856 A1 | 1/2014 | Martin |
| 2014/0046133 A1 | 2/2014 | Nakamura et al. |
| 2014/0046243 A1 | 2/2014 | Ray et al. |
| 2014/0052161 A1 | 2/2014 | Cully et al. |
| 2014/0074144 A1 | 3/2014 | Shrivastava et al. |
| 2014/0121672 A1 | 5/2014 | Folk |
| 2014/0155830 A1 | 6/2014 | Bonnette et al. |
| 2014/0155980 A1 | 6/2014 | Turjman |
| 2014/0163615 A1 | 6/2014 | Gadlage et al. |
| 2014/0180055 A1 | 6/2014 | Glynn et al. |
| 2014/0180397 A1 | 6/2014 | Gerberding et al. |
| 2014/0155908 A1 | 7/2014 | Rosenbluth et al. |
| 2014/0188127 A1 | 7/2014 | Dubrul et al. |
| 2014/0188143 A1 | 7/2014 | Martin et al. |
| 2014/0222070 A1 | 8/2014 | Belson et al. |
| 2014/0236219 A1 | 8/2014 | Dubrul et al. |
| 2014/0243882 A1 | 8/2014 | Ma |
| 2014/0257253 A1 | 9/2014 | Jemison |
| 2014/0257363 A1 | 9/2014 | Lippert |
| 2014/0276403 A1 | 9/2014 | Follmer et al. |
| 2014/0276592 A1 | 9/2014 | Mottola et al. |
| 2014/0296868 A1 | 10/2014 | Garrison et al. |
| 2014/0303658 A1 | 10/2014 | Bonnette et al. |
| 2014/0318354 A1 | 10/2014 | Thompson et al. |
| 2014/0324091 A1 | 10/2014 | Rosenbluth et al. |
| 2014/0330286 A1 | 11/2014 | Wallace et al. |
| 2014/0336691 A1 | 11/2014 | Jones et al. |
| 2014/0343593 A1 | 11/2014 | Chin et al. |
| 2014/0364896 A1 | 12/2014 | Consigny |
| 2014/0371779 A1 | 12/2014 | Vale et al. |
| 2015/0005781 A1 | 1/2015 | Lund-Clausen et al. |
| 2015/0005792 A1 | 1/2015 | Ahn |
| 2015/0018859 A1 | 1/2015 | Quick et al. |
| 2015/0018860 A1 | 1/2015 | Quick |
| 2015/0018929 A1 | 1/2015 | Martin et al. |
| 2015/0025555 A1 | 1/2015 | Sos |
| 2015/0032144 A1 | 1/2015 | Holloway |
| 2015/0059908 A1 | 3/2015 | Mollen |
| 2015/0088190 A1 | 3/2015 | Jensen |
| 2015/0127035 A1 | 5/2015 | Trapp et al. |
| 2015/0133990 A1 | 5/2015 | Davidson |
| 2015/0150672 A1 | 6/2015 | Ma |
| 2015/0164523 A1 | 6/2015 | Brady et al. |
| 2015/0164666 A1 | 6/2015 | Johnson et al. |
| 2015/0173782 A1 | 6/2015 | Garrison et al. |
| 2015/0190155 A1 | 7/2015 | Ulm, III |
| 2015/0190156 A1 | 7/2015 | Ulm, III |
| 2015/0196380 A1 | 7/2015 | Berrada et al. |
| 2015/0196744 A1 | 7/2015 | Aboytes |
| 2015/0209058 A1 | 7/2015 | Ferrera et al. |
| 2015/0209165 A1 | 7/2015 | Grandfield et al. |
| 2015/0238207 A1 | 8/2015 | Cox et al. |
| 2015/0250578 A1 | 9/2015 | Cook et al. |
| 2015/0265299 A1 | 9/2015 | Cooper et al. |
| 2015/0265423 A1 | 9/2015 | Ponticiello et al. |
| 2015/0283309 A1 | 10/2015 | Look et al. |
| 2015/0305756 A1 | 10/2015 | Rosenbluth |
| 2015/0305859 A1 | 10/2015 | Eller |
| 2015/0314050 A1 | 11/2015 | Beer |
| 2015/0327875 A1 | 11/2015 | Look et al. |
| 2015/0352325 A1 | 12/2015 | Quick |
| 2015/0360001 A1 | 12/2015 | Quick |
| 2015/0366690 A1 | 12/2015 | Lumauig |
| 2015/0374391 A1 | 12/2015 | Quick |
| 2016/0022293 A1 | 1/2016 | Dubrul et al. |
| 2016/0030708 A1 | 2/2016 | Casiello et al. |
| 2016/0038267 A1 | 2/2016 | Allen et al. |
| 2016/0058540 A1 | 3/2016 | Don Michael |
| 2016/0074627 A1 | 3/2016 | Cottone |
| 2016/0106353 A1 | 4/2016 | Schuetz et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0113666 A1 | 4/2016 | Quick |
| 2016/0128857 A1 | 5/2016 | Kao |
| 2016/0135829 A1 | 5/2016 | Holoehwost et al. |
| 2016/0143721 A1 | 5/2016 | Rosenbluth |
| 2016/0151605 A1 | 6/2016 | Welch et al. |
| 2016/0192912 A1 | 7/2016 | Kassab et al. |
| 2016/0206344 A1 | 7/2016 | Bruzzi et al. |
| 2016/0008014 A1 | 8/2016 | Rosenbluth |
| 2016/0220741 A1 | 8/2016 | Garrison et al. |
| 2016/0220795 A1 | 8/2016 | Korkuch et al. |
| 2016/0228134 A1 | 8/2016 | Martin et al. |
| 2016/0262774 A1 | 9/2016 | Honda |
| 2016/0262790 A1 | 9/2016 | Rosenbluth et al. |

(56) References Cited

U.S. PATENT DOCUMENTS

| | | |
|---|---|---|
| 2016/0287276 A1 | 10/2016 | Cox et al. |
| 2016/0367285 A1 | 12/2016 | Sos |
| 2017/0014560 A1 | 1/2017 | Minskoff et al. |
| 2017/0021130 A1 | 1/2017 | Dye |
| 2017/0037548 A1 | 2/2017 | Lee |
| 2017/0042571 A1 | 2/2017 | Levi |
| 2017/0043066 A1 | 2/2017 | Laub |
| 2017/0049942 A1 | 2/2017 | Conlan et al. |
| 2017/0056032 A1 | 3/2017 | Look et al. |
| 2017/0058623 A1 | 3/2017 | Jaffrey et al. |
| 2017/0079672 A1 | 3/2017 | Quick |
| 2017/0086864 A1 | 3/2017 | Greenhalgh et al. |
| 2017/0100142 A1 | 4/2017 | Look et al. |
| 2017/0105743 A1 | 4/2017 | Vale et al. |
| 2017/0105745 A1 | 4/2017 | Rosenbluth et al. |
| 2017/0112514 A1 | 4/2017 | Marchand et al. |
| 2017/0113005 A1 | 4/2017 | Linder et al. |
| 2017/0143359 A1 | 5/2017 | Nguyen et al. |
| 2017/0143880 A1 | 5/2017 | Luxon et al. |
| 2017/0143938 A1 | 5/2017 | Ogle et al. |
| 2017/0172591 A1 | 6/2017 | Ulm, III |
| 2017/0112513 A1 | 7/2017 | Marchand et al. |
| 2017/0189041 A1 | 7/2017 | Cox et al. |
| 2017/0196576 A1 | 7/2017 | Long et al. |
| 2017/0233908 A1 | 8/2017 | Kroczynski et al. |
| 2017/0238951 A1 | 8/2017 | Yang et al. |
| 2017/0252057 A1 | 9/2017 | Bonnette et al. |
| 2017/0265878 A1 | 9/2017 | Marchand et al. |
| 2017/0281204 A1 | 10/2017 | Garrison et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0319221 A1 | 11/2017 | Chu |
| 2017/0325839 A1 | 11/2017 | Rosenbluth et al. |
| 2017/0340867 A1 | 11/2017 | Accisano, II |
| 2017/0348014 A1 | 12/2017 | Wallace et al. |
| 2018/0014840 A1 | 1/2018 | Panian |
| 2018/0042623 A1 | 2/2018 | Satiste |
| 2018/0042624 A1 | 2/2018 | Greenhalgh et al. |
| 2018/0042626 A1 | 2/2018 | Greenhalgh et al. |
| 2018/0055999 A1 | 3/2018 | Bare et al. |
| 2018/0064453 A1 | 3/2018 | Garrison et al. |
| 2018/0064454 A1 | 3/2018 | Losordo et al. |
| 2018/0070968 A1 | 3/2018 | Wallace et al. |
| 2018/0078707 A1 | 3/2018 | Loonan |
| 2018/0092652 A1 | 4/2018 | Marchand et al. |
| 2018/0104404 A1 | 4/2018 | Ngo-Chu |
| 2018/0105963 A1 | 4/2018 | Quick |
| 2018/0125512 A1 | 5/2018 | Nguyen et al. |
| 2018/0184912 A1 | 7/2018 | Al-Ali |
| 2018/0193043 A1 | 7/2018 | Marchand et al. |
| 2018/0235742 A1 | 8/2018 | Fields et al. |
| 2018/0236205 A1 | 8/2018 | Krautkremer et al. |
| 2018/0250498 A1 | 9/2018 | Stern et al. |
| 2018/0256177 A1 | 9/2018 | Cooper et al. |
| 2018/0256178 A1 | 9/2018 | Cox et al. |
| 2018/0280623 A1 | 10/2018 | Pilkington |
| 2018/0296240 A1 | 10/2018 | Rosenbluth et al. |
| 2018/0338770 A1 | 11/2018 | Mogi et al. |
| 2018/0339130 A1 | 11/2018 | Ogle |
| 2018/0344339 A1 | 12/2018 | Cox et al. |
| 2018/0361116 A1 | 12/2018 | Quick et al. |
| 2019/0000492 A1 | 1/2019 | Casey et al. |
| 2019/0015298 A1 | 1/2019 | Beatty et al. |
| 2019/0046219 A1 | 2/2019 | Marchand et al. |
| 2019/0070401 A1 | 3/2019 | Merritt et al. |
| 2019/0117244 A1 | 4/2019 | Wallace et al. |
| 2019/0133622 A1 | 5/2019 | Wallace et al. |
| 2019/0133623 A1 | 5/2019 | Wallace et al. |
| 2019/0133624 A1 | 5/2019 | Wallace et al. |
| 2019/0133625 A1 | 5/2019 | Wallace et al. |
| 2019/0133626 A1 | 5/2019 | Wallace et al. |
| 2019/0133627 A1 | 5/2019 | Wallace et al. |
| 2019/0150959 A1 | 5/2019 | Cox et al. |
| 2019/0216476 A1 | 7/2019 | Barry et al. |
| 2019/0223893 A1 | 7/2019 | Gilvarry et al. |
| 2019/0231373 A1 | 8/2019 | Quick |
| 2019/0239910 A1 | 8/2019 | Brady et al. |
| 2019/0321071 A1 | 10/2019 | Marchand et al. |
| 2019/0328411 A1 | 10/2019 | Vale et al. |
| 2019/0336142 A1 | 11/2019 | Torrie et al. |
| 2019/0336148 A1 | 11/2019 | Greenhalgh et al. |
| 2019/0365395 A1 | 12/2019 | Tran et al. |
| 2019/0366036 A1 | 12/2019 | Jalgaonkar et al. |
| 2019/0366049 A1 | 12/2019 | Hannon et al. |
| 2020/0022711 A1 | 1/2020 | Look et al. |
| 2020/0030579 A1 | 1/2020 | Taber |
| 2020/0046368 A1 | 2/2020 | Merritt et al. |
| 2020/0046940 A1 | 2/2020 | Carrison et al. |
| 2020/0054861 A1 | 2/2020 | Korkuch et al. |
| 2020/0069889 A1 | 3/2020 | Lin |
| 2020/0078029 A1 | 3/2020 | Hansen et al. |
| 2020/0113412 A1 | 4/2020 | Jensen |
| 2020/0121334 A1 | 4/2020 | Galdonik et al. |
| 2020/0129741 A1 | 4/2020 | Kawwas et al. |
| 2020/0324079 A1 | 10/2020 | Jalgaonkar et al. |
| 2021/0022843 A1 | 1/2021 | Hauser |
| 2021/0038385 A1 | 2/2021 | Popp et al. |
| 2021/0113224 A1 | 4/2021 | Dinh |
| 2021/0128182 A1 | 5/2021 | Teigen et al. |
| 2021/0137667 A1 | 5/2021 | Sonnette et al. |
| 2021/0138194 A1 | 5/2021 | Carrison et al. |
| 2021/0154433 A1 | 5/2021 | Casey et al. |
| 2021/0186537 A1 | 6/2021 | Buck et al. |
| 2021/0186541 A1 | 6/2021 | Thress |
| 2021/0205577 A1 | 7/2021 | Jalgaonkar et al. |
| 2021/0236148 A1 | 8/2021 | Marchand et al. |
| 2021/0290925 A1 | 9/2021 | Merritt et al. |
| 2021/0315598 A1 | 10/2021 | Buck et al. |
| 2021/0316127 A1 | 10/2021 | Buck et al. |
| 2021/0330344 A1 | 10/2021 | Rosenbluth et al. |
| 2021/0378694 A1 | 12/2021 | Thress et al. |
| 2021/0393278 A1 | 12/2021 | O'Malley et al. |
| 2021/0404464 A1 | 12/2021 | Patoskie |
| 2022/0000505 A1 | 1/2022 | Hauser |
| 2022/0000506 A1 | 1/2022 | Hauser |
| 2022/0000507 A1 | 1/2022 | Hauser |
| 2022/0015798 A1 | 1/2022 | Marchand et al. |
| 2022/0021197 A1 | 1/2022 | Zhao et al. |
| 2022/0022898 A1 | 1/2022 | Cox et al. |
| 2022/0033888 A1 | 2/2022 | Schnall-Levin et al. |
| 2022/0039815 A1 | 2/2022 | Thress et al. |
| 2022/0125451 A1 | 4/2022 | Hauser |
| 2022/0142638 A1 | 5/2022 | Enright et al. |
| 2022/0151647 A1 | 5/2022 | Dolendo et al. |
| 2022/0152355 A1 | 5/2022 | Dolendo et al. |
| 2022/0160381 A1 | 5/2022 | Hauser |
| 2022/0160382 A1 | 5/2022 | Hauser |
| 2022/0160383 A1 | 5/2022 | Hauser |
| 2022/0211400 A1 | 7/2022 | Cox et al. |
| 2022/0211992 A1 | 7/2022 | Merritt et al. |
| 2022/0226555 A1 | 7/2022 | Sunenshine et al. |
| 2022/0240959 A1 | 8/2022 | Quick |
| 2022/0296797 A1 | 9/2022 | Chawla |
| 2022/0331554 A1 | 10/2022 | Beasley et al. |
| 2022/0346800 A1 | 11/2022 | Merritt et al. |
| 2022/0346813 A1 | 11/2022 | Quick |
| 2022/0346814 A1 | 11/2022 | Quick |
| 2022/0347455 A1 | 11/2022 | Merritt et al. |
| 2022/0362512 A1 | 11/2022 | Quick et al. |
| 2022/0370761 A1 | 11/2022 | Chou et al. |
| 2022/0378445 A1 | 12/2022 | Culbert et al. |
| 2022/0378446 A1 | 12/2022 | Culbert et al. |
| 2022/0378447 A1 | 12/2022 | Culbert et al. |
| 2022/0378448 A1 | 12/2022 | Culbert et al. |
| 2022/0378451 A1 | 12/2022 | Goyal et al. |
| 2022/0378460 A1 | 12/2022 | Culbert et al. |
| 2022/0387072 A1 | 12/2022 | Look et al. |
| 2023/0015259 A1 | 1/2023 | Buck et al. |
| 2023/0046775 A1 | 2/2023 | Quick |
| 2023/0047682 A1 | 2/2023 | Deaton et al. |
| 2023/0052964 A1 | 2/2023 | Singh et al. |
| 2023/0059721 A1 | 2/2023 | Chou et al. |

(56) References Cited

U.S. PATENT DOCUMENTS

| | | | |
|---|---|---|---|
| 2023/0062809 A1 | 3/2023 | Merritt et al. |
| 2023/0070120 A1 | 3/2023 | Cox et al. |
| 2023/0122587 A1 | 4/2023 | Chou et al. |
| 2023/0149034 A1 | 5/2023 | Aklog et al. |
| 2023/0200970 A1 | 6/2023 | Merritt et al. |
| 2023/0210554 A1 | 7/2023 | Bruzzi et al. |
| 2023/0218310 A1 | 7/2023 | Scheinblum et al. |
| 2023/0218313 A1 | 7/2023 | Rosenbluth et al. |
| 2023/0218383 A1 | 7/2023 | Merritt et al. |
| 2023/0233311 A1 | 7/2023 | Merritt et al. |
| 2023/0240705 A1 | 8/2023 | Rosenbluth et al. |
| 2023/0240706 A1 | 8/2023 | Rosenbluth et al. |
| 2023/0241302 A1 | 8/2023 | Merritt et al. |
| 2023/0248380 A1 | 8/2023 | Long et al. |
| 2023/0248498 A1 | 8/2023 | Buck et al. |
| 2023/0248499 A1 | 8/2023 | Buck et al. |
| 2023/0248500 A1 | 8/2023 | Buck et al. |
| 2023/0248501 A1 | 8/2023 | Buck et al. |
| 2023/0248502 A1 | 8/2023 | Buck et al. |
| 2023/0248503 A1 | 8/2023 | Buck et al. |
| 2023/0248504 A1 | 8/2023 | Buck et al. |
| 2023/0270991 A1 | 8/2023 | Merritt et al. |
| 2023/0310137 A1 | 10/2023 | Merritt et al. |
| 2023/0310138 A1 | 10/2023 | Merritt et al. |
| 2023/0310751 A1 | 10/2023 | Merritt et al. |
| 2023/0320834 A1 | 10/2023 | Merritt et al. |
| 2023/0329734 A1 | 10/2023 | Marchand et al. |
| 2023/0338130 A1 | 10/2023 | Merritt et al. |
| 2023/0338131 A1 | 10/2023 | Merritt et al. |
| 2023/0355256 A1 | 11/2023 | Dinh |
| 2023/0355259 A1 | 11/2023 | Marchand et al. |
| 2023/0355371 A1 | 11/2023 | Buck et al. |
| 2023/0355938 A1 | 11/2023 | Merritt et al. |
| 2023/0363776 A1 | 11/2023 | Quick |
| 2023/0363883 A1 | 11/2023 | Merritt et al. |
| 2023/0389932 A1 | 12/2023 | Ozenne et al. |
| 2023/0390045 A1 | 12/2023 | Merritt et al. |
| 2024/0016505 A1 | 1/2024 | Horowitz et al. |
| 2024/0016993 A1 | 1/2024 | Haslam et al. |
| 2024/0058113 A1 | 2/2024 | Strauss et al. |
| 2024/0082540 A1 | 3/2024 | Brodt et al. |
| 2024/0108366 A1 | 4/2024 | Horowitz et al. |
| 2024/0131235 A1 | 4/2024 | Horowitz et al. |
| 2024/0157041 A1 | 5/2024 | Zikry et al. |
| 2024/0173042 A1 | 5/2024 | Yang et al. |
| 2024/0198072 A1 | 6/2024 | Merritt et al. |
| 2024/0207593 A1 | 6/2024 | Merritt et al. |
| 2024/0225674 A1 | 7/2024 | Dederich et al. |
| 2024/0245501 A1 | 7/2024 | Strauss et al. |
| 2024/0245502 A1 | 7/2024 | Merritt et al. |
| 2024/0261492 A1 | 8/2024 | Yang et al. |
| 2024/0285387 A1 | 8/2024 | Merritt et al. |
| 2024/0299053 A1 | 9/2024 | Hauser |
| 2024/0307082 A1 | 9/2024 | Marchand et al. |
| 2024/0307166 A1 | 9/2024 | Merritt et al. |
| 2024/0341779 A1 | 10/2024 | Dinh |
| 2024/0341788 A1 | 10/2024 | Cox et al. |

FOREIGN PATENT DOCUMENTS

| | | |
|---|---|---|
| CN | 102316809 | 1/2012 |
| CN | 103764049 | 4/2014 |
| CN | 103932756 | 7/2014 |
| CN | 104068910 | 10/2014 |
| CN | 106178227 | 12/2016 |
| CN | 106470728 | 3/2017 |
| CN | 108348319 | 7/2018 |
| CN | 110312481 | 10/2019 |
| CN | 110652645 | 1/2020 |
| CN | 111281482 | 6/2020 |
| DE | 1116001 | 10/1961 |
| DE | 102017004383 | 7/2018 |
| EP | 0914807 | 5/1999 |
| EP | 1254634 | 11/2002 |
| EP | 1991138 | 11/2008 |
| EP | 2073864 | 7/2009 |
| EP | 2203209 | 7/2010 |
| EP | 2209509 | 7/2010 |
| EP | 2394680 A1 | 12/2011 |
| EP | 1867290 | 2/2013 |
| EP | 2624905 | 8/2013 |
| EP | 2540328 A1 | 10/2013 |
| EP | 2726135 | 5/2014 |
| EP | 2908783 | 8/2015 |
| EP | 2939704 | 11/2015 |
| EP | 2942624 | 11/2015 |
| EP | 2967614 | 1/2016 |
| EP | 2977072 | 1/2016 |
| EP | 2367482 | 10/2016 |
| EP | 3102274 | 12/2016 |
| EP | 3122412 | 2/2017 |
| EP | 3202340 | 8/2017 |
| EP | 3302624 | 4/2018 |
| EP | 3305220 | 4/2018 |
| EP | 3305221 | 4/2018 |
| EP | 3311875 | 4/2018 |
| EP | 2231256 B1 | 5/2018 |
| EP | 3344157 | 7/2018 |
| EP | 3417893 | 12/2018 |
| EP | 3419528 | 1/2019 |
| EP | 3422963 | 1/2019 |
| EP | 3439561 | 2/2019 |
| EP | 3449967 | 3/2019 |
| EP | 3544528 | 10/2019 |
| EP | 3583972 | 12/2019 |
| EP | 3589348 | 1/2020 |
| EP | 3603690 | 2/2020 |
| EP | 3612264 | 2/2020 |
| EP | 3620204 | 3/2020 |
| EP | 3013404 | 4/2020 |
| EP | 4039205 | 8/2022 |
| EP | 4072613 | 10/2022 |
| EP | 4076611 | 10/2022 |
| EP | 4079344 | 10/2022 |
| EP | 4137070 | 2/2023 |
| EP | 4144310 | 3/2023 |
| EP | 4252992 | 10/2023 |
| EP | 4419159 | 8/2024 |
| GB | 1588072 | 4/1981 |
| GB | 2498349 | 7/2013 |
| JP | H6190049 | 7/1994 |
| JP | H07323090 A | 12/1995 |
| JP | 2001522631 | 5/1999 |
| JP | 2000175925 | 6/2000 |
| JP | 2004097807 | 4/2004 |
| JP | 2005511989 | 4/2005 |
| JP | 2005-095242 | 6/2005 |
| JP | 2005230132 | 9/2005 |
| JP | 2005323702 | 11/2005 |
| JP | 2006094876 | 4/2006 |
| JP | 2007-222658 | 9/2007 |
| JP | 2011526820 | 1/2010 |
| JP | 2011517424 | 6/2011 |
| JP | 05694718 B2 | 4/2015 |
| JP | 2015208685 | 11/2015 |
| JP | 2016513505 | 5/2016 |
| JP | 2016104212 | 6/2016 |
| JP | 2017533051 | 11/2017 |
| JP | 2018525088 | 9/2018 |
| JP | 2003033359 | 2/2023 |
| JP | 7253376 | 3/2023 |
| JP | 7324264 | 8/2023 |
| JP | 7491974 | 5/2024 |
| WO | WO1997017889 | 5/1997 |
| WO | WO9833443 | 8/1998 |
| WO | WO9838920 | 9/1998 |
| WO | WO9839053 | 9/1998 |
| WO | WO9851237 | 11/1998 |
| WO | WO1999044542 | 9/1999 |
| WO | WO0032118 | 6/2000 |
| WO | WO2000053120 | 9/2000 |
| WO | WO0202162 | 1/2002 |
| WO | WO2002055146 | 7/2002 |
| WO | WO03015840 | 2/2003 |

(56) References Cited

FOREIGN PATENT DOCUMENTS

| | | |
|---|---|---|
| WO | WO2004018916 | 3/2004 |
| WO | WO2004093696 | 11/2004 |
| WO | WO2005046736 | 5/2005 |
| WO | WO2006029270 | 3/2006 |
| WO | WO2006110186 | 10/2006 |
| WO | WO2006124307 | 11/2006 |
| WO | WO2007092820 | 8/2007 |
| WO | WO2009082513 | 7/2009 |
| WO | WO2009086482 | 7/2009 |
| WO | WO2009126747 | 10/2009 |
| WO | WO2009155571 | 12/2009 |
| WO | WO2010002549 | 1/2010 |
| WO | WO2010010545 | 1/2010 |
| WO | WO2010023671 | 3/2010 |
| WO | WO2010049121 | 5/2010 |
| WO | WO2010095712 | 8/2010 |
| WO | WO2010102307 | 9/2010 |
| WO | WO2011032712 | 3/2011 |
| WO | WO2011054531 | 5/2011 |
| WO | WO2011073176 | 6/2011 |
| WO | WO2012009675 | 1/2012 |
| WO | WO2012011097 | 1/2012 |
| WO | WO2012049652 | 4/2012 |
| WO | WO2012065748 | 5/2012 |
| WO | WO2012114633 | 8/2012 |
| WO | WO2012120490 | 9/2012 |
| WO | WO2012162437 | 11/2012 |
| WO | WO2014047650 | 3/2014 |
| WO | WO2014081892 | 5/2014 |
| WO | WO2014139845 | 9/2014 |
| WO | WO2015006782 | 1/2015 |
| WO | WO2015061365 | 4/2015 |
| WO | WO2015121424 | 8/2015 |
| WO | WO2015179329 | 11/2015 |
| WO | WO2015189354 | 12/2015 |
| WO | WO2015191646 | 12/2015 |
| WO | WO2016014955 | 1/2016 |
| WO | WO2016071524 | 5/2016 |
| WO | WO2017024258 | 2/2017 |
| WO | WO2017033182 | 3/2017 |
| WO | WO2017058280 | 4/2017 |
| WO | WO2017070702 | 4/2017 |
| WO | WO2017106877 | 6/2017 |
| WO | WO2017189535 | 11/2017 |
| WO | WO2017189550 | 11/2017 |
| WO | WO2017189591 | 11/2017 |
| WO | WO2017189615 | 11/2017 |
| WO | WO2017210487 | 12/2017 |
| WO | WO2018019829 | 2/2018 |
| WO | WO2018049317 | 3/2018 |
| WO | WO2018065092 | 4/2018 |
| WO | WO2018080590 | 5/2018 |
| WO | WO2018148174 | 8/2018 |
| WO | WO2019010318 | 1/2019 |
| WO | WO2019050765 | 3/2019 |
| WO | WO2019064306 | 4/2019 |
| WO | WO2019075444 | 4/2019 |
| WO | WO2019094456 | 5/2019 |
| WO | WO2019173475 | 9/2019 |
| WO | WO2019222117 | 11/2019 |
| WO | WO2019246240 | 12/2019 |
| WO | WO2020036809 | 2/2020 |
| WO | WO2020142381 | 7/2020 |
| WO | WO2021067134 | 4/2021 |
| WO | WO2021076954 | 4/2021 |
| WO | WO2021127202 | 6/2021 |
| WO | WO2021248042 | 12/2021 |
| WO | WO2022032173 | 2/2022 |
| WO | WO2022103848 | 5/2022 |
| WO | WO2022109021 | 5/2022 |
| WO | WO2022109034 | 5/2022 |
| WO | WO2023018819 | 2/2023 |
| WO | 2023069874 A1 | 4/2023 |
| WO | WO2003048616 | 6/2023 |
| WO | WO2023115032 | 6/2023 |
| WO | WO2023137341 | 7/2023 |
| WO | WO2023147353 | 8/2023 |
| WO | WO2023154612 | 8/2023 |
| WO | WO2023192925 | 10/2023 |
| WO | WO2023215779 | 11/2023 |
| WO | WO2024103036 | 5/2024 |
| WO | WO2024151629 | 7/2024 |

OTHER PUBLICATIONS

US 12,115,056 B2, 10/2024, Merritt et al. (withdrawn)
Gibbs, et al., "Temporary Stent as a bail-out device during percutaneous transluminal coronary angioplasty: preliminary clinical experience," British Heart Journal, 1994, 71:372-377, Oct. 12, 1993, 6 pgs.
Gupta, S. et al., "Acute Pulmonary Embolism Advances in Treatment", JAPI, Association of Physicians India, Mar. 2008, vol. 56, 185-191.
International Search Report and Written Opinion for International App. No. PCT/US13/61470, mailed Jan. 17, 2014, 7 pages.
International Search Report and Written Opinion for International App. No. PCT/US2014/046567, mailed Nov. 3, 2014, 13 pages.
International Search Report and Written Opinion for International App. No. PCT/US2014/061645, mailed Jan. 23, 2015, 15 pages.
International Search Report for International App. No. PCT/US13/71101, mailed Mar. 31, 2014, 4 pages.
Konstantinides, S. et al., "Pulmonary embolism hotline 2012—Recent and expected trials", Thrombosis and Haemostasis, Jan. 9, 2013:33; 43-50.
Konstantinides, S. et al., "Pulmonary embolism: risk assessment and management", European Society of Cardiology; European Heart Journal, Sep. 7, 2012:33, 3014-3022.
Kucher, N. et al., "Percutaneous Catheter Thrombectomy Device for Acute Pulmonary Embolism: In Vitro and in Vivo Testing", Circulation, Sep. 2005:112:e28-e32.
Kucher, N., "Catheter Interventions in Massive Pulmonary Embolism", Cardiology Rounds, Mar. 2006 vol. 10, Issue 3, 6 pages.
Kucher, N. et al., "Management of Massive Pulmonary Embolism", Radiology, Sep. 2005:236:3 852-858.
Kucher, N. et al., "Randomized, Controlled Trial of Ultrasound-Assisted Catheter-Directed Thrombolysis for Acute Intermediate-Risk Pulmonary Embolism." Circulation, 2014, 129, pages 9 pages.
Kuo, W. et al., "Catheter-directed Therapy for the Treatment of Massive Pulmonary Embolism: Systematic Review and Meta-analysis of Modern Techniques", Journal of Vascular and Interventional Radiology, Nov. 2009:20:1431-1440.
Kuo, W. et al., "Catheter-Directed Embolectomy, Fragmentation, and Thrombolysis for the Treatment of Massive Pulmonary Embolism After Failure of Systemnic Thrombolysis", American College of CHEST Physicians 2008: 134:250-254.
Kuo, W. MD, "Endovascular Therapy for Acute Pulmonary Embolism", Continuing Medical Education Society of Interventional Radiology ("CME"); Journal of Vascular and Interventional Radiology, Feb. 2012: 23:167-179.
Lee, L. et al., "Massive pulmonary embolism: review of management strategies with a focus on catheter-based techniques", Expert Rev. Cardiovasc. Ther. 8(6), 863-873 (2010).
Liu, S. et al., "Massive Pulmonary Embolism: Treatment with the Rotarex Thrombectomy System", Cardiovascular Interventional Radiology; 2011: 34:106-113.
Muller-Hulsbeck, S. et al. "Mechanical Thrombectomy of Major and Massive Pulmonary Embolism with Use of the Amplatz Thrombectomy Device", Investigative Radiology, Jun. 2001:36:6:317-322.
Reekers, J. et al., "Mechanical Thrombectomy for Early Treatment of Massive Pulmonary Embolism", CardioVascular and Interventional Radiology, 2003: 26:246-250.
Schmitz-Rode et al., "New Mesh Basket for Percutaneous Removal of Wall-Adherent Thrombi in Dialysis Shunts," Cardiovasc Intervent Radiol 16:7-10 1993 4 pgs.
Schmitz-Rode et al., "Temporary Pulmonary Stent Placement as Emergency Treatment of Pulmonary Embolism," Journal of the American College of Cardiology, vol. 48, No. 4, 2006 (5 pgs.).

(56) References Cited

OTHER PUBLICATIONS

Schmitz-Rode, T. et al., "Massive Pulmonary Embolism: Percutaneous Emergency Treatment by Pigtail Rotation Catheter", JACC Journal of the American College of Cardiology, Aug. 2000:36:2:375-380.
Spiotta, A et al., "Evolution of thrombectomy approaches and devices for acute stroke: a technical review." J Neurointervent Surg 2015, 7, p. 7 p.
Svilaas, T. et al., "Thrombus Aspiration During Primary Percutaneous Coronary Intervention." The New England Journal of Medicine, 2008, vol. 358, No. 6, 11 pages.
Tapson, V., "Acute Pulmonary Embolism", The New England Journal of Medicine, Mar. 6, 2008:358:2037-52.
The Penumbra Pivotal Stroke Trial Investigators, "The Penumbra Pivotal Stroke Trial: Safety and Effectiveness of a New Generation of Mechanical Devices for Clot Removal in Intracranial Large Vessel Occlusive Disease." Stroke, 2009, 40: p. 9 pages.
Truong et al., "Mechanical Thrombectomy of Iliocaval Thrombosis Using a Protective Expandable Sheath," Cardiovasc Intervent Radiol27-254-258, 2004, 5 pgs.
Turk et al., "ADAPT FAST study: a direct aspiration first pass technique for acute stroke thrombectomy." J Neurointervent Surg, vol. 6, 2014, 6 pages.a
Uflacker, R., "Interventional Therapy for Pulmonary Embolism", Journal of Vascular and Interventional Radiology, Feb. 2001: 12:147-164.
Verma, R., MD et al. "Evaluation of a Newly Developed Percutaneous Thrombectomy Basket Device in Sheep With Central Pulmonary Embolisms", Investigative Radiology, Oct. 2006, 41, 729-734.
International Search Report and Written Opinion for International App. No. PCT/US2015/034987 filed Jun. 9, 2015, Applicant: Inceptus Medical, LLC, Date of Mailing: Sep. 17, 2015, 12 pages.
International Search Report and Written Opinion for International App. No. PCT/US2016/067628 filed Dec. 19, 2016, Applicant: Inari Medical, Inc., Date of Mailing: Apr. 10, 2017, 11 pages.
Goldhaber, S. et al. "Percutaneous Mechanical Thrombectomy for Acute Pulmonary Embolism—A Double-Edged Sword," American College of CHEST Physicians, Aug. 2007, 132:2, 363-372.
Goldhaber, S., "Advanced treatment strategies for acute pulmonary embolism, including thrombolysis and embolectomy," Journal of Thrombosis and Haemostasis, 2009: 7 (Suppl. 1): 322-327.
International Search Report and Written Opinion for International App. No. PCT/US2017/029696, Date of Filing: Apr. 26, 2017, Applicant: Inari Medical, Inc., Date of Mailing: Sep. 15, 2017, 19 pages.
International Search Report and Written Opinion for International App. No. PCT/US2016/058536, Date of Filing: Oct. 24, 2016, Applicant: Inari Medical, Inc., Date of Mailing: Mar. 13, 2017, 14 pages.
International Search Report and Written Opinion for International App. No. PCT/US2018/048786, Date of Filing: Aug. 30, 2018, Applicant: Inari Medical, Inc., Date of Mailing: Dec. 13, 2018, 12 pages.
International Search Report and Written Opinion for International App. No. PCT/US2018/055780, Date of Filing: Oct. 13, 2018, Applicant: Inceptus Medical LLC., Date of Mailing: Jan. 22, 2019, 8 pages.
International Search Report and Written Opinion for International App. No. PCT/US2019/045794, Date of Filing: Aug. 8, 2019, Applicant: Inari Medical, Inc., Date of Mailing: Nov. 1, 2019, 17 pages.
International Search Report and Written Opinion for International App. No. PCT/US2020/056067, Date of Filing: Oct. 16, 2020, Applicant: Inari Medical, Inc., Date of Mailing: Jan. 22, 2021, 8 pages.
International Search Report and Written Opinion for International App. No. PCT/US2020/055645, Date of Filing: Dec. 17, 2020; Applicant: Inari Medical, Inc., Date of Mailing: Apr. 14, 2021, 12 pages.

Vorwerk, D. MD, et al., "Use of a Temporary Caval Filter to Assist Percutaneous Iliocaval Thrombectomy: Experimental Results." SCVIR, 1995, 4 pages.
WIKIPEDIA; Embolectomy; retrieved from the internet: https://en.wikipedia.org/wiki/Embolectomy; 4 pgs.; retrieved/printed: Mar. 24, 2016.
O'Sullivan; Thrombolysis versus thrombectomy in acute deep vein thrombosis; Interventional Cardiology; 3(5); pp. 589-596; Oct. 2011.
Capture Vascular Systems; (company website); retrieved from the internet: http://www.capturevascular.com; 3 pgs.; retrieved/printed: Mar. 24, 2016.
Edwards Lifesciences; Fogarty® Occlusion Catheters (product brochure); retrieved from the internet: http://web.archive.org/web/20150228193218/http://www.edwards.com/products/vascular/atraumaticocclusion/pages/occlusioncatheter.aspx; ©2011; 2 pgs .; retrieved/printed: Mar. 24, 2011.
Boston Scientific; Fetch(TM) 2 Aspiration Catheter (product information);retrieved from the internet: http://www.bostonscientific.com/en-US/products/thrombectomy-systems/fetch2-aspiration-catheter.html; 2 pgs.; retrieved/printed: Mar. 24, 2016.
Penumbra, Inc.; Indigo® System (product information); retrieved from the internet: http://www.penumbrainc.com/peripherallpercutaneous-thromboembolectomy/indigo-system; 7 pgs.; retrieved/printed: Mar. 24, 2016.
YOUTUBE; Merci Retrieval System X Series Animation; uploaded Mar. 16, 2009 (product information): posted on May 7, 2009 by SSMDePAUL, time 1:09, retrieved from the internet: https://www.youtube.com/watch?v=MGX7deuFkhc; 3 pgs.; retrieved/printed: Mar. 24, 2016.
COVIDIEN; Solitaire(TM) AS Neurovascular Remodeling Device (product information); retrieved from the internet: http://www.ev3.net/neuro/intl/remodeling-devices/solitaire-ab. htm; ©2015; 2 pgs.; retrieved/printed: Mar. 24, 2016.
International Search Report and Written Opinion for International App. No. PCT/US21/35965, Date of Filing: Jun. 4, 2021, Applicant: Inari Medical, Inc., Date of Mailing: Sep. 28, 2021, 12 pages.
International Search Report and Written Opinion for International App. No. PCT/US21/45072 Date of Filing: Aug. 6, 2021, Applicant: Inari Medical, Inc., Date of Mailing: Jan. 20, 2022, 10 pages.
International Search Report and Written Opinion for International App. No. PCT/US21/58793; Date of Filing: Nov. 10, 2021, Applicant: Inari Medical, Inc., Date of Mailing: Mar. 16, 2022, 13 pages.
International Search Report and Written Opinion for International App. No. PCT/US21/59718; Date of Filling: Nov. 17, 2021, Applicant: Inari Medical, Inc., Date of Mailing: Mar. 22, 2022, 13 pages.
International Search Report and Written Opinion for International App. No. PCT/US21/59735; Date of Filing: Nov. 17, 2021, Applicant: Inari Medical, Inc., Date of Mailing: Mar. 22, 2022, 11 pages.
International Search Report and Written Opinion for International App. No. PCT/US23/60502; Date of Filing: Jan. 11, 2023, Applicant: Inari Medical, Inc., Date of Mailing: May 25, 2023, 9 pages.
International Search Report and Written Opinion for International App. No. PCT/US23/61256; Date of Filing: Jan. 25, 2023, Applicant: Inari Medical, Inc., Date of Mailing: Jun. 7, 2023, 8 pages.
Gross et al., "Dump the pump: manual aspiration thrombectomy (MAT) with a syringe is technically effective, expeditious, and cost-efficient," J NeuroIntervent Surg, 2018, 4 pages.
English translation of Japanese Office Action mailed Jun. 7, 2023 for Japanese Application No. 2021-507564, 7 pages.
European Office Action received for EP Application No. 16876941.2, Applicant: Inari Medical, Inc, Date of Mailing: Jul. 18, 2023, 6 pages.
International Search Report and Written Opinion for International App. No. PCT/US23/60927; Date of Filing: Jan. 19, 2023, Applicant: Inari Medical, Inc., Date of Mailing: Jul. 20, 2023, 12 pages.
Extended European Search Report issued for EP Application No. 20877370.5, Date of Mailing: Oct. 17, 2023. 11 pages.
International Search Report and Written Opinion for International App. No. PCT/US23/65128; Date of Filing: Mar. 30, 2023, Applicant: Inari Medical, Inc., Date of Mailing: Nov. 14, 2023, 14 pages.

(56) References Cited

OTHER PUBLICATIONS

International Search Report and Written Opinion for International App. No. PCT/US23/66538; Date of Filing: May 3, 2023, Applicant: Inari Medical, Inc., Date of Mailing: Jan. 4, 2024, 14 pages.
English translation of Japanese Office Action received for JP Application No. 2022-574456, Applicant: Inari Medical, Inc, Date of Mailing: Jan. 23, 2024, 12 pages.
Chinese First Office Action received for CN Application No. 201980067623.1, Applicant: Inari Medical, Inc., Date of Mailing: Jan. 31, 2024, 10 pages.
International Search Report and Written Opinion for International App. No. PCT/US23/73765; Date of Filing: Sep. 8, 2023, Applicant: Inari Medical, Inc., Date of Mailing: Feb. 28, 2024, 7 pages.
International Search Report and Written Opinion for International App. No. PCT/US23/69892; Date of Filing: Jul. 10, 2023, Applicant: Inari Medical, Inc., Date of Mailing: Feb. 29, 2024, 12 pages.
English translation of Japanese Office Action mailed Jan. 19, 2024 for Japanese Application No. 2022-160947, 8 pages.
International Search Report and Written Opinion for International App. No. PCT/US2024/010875; Applicant: Inari Medical, Inc., Date of Mailing: Apr. 26, 2024, 15 pages.
International Search Report and Written Opinion for International App. No. PCT/US2023/079428; Applicant: Inari Medical, Inc., Date of Mailing: May 29, 2024, 18 pages.
Extended European Search Report for European Application No. 21818772.2, Applicant: Inari Medical, Inc., Date of Mailing: May 10, 9 pages.
Chinese Office Action received for Application No. 202111061740.2, Applicant: Inari Medical, Inc, Date of Mailing: May 23, 2024, 15 pages.
English translation of Japanese Office Action mailed Jun. 25, 2024 for Japanese Application No. 2022-574456, 5 pages.
Japanese Office Action mailed Jul. 8, 2024 for Japanese Application No. 2022-522892, 14 pages.
Chinese first Office Action mailed May 10, 2024 for Chinese Application No. 202080087833.X, 11 pages.
Partial Supplementary European Search Report received for European Application No. 21852966.7; Applicant: Inari Medical, Inc., Date of Mailing: Jul. 23, 2024, 12 pages.
Japanese Office Action mailed Aug. 2, 2024 for Japanese Application No. 2023-213724, 3 pages.
English Translation of Japanese Office Action mailed Jul. 23, 2024 for Japanese Application No. 2022-535535, 11 pages.
English machine translation of Japanese Office Action mailed Oct. 10, 2024 for Japanese Application No. 2022-522892, 11 pages.
Extended European Search Report received for European Application No. 21895504.5; Applicant: Inari Medical, Inc., Date of Mailing: Aug. 16, 2024, 10 pages.
Shani, Jacob M.D., et al., "Mechanical Manipulation of Thrombus: Coronary Thrombectomy," Intracoronary Clot Displacement, and Transcatheter Aspiration, 72 Am. J. Cardiol. 116G-118G, 1993, 3 pages.
Bose, A., et al., "The Penumbra System: A Mechanical Device for the Treatment of Acute Stroke due to Thromboembolism," 29 Am. J. Neuroradiol. 1409-1413, Aug. 2008, 6 pages.
Turk, Aquilla S., et al., "Initial clinical experience with the ADAPT technique: A direct aspiration first pass technique for stroke thrombectomy," 6 J. NeuroIntervent. Surg. 231-237, 2014, 8 pages.
Turk, Aquilla S., et al., "Aspiration thrombectomy versus stent retriever thrombectomy as first-line approach for large vessel occlusion (COMPASS): a multicentre, randomized, open label, blinded outcome, non-inferiority trial," 393 Lancet 998-1008, Mar. 2019, 11 pages.
Saver, Jeffrey L., "Time is Brain-Quantified," Stroke Center and Department of Neurology, University of California, Los Angeles, 2005, https://www.ahajournals.org/doi/10.1161/01.str.0000196957.55928.ab, 4 pages.
Petition for Inter Partes Review of U.S. Pat. No. 11,744,691, *Imperative Care, Inc.* (Petitioner) V. *Inari Medical, Inc.* (Patent Owner), Case IPR2024-01257, 103 pages.
Declaration of Troy L. Thornton in Support of Petition for Inter Partes Review of U.S. Pat. No. 11,744,691, *Imperative Care, Inc.* (Petitioner) V. *Inari Medical, Inc.* (Patent Owner), Case IPR2024-01257, filed with IPR as exhibit on Aug. 12, 2024, 114 pages.
Expert Declaration of Aquilla S. Turk, III, D.O. in Support of Petition for Inter Partes Review of U.S. Pat. No. 11,744,691, *Imperative Care, Inc.* (Petitioner) V. *Inari Medical, Inc.* (Patent Owner), Case IPR2024-01257, filed with IPR as exhibit on Aug. 12, 2024, 24 pages.
Declaration of Troy L. Thornton in Support of Petition for Inter Partes Review of U.S. Pat. No. 11,697,011, *Imperative Care, Inc.* (Petitioner) V. *Inari Medical, Inc.* (Patent Owner), Case IPR2024-01257, executed on Jul. 8, 2024, filed with IPR as exhibit on Aug. 12, 2024, 138 pages.
Petition for Inter Partes Review of U.S. Pat. No. 11,697,011, Before the Patent Trial and Appeal Board, *Imperative Care, Inc.* (Petitioner) V. *Inari Medical, Inc.* (Patent Owner), Case IPR2024-01257, executed on Jul. 8, 2024, filed with IPR as exhibit on Aug. 12, 2024, 97 pages.
Defendant Imperative Care's Opposition To Plaintiff Inari Medical's Motion for a Preliminary Injunction, in the United States District Court for the Northern District of California San Jose Division, *Inari Medical, Inc.* (Plaintiff) V. *Imperative Care, Inc.* (Defendants), Civil Action No. 5:24-cv-03117-EKL, filed on Sep. 9, 2024, 44 pages.
Declaration of Troy Thornton in Support of Opposition To Plaintiff's Motion for Preliminary Injunction, in the United States District Court for the Northern District of California San Jose Division, *Inari Medical, Inc.* (Plaintiff) V. *Imperative Care, Inc.* (Defendants), Civil Action No. 5:24-cv-03117-EKL, filed on Sep. 9, 2024, 74 pages.
English translation of Japanese Office Action mailed Sep. 17, 2024 for Japanese Application No. 2023-203650, 6 pages.

* cited by examiner

SINGLE INSERTION DELIVERY SYSTEM FOR TREATING EMBOLISM AND ASSOCIATED SYSTEMS AND METHODS

CROSS-REFERENCE TO RELATED APPLICATION

This application is a continuation of U.S. patent application Ser. No. 17/865,307, filed on Jul. 14, 2022, and titled "SINGLE INSERTION DELIVERY SYSTEM FOR TREATING EMBOLISM AND ASSOCIATED SYSTEMS AND METHODS," which is a continuation of U.S. patent application Ser. No. 17/498,642, filed on Oct. 11, 2021, and titled "SINGLE INSERTION DELIVERY SYSTEM FOR TREATING EMBOLISM AND ASSOCIATED SYSTEMS AND METHODS," which is a continuation of U.S. patent application Ser. No. 16/258,344, filed on Jan. 25, 2019, and titled "SINGLE INSERTION DELIVERY SYSTEM FOR TREATING EMBOLISM AND ASSOCIATED SYSTEMS AND METHODS," which is now issued as U.S. Pat. No. 11,154,314, which claims the benefit of U.S. Provisional Patent Application No. 62/622,691, filed on Jan. 26, 2018, and titled "SINGLE INSERTION DELIVERY SYSTEM FOR TREATING EMBOLISM AND ASSOCIATED SYSTEMS AND METHODS," which are incorporated herein by reference in their entireties.

TECHNICAL FIELD

The present technology relates generally to devices and methods for the intravascular treatment of emboli and/or thrombi within a blood vessel of a human patient. In particular, some embodiments of the present technology relate to systems for repeatedly deploying an interventional device at or proximate to a pulmonary embolism within a patient.

BACKGROUND

Thromboembolic events are characterized by an occlusion of a blood vessel. Thromboembolic disorders, such as stroke, pulmonary embolism, heart attack, peripheral thrombosis, atherosclerosis, and the like, affect many people. These disorders are a major cause of morbidity and mortality.

When an artery is occluded by a clot, tissue ischemia develops. The ischemia will progress to tissue infarction if the occlusion persists. Infarction does not develop or is greatly limited if the flow of blood is reestablished rapidly. Failure to reestablish blood flow can lead to the loss of limb, angina pectoris, myocardial infarction, stroke, or even death.

In the venous circulation, occlusive material can also cause serious harm. Blood clots can develop in the large veins of the legs and pelvis, a common condition known as deep venous thrombosis (DVT). DVT arises most commonly when there is a propensity for stagnated blood (e.g., long distance air travel, immobility, etc.) and clotting (e.g., cancer, recent surgery, such as orthopedic surgery, etc.). DVT causes harm by: (1) obstructing drainage of venous blood from the legs leading to swelling, ulcers, pain, and infection, and (2) serving as a reservoir for blood clots to travel to other parts of the body including the heart, lungs, brain (stroke), abdominal organs, and/or extremities.

In the pulmonary circulation, the undesirable material can cause harm by obstructing pulmonary arteries—a condition known as pulmonary embolism. If the obstruction is upstream, in the main or large branch pulmonary arteries, it can severely compromise total blood flow within the lungs, and therefore the entire body, and result in low blood pressure and shock. If the obstruction is downstream, in large to medium pulmonary artery branches, it can prevent a significant portion of the lung from participating in the exchange of gases to the blood resulting in low blood oxygen and buildup of blood carbon dioxide.

There are many existing techniques to reestablish blood flow through an occluded vessel. One common surgical technique, an embolectomy, involves incising a blood vessel and introducing a balloon-tipped device (such as the Fogarty catheter) to the location of the occlusion. The balloon is then inflated at a point beyond the clot and used to translate the obstructing material back to the point of incision. The obstructing material is then removed by the surgeon. Although such surgical techniques have been useful, exposing a patient to surgery may be traumatic and best avoided when possible. Additionally, the use of a Fogarty catheter may be problematic due to the possible risk of damaging the interior lining of the vessel as the catheter is being withdrawn.

Percutaneous methods are also utilized for reestablishing blood flow. A common percutaneous technique is referred to as balloon angioplasty where a balloon-tipped catheter is introduced to a blood vessel (e.g., typically through an introducing catheter). The balloon-tipped catheter is then advanced to the point of the occlusion and inflated to dilate the stenosis. Balloon angioplasty is appropriate for treating vessel stenosis, but it is generally not effective for treating acute thromboembolisms as none of the occlusive material is removed and the vessel will re-stenos after dilation. Another percutaneous technique involves placing a catheter near the clot and infusing streptokinase, urokinase, or other thrombolytic agents to dissolve the clot. Unfortunately, thrombolysis typically takes hours to days to be successful. Additionally, thrombolytic agents can cause hemorrhage and in many patients the agents cannot be used at all.

Various devices exist for performing a thrombectomy or removing other foreign material. However, such devices have been found to have structures which are either highly complex, cause trauma to the treatment vessel, or lack sufficient retaining structure and thus cannot be appropriately fixed against the vessel to perform adequately. Furthermore, many of the devices have highly complex structures that lead to manufacturing and quality control difficulties as well as delivery issues when passing through tortuous or small diameter catheters. Less complex devices may allow the user to pull through the clot, particularly with inexperienced users, and such devices may not completely capture and/or collect all of the clot material.

Moreover, with many devices, it is difficult or not possible to make repeated attempts at removing clot material (e.g., to make multiple passes with a device). In particular, if a first pass with a device does not completely capture and/or collect all of the clot material, the device and an accompanying catheter system must be removed from the patient, cleaned, and subsequently reinserted into the patient in order to make a second pass and remove additional material. This can be time consuming and traumatic for the patient.

Thus, there exists a need for an improved embolic extraction device.

BRIEF DESCRIPTION OF THE DRAWINGS

Many aspects of the present technology can be better understood with reference to the following drawings. The components in the drawings are not necessarily to scale.

Instead, emphasis is placed on illustrating clearly the principles of the present disclosure.

DETAILED DESCRIPTION

Figure 1A:
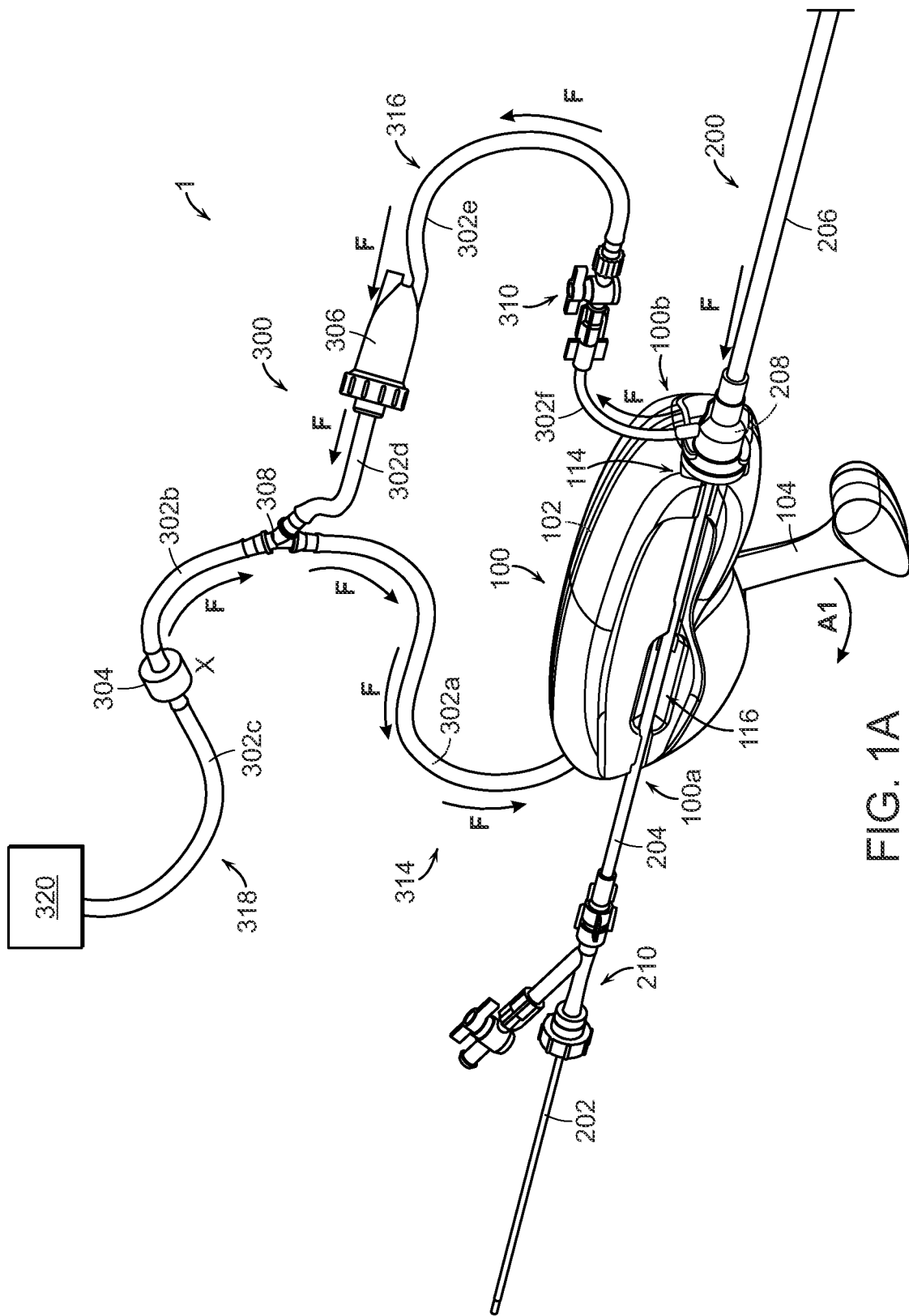
FIGS. 1A and 1B are perspective views of a retraction and aspiration system shown in a first state and a second state, respectively, in accordance with embodiments of the present technology.

The present technology is generally directed to systems and associated devices and methods for engaging and removing clot material from a blood vessel of a human patient. In some embodiments, an interventional device can be advanced through a guide catheter and deployed within clot material in a blood vessel. The interventional device can subsequently be withdrawn from the patient through the guide catheter to remove clot material captured by the interventional device. In some embodiments of the present technology, the interventional device can be repeatedly deployed in/withdrawn from the blood vessel to capture a desired amount of the clot material-without requiring that the guide catheter be fully withdrawn from the patient after each "pass" (e.g., each repeated deployment/withdrawal of the interventional device). That is, the guide catheter may be inserted only a single time during an intravascular procedure including multiple passes to remove clot material from the patient.

Although many of the embodiments are described below with respect to devices, systems, and methods for treating a pulmonary embolism, other applications and other embodiments in addition to those described herein are within the scope of the technology (e.g., intravascular procedures other than the treatment of emboli, intravascular procedures for treating cerebral embolism, etc.). Additionally, several other embodiments of the technology can have different configurations, states, components, or procedures than those described herein. Moreover, it will be appreciated that specific elements, substructures, advantages, uses, and/or other features of the embodiments described with reference to FIGS. 1A-14 can be suitably interchanged, substituted or otherwise configured with one another in accordance with additional embodiments of the present technology. Furthermore, suitable elements of the embodiments described with reference to FIGS. 1A-14 can be used as standalone and/or self-contained devices. A person of ordinary skill in the art, therefore, will accordingly understand that the technology can have other embodiments with additional elements, or the technology can have other embodiments without several of the features shown and described below with reference to FIGS. 1A-14.

With regard to the terms "distal" and "proximal" within this description, unless otherwise specified, the terms can reference a relative position of the portions of a retraction and aspiration apparatus and/or an associated catheter system with reference to an operator and/or a location in the vasculature. Also, as used herein, the designations "rearward," "forward," "upward," "downward," etc. are not meant to limit the referenced component to use in a specific orientation. It will be appreciated that such designations refer to the orientation of the referenced component as illustrated in the Figures; the retraction and aspiration system of the present technology can be used in any orientation suitable to the user.

I. SELECTED EMBODIMENTS OF RETRACTION/ASPIRATION SYSTEMS AND METHODS OF USE

Figure 1B:
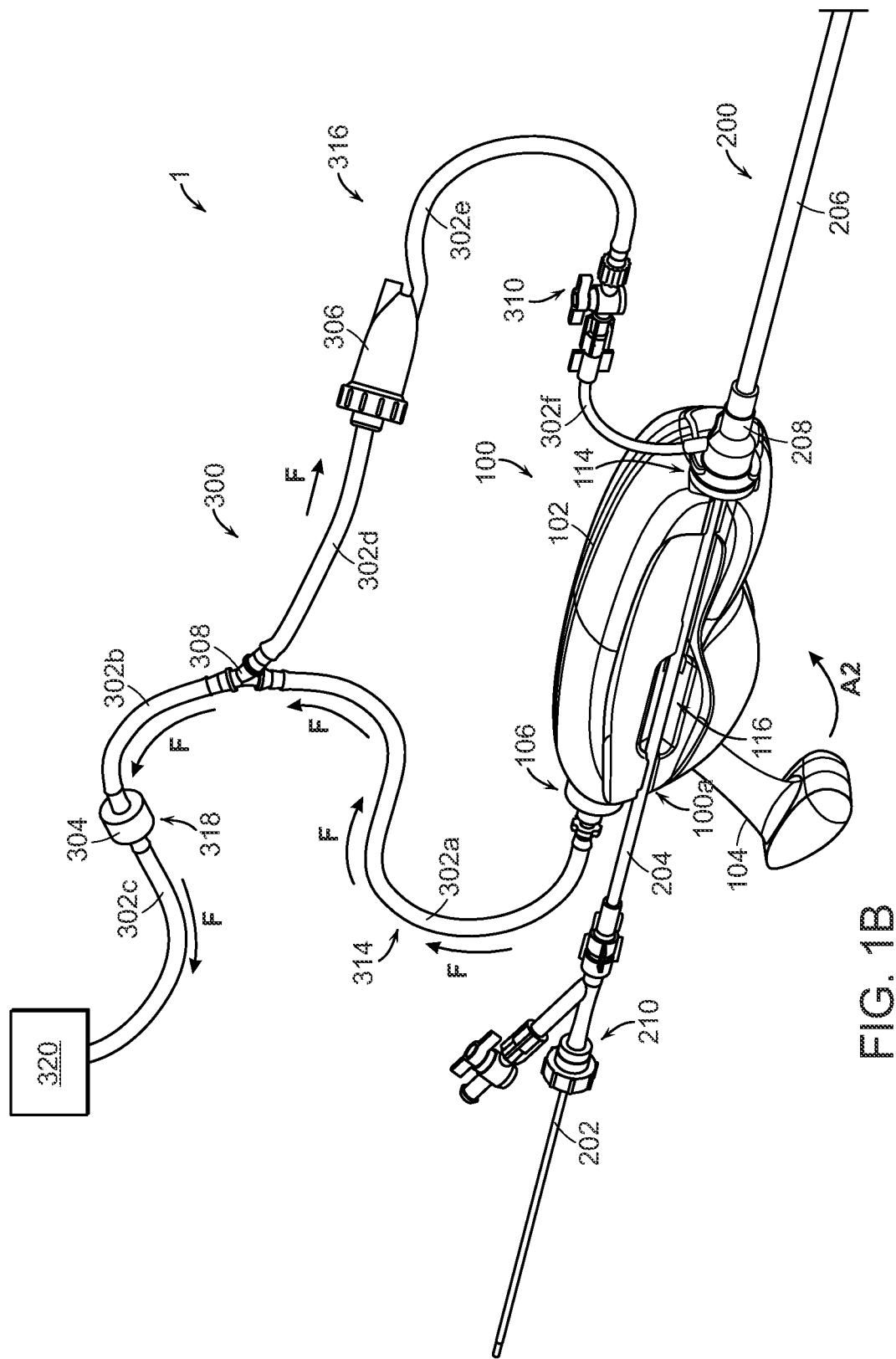

FIGS. 1A and 1B are perspective views of a proximal portion of a clot retrieval system 1 configured in accordance with embodiments of the present technology, shown in a first state and a second state, respectively. Referring to FIGS. 1A and 1B together, the clot retrieval system 1 includes a retraction and aspiration device 100 ("RA device 100"), a catheter system 200, and a tubing system 300. In some embodiments, the RA device 100 is coupleable to the catheter system 200 and operable to simultaneously (i) retract a portion of the catheter system 200 and (ii) aspirate through the catheter system 200. In certain embodiments, the RA device 100 and catheter system 200 can both be fluidly coupled to the tubing system 300 to enable material (e.g., blood and clot material) aspirated from the catheter system 200 to flow into the tubing system 300. In particular, the RA device 100, the catheter system 200, and the tubing system 300 can be the same as or similar to one or more of the retraction and aspiration devices, catheter systems, and tubing systems disclosed in U.S. Pat. No. 9,526,864, filed Jun. 9, 2015, and titled "RETRACTION AND ASPIRATION DEVICE FOR TREATING EMBOLISM AND ASSOCIATED METHODS," which is incorporated herein by reference in its entirety.

FIGS. 2A-2G are schematic illustrations of a distal portion of the clot retrieval system 1 during a clot removal procedure in accordance with embodiments of the present technology. In particular, FIGS. 2A-2G illustrate a distal portion of the catheter system 200 that is positioned proximate to an embolism or clot material within a blood vessel (e.g., a pulmonary blood vessel). Accordingly, operation of the catheter system 200 is described with references to FIGS. 2A-2G.

Figure 2A:
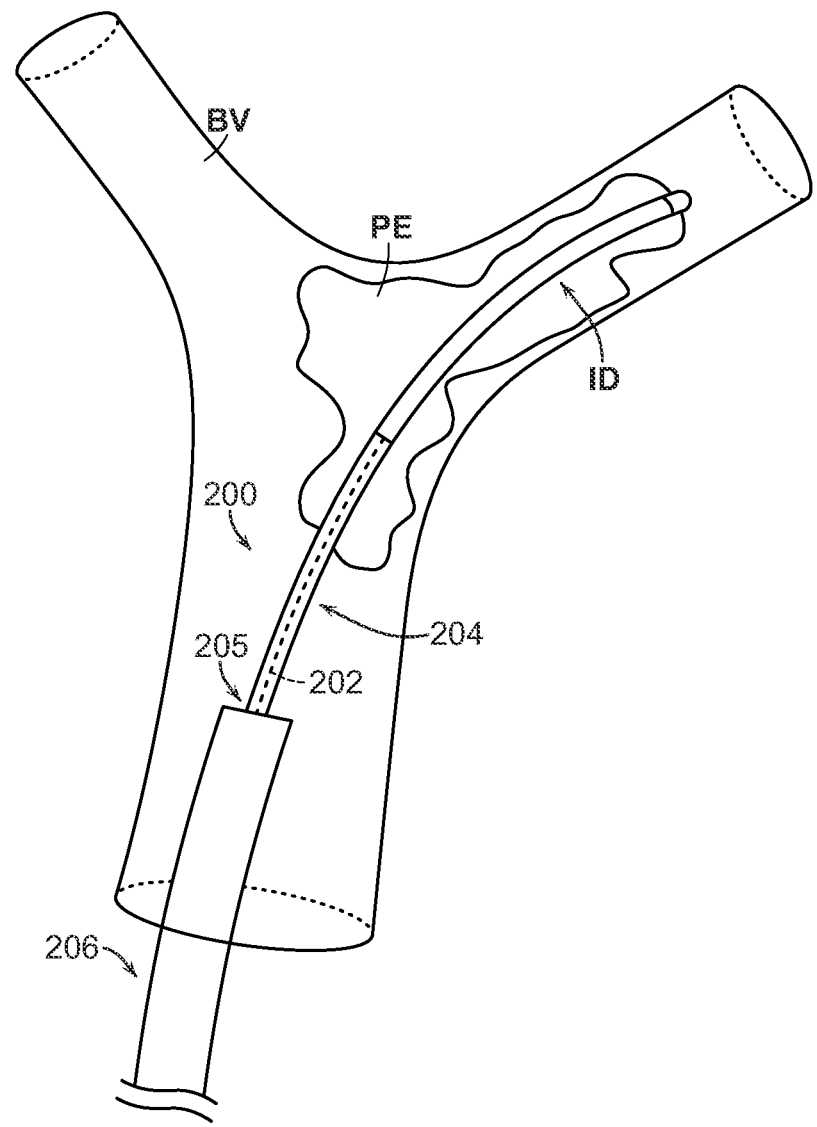
FIGS. 2A-2G are schematic illustrations of a distal portion of the retraction and aspiration system during a clot removal procedure in accordance with embodiments of the present technology.

FIG. 2A is a side view of a distal portion of the catheter system 200 positioned adjacent an embolism or clot material PE within a blood vessel BV (e.g., a pulmonary blood vessel). As shown in FIG. 2A, the catheter system 200 can include an outer guide catheter 206 defining a lumen 205, a delivery sheath 204 slidably received within the lumen of the guide catheter 206, and an elongated pull (and/or push) member 202 slidably received within a lumen of the delivery sheath 204. The guide catheter 206 and the delivery sheath 204 individually comprise an elongated shaft having a lumen and, in some embodiments, the push member 202 can also define a lumen (e.g., configured to receive a guidewire therethrough). In a particular embodiment, the catheter system 200 does not include a guide catheter 206 and/or a delivery sheath 204. As shown in FIG. 2A, a distal portion of the push member 202 can be integral with or coupled to an interventional device ID, such as a clot removal and/or clot treatment device, that is housed within the delivery sheath 204. Accordingly, axial movement of the pull member 202 causes axial movement of the interventional device ID.

As further shown in FIG. 2A, the delivery sheath 204 and the interventional device ID can be positioned at least partially within the clot material PE. Access to the pulmonary vessels can be achieved through the patient's vasculature, for example, via the femoral vein. The catheter system 200 can include an introducer 210 (FIGS. 1A and 1B; e.g., a Y-connector with a hemostasis valve) that can be partially inserted into the femoral vein. A guidewire (not shown) can be guided into the femoral vein through the introducer 210 and navigated through the right atrium, the tricuspid valve, the right ventricle, the pulmonary valve and into the main pulmonary artery. Depending on the location of the embolism, the guidewire can be guided to one or more of the branches of the right pulmonary artery and/or the left pulmonary artery. It will be understood, however, that other access locations into the venous circulatory system of a patient are possible and consistent with the present technology. For example, the user can gain access through the jugular vein, the subclavian vein, the brachial vein or any other vein that connects or eventually leads to the superior vena cava. Use of other vessels that are closer to the right atrium of the patient's heart can also be advantageous as it reduces the length of the instruments needed to reach the pulmonary embolism.

Figure 2B:
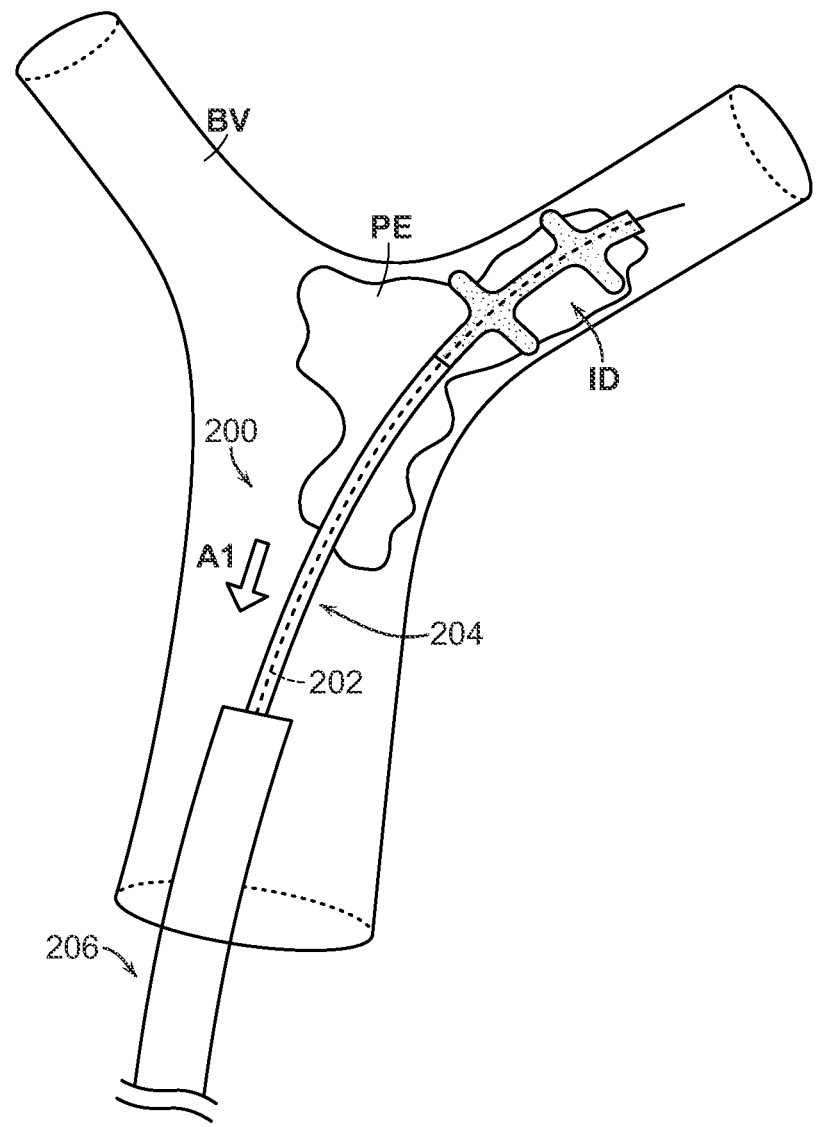
Figure 2C:
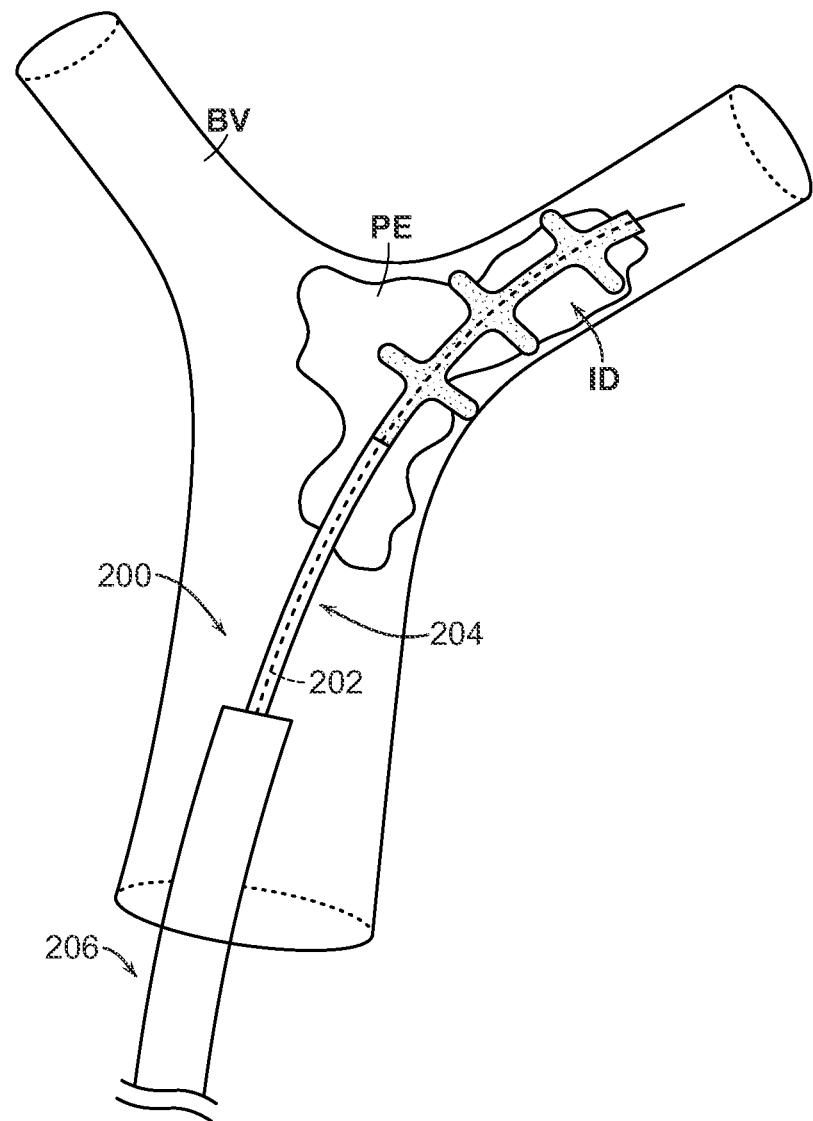
Figure 2D:
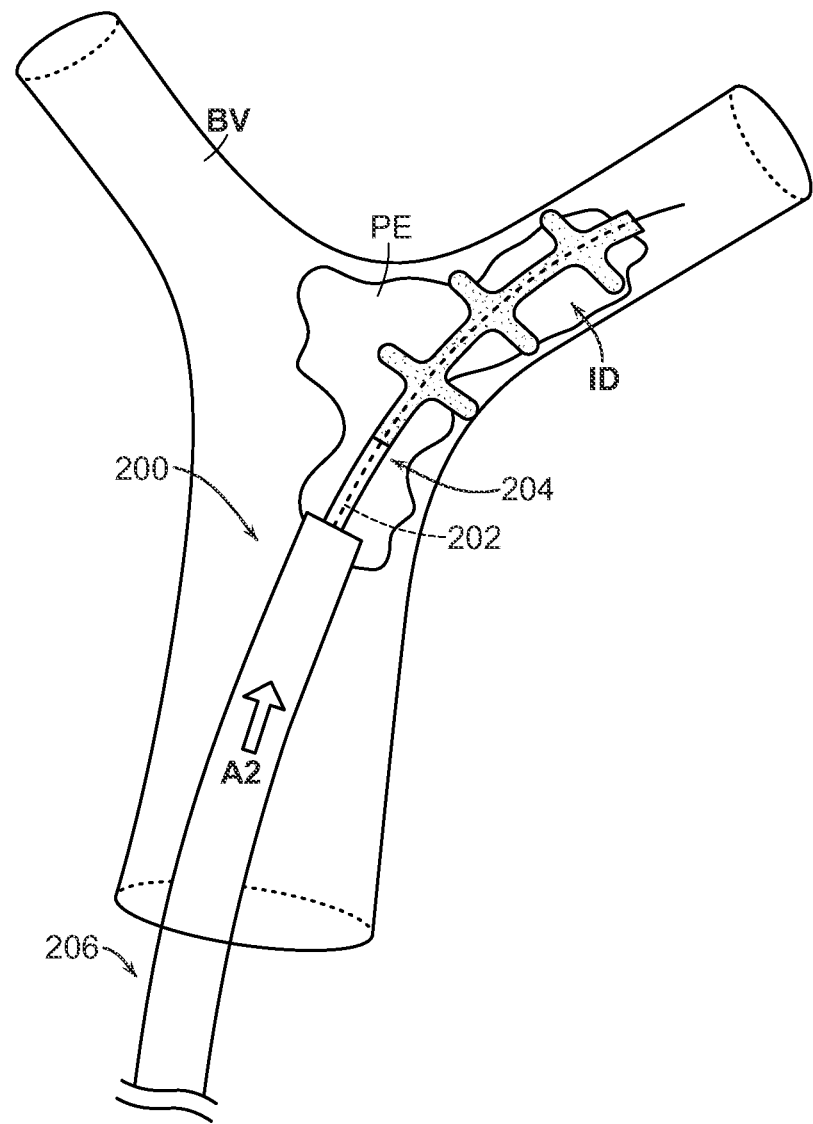

As shown in FIGS. 2B and 2C, the delivery sheath 204 can be withdrawn proximally (e.g., as indicated by arrow A1 in FIG. 2B) to allow the interventional device ID to expand within the clot material PE, thereby grabbing the clot material PE that is nearby. Although FIG. 2B shows the interventional device ID positioned at the treatment site such that a distal terminus of the interventional device ID is distal of a distal terminus of the clot material PE, in some procedures the interventional device ID may be positioned such that the distal terminus of the interventional device ID is proximal of the distal terminus of the clot material PE. As shown in FIG. 2D, in some embodiments the guide catheter 206 can optionally be advanced distally (e.g., as indicated by arrow A2) until the guide catheter 206 is positioned proximate to a proximal portion of the clot material PE.

Referring again to FIGS. 1A and 1B, the RA device 100 includes (i) a housing 102, (ii) an actuation mechanism that includes a lever 104 coupled to and extending from the housing 102, and (iii) a pressure source (obscured in FIGS. 1A and 1B; e.g., a syringe) positioned within the housing 102, coupled to the actuation mechanism, and configured to generate negative and/or positive pressure. The lever 104 is shown in a first position and second position in FIGS. 1A and 1B, respectively. The housing 102 can have a proximal portion 100a, a distal portion 100b, and an opening 114 at the distal portion 100b configured to receive a portion of the catheter system 200 and to mechanically couple the catheter system 200 to the housing 102. For example, a proximal portion of the guide catheter 206 can include an attachment/valve member 208 that is configured to be detachably coupled to the RA device 100 (e.g., via a snap-fit arrangement) to secure the catheter 200 to the RA device 100. As described in greater detail below, the attachment/valve member 208 can fluidly couple an aspiration lumen of the catheter system 200 (e.g., the lumen 205 of the guide catheter 206) to the tubing system 300 of the clot retrieval system 1.

The housing 102 can further include a channel 116 that extends proximally from the opening 114 along approximately the length of the housing 102, as shown in FIGS. 1A and 1B. The channel 116 can have a height at least as great as the outer diameter of the delivery sheath 204 of the catheter system 200 (and/or another component of the catheter system 200) such that the delivery sheath 204 can fit sideways through the channel 116. In some embodiments, the pull member 202 and the interventional device ID (FIGS. 2A-2G) can be pre-loaded into the delivery sheath 204, and the delivery sheath 204 can be fed distally through the channel 116 (e.g., either via the proximal end of the channel 116 or first pushed sideways through a portion of the channel 116) and into the guide catheter 206. In other embodiments, the interventional device ID and the delivery sheath 204 are fed into the guide catheter 206 and the interventional device ID is deployed prior to coupling the guide catheter 206 to the RA device 100.

When the RA device 100 is coupled to the catheter system 200 (e.g., when the attachment/valve member 208 of the catheter system 200 is positioned within the opening 114 in the housing 102 of the RA device 100), movement of the lever 104 functions to retract a portion of the catheter system 200 positioned in the channel 116 (e.g., the delivery sheath 204 and/or the push member 202). For example, the RA device 100 can include a locking portion that grips the delivery sheath 204 (and, in some embodiments, indirectly the push member 202) to pull the delivery sheath 204 proximally as the lever 104 is moved from the first to the second position.

The tubing system 300 of the clot retrieval system 1 fluidly couples the pressure source of the RA device 100 to the aspiration lumen of the catheter system 200. When the RA device 100 is coupled to the catheter system 200, movement of the lever 104 functions to simultaneously generate negative pressure in the pressure source and to retract a portion of the catheter system 200, as described above. The tubing system 300 has a first portion 314 coupled to the pressure source, a second portion 316 coupled to the guide catheter 206, and a drainage portion 318 coupled to a reservoir 320 (e.g., a vinyl bag). The first portion 314, second portion 316, and/or drainage portion 318 can include one or more tubing sections 302 (labeled individually as tubing sections 302a-302f) and/or fluid control unit, such as one or more control valves. In certain embodiments, one or more of the tubing sections 302 can have a relatively large diameter (e.g., greater than about 0.1 inch, greater than about 0.210 inch, etc.) to help inhibit clogging of clot material within the tubing system 300.

More specifically, the first portion 314 can include the tubing section 302a. The drainage portion 318 can include (i) the tubing section 302b, (ii) a first fluid control unit (e.g., a valve) 304, and (iii) the tubing section 302c. The second portion 316 can include (i) the tubing section 302d, (ii) a clot reservoir 306, (iii) the tubing section 302e, (iv) a second fluid control unit 310, and (v) the tubing section 302f. In some embodiments, the first fluid control unit 304 can be a one-way valve (e.g., a check valve) that only allows fluid flow from the first portion 314 and/or second portion 316 to the drainage portion 318 (and not vice-versa). In certain embodiments, as described in detail with reference to FIGS. 3A-3C, the clot reservoir 306 can also include a one-way valve that only allows fluid flow from the second portion 316 to the drainage portion 318 (and not vice-versa). In some embodiments, the second fluid control unit 310 can be a stopcock or a clamp that is externally operated to regulate the flow of liquid through the second portion 316 of the tubing system 300. A Y-connector 308 can fluidly couple the first, second, and drainage portions 314, 316, 318. In other embodiments, the first, second, and/or drainage portions 314, 316, 318 can have more or fewer tubing sections, connectors, and/or fluid control unit and/or other suitable configurations.

Figure 2E:
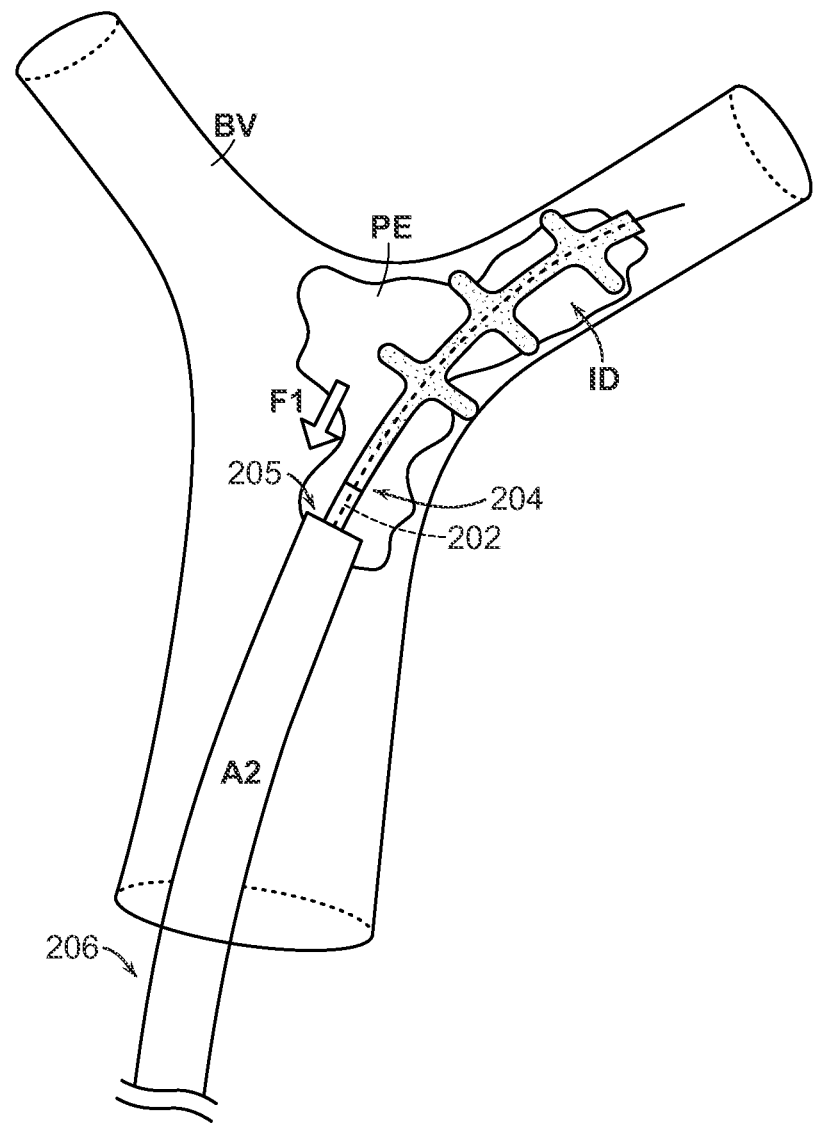

As shown in FIGS. 1A and 2E, moving the lever 104 from the first position to the second position (indicated by arrow A1 in FIG. 1A) simultaneously (1) generates a negative pressure in the lumen 205 of the guide catheter 206 (indicated by arrow F in FIG. 1A and F1 in FIG. 2E), and (2) retracts the delivery sheath 204 and/or push member 202 proximally, thereby retracting the interventional device ID from the treatment site. During this time, in some embodiments, the guide catheter 206 remains fixed (e.g., by the housing 102) relative to the delivery sheath 204 and pull member 202. In such embodiments, as the lever 104 moves from the first position to the second position, the interventional device ID, delivery sheath 204, pull member 202, and at least a portion of the clot material PE are drawn proximally into the guide catheter 206.

As shown in FIG. 1B, moving the lever 104 from the second position to the first position (indicated by arrow A2 in FIG. 1B) creates a positive pressure (e.g., indicated by arrows F in FIG. 1B) in the first portion 314 and drainage portion 318 of the tubing system 300. The clot reservoir 306 prevents the positive pressure from affecting the aspiration lumen of the catheter system 200, thereby preventing backflow of fluid into the blood vessel BV at the treatment site. With respect to the catheter system 200, when the lever 104 is actuated from the second position to the first position, the RA device 100 does not engage the delivery sheath 204 or the push member 202 to move these components. Thus, the next time the lever 104 is actuated relative to the housing 102, the RA device 100 engages a new portion of the delivery sheath 204 and push member 202 such that the delivery sheath 204 and push member 202 are incrementally retracted proximally each time the lever 104 is "pumped" (e.g., moved from the first position toward the second position and then back toward the first position).

Figure 2F:
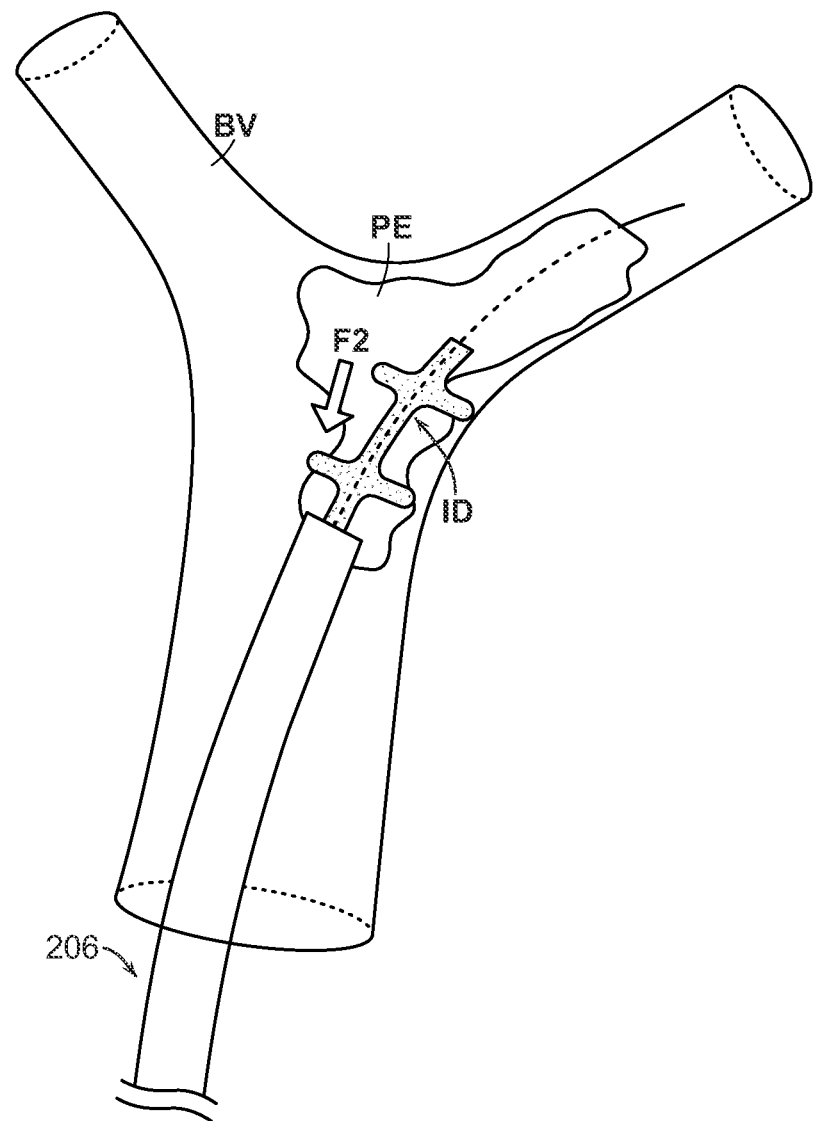

Depending on the age and size of the clot material PE, local anatomical and/or physiological conditions, and position of the interventional device ID relative to the clot material PE, the lever 104 can be pumped several times to fully extract the clot material PE and/or interventional device ID from the treatment site. For example, FIGS. 2D and 2E show the proximal movement of the delivery sheath 204 and pull member 202 after a first pump of the lever 104. FIGS. 2E and 2F show the proximal movement of the delivery sheath 204, pull member 202, and interventional device ID after a second pump of the lever 104 (e.g., including a second instance of pressure generation indicated by arrows F1 and F2 in FIGS. 2E and 2F, respectively). In some embodiments, the interventional device ID and the clot material PE can be fully withdrawn into the guide catheter 206 after a single pump of the lever 104. In other embodiments, such as those procedures where the interventional device ID is initially positioned such that a distal terminus of the interventional device ID is proximal of a distal terminus of the clot material PE (the clot material PE often originates in a vein of the patient's leg, and thus is cast into an elongated, worm-like shape), it can take several pumps of the lever 104 to fully withdraw the clot material PE into the guide catheter 206. Thus, in some embodiments, even when the interventional device ID is positioned within the guide catheter 206 such that a distal terminus of the interventional device ID is proximal of the distal terminus of the guide catheter 206, the lever 104 can be pumped several more times to continue to withdraw the clot material PE into the guide catheter 206 and the tubing system 300 (e.g., into the second portion 316, the clot reservoir 306, and/or the drainage portion 318).

Figure 2G:
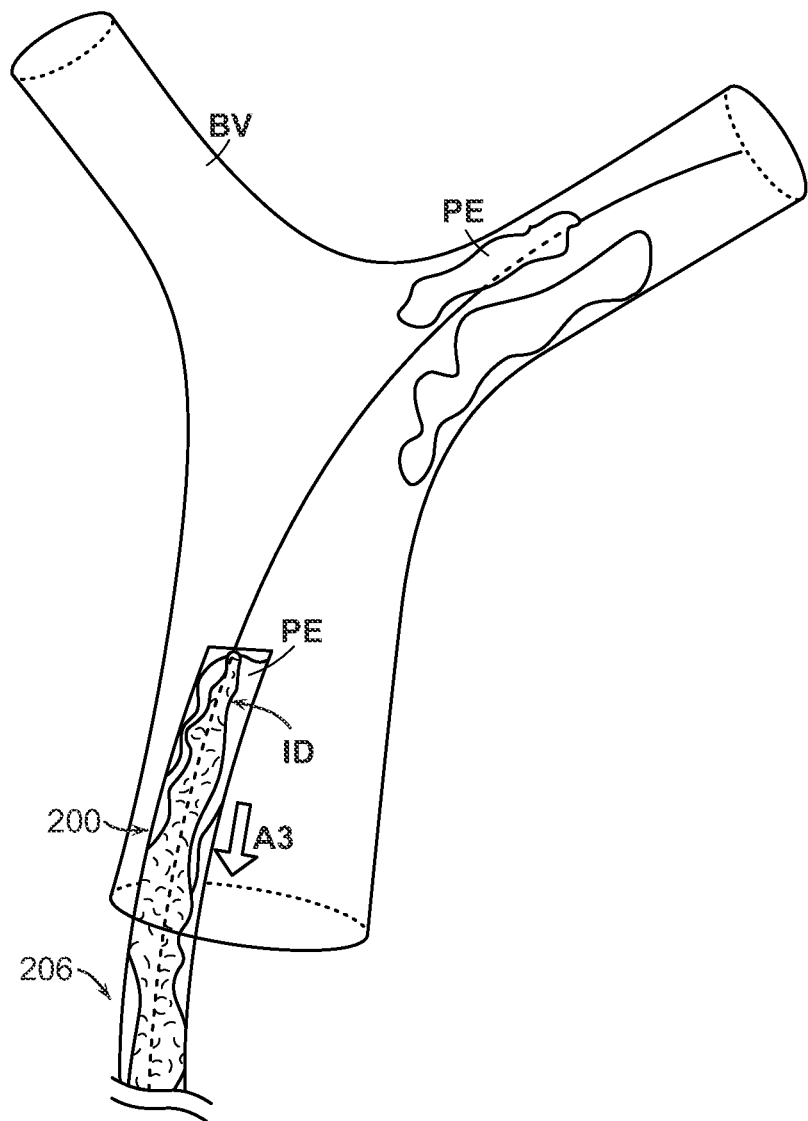

Once the clot material PE is positioned within the guide catheter 206 such that a distal terminus of the clot material PE is proximal from a distal terminus of the guide catheter 206, the catheter system 200 can be withdrawn proximally (e.g., as indicated by arrow A3 in FIG. 2G) from the treatment site, and removed from the patient. However, sometimes, as shown in FIG. 2G, retracting the interventional device ID and delivery sheath 204 into the guide catheter 206 may not remove all of the clot material PE (or a desired amount of the clot material PE) from the blood vessel BV. That is, a single "pass" (e.g., a deployment of the interventional device ID and subsequent retraction of the interventional device ID into the guide catheter 206) may not adequately remove the clot material PE from the blood vessel BV. In such instances, the operator of the clot retrieval system 1 may wish to make another pass with the interventional device ID to remove all or a portion of the remaining clot material PE in the blood vessel BV.

To redeploy the interventional device ID, many conventional systems require that the entire catheter system, including the guide catheter 206, be fully removed from the patient (e.g., including a guide catheter). That is, if the once-deployed interventional device is reintroduced without fully removing and cleaning the catheter system, there is a significant risk that clot material and/or other contaminants from the catheter system will be reintroduced into the blood vessel of the patient during a second pass. As described in further detail below, the present technology advantageously allows for an interventional device to be redeployed without fully removing a guide catheter, and with a significantly reduced risk of reintroducing clot material and/or other contaminants into the blood vessel of the patient.

II. SELECTED EMBODIMENTS OF CLOT RESERVOIRS AND ASSOCIATED METHODS OF USE

Figure 3A:
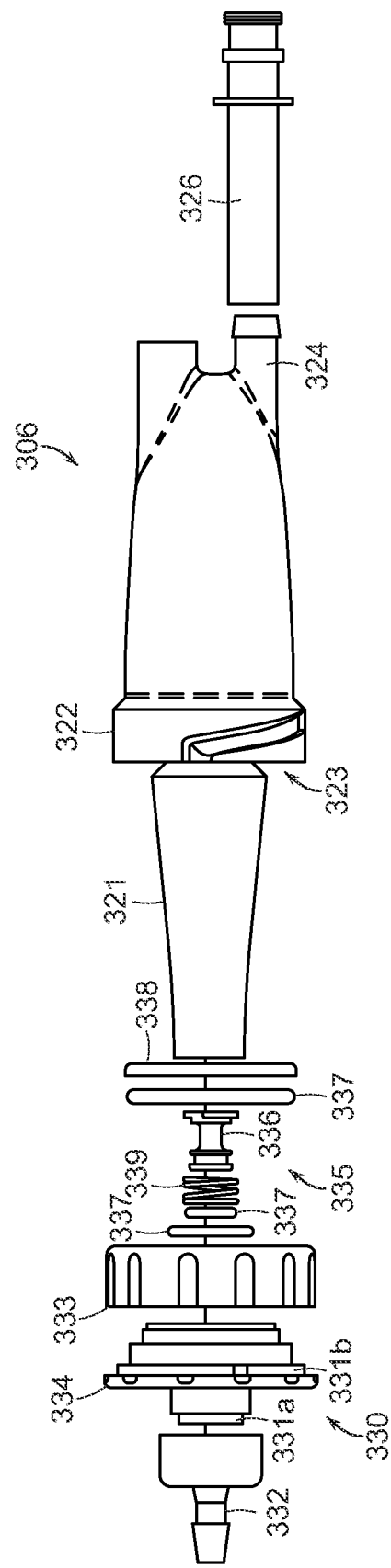
FIGS. 3A-3C are a fully-exploded view, an isometric view, and a partially-exploded view of a clot reservoir of the retraction and aspiration system in accordance with embodiments of the present technology.
Figure 3B:
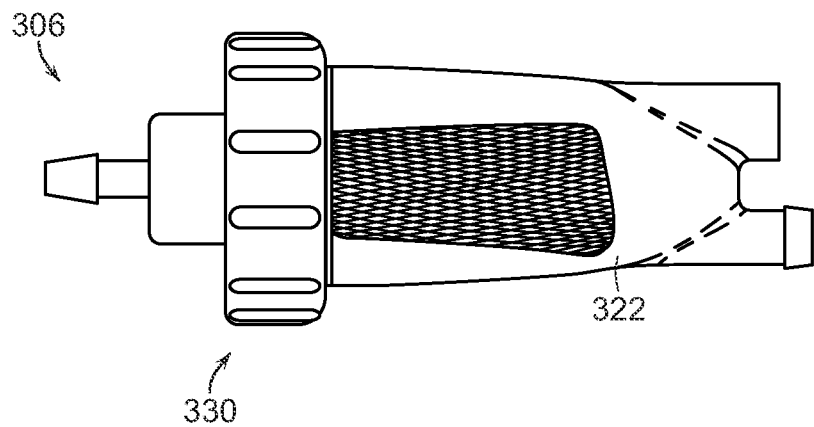
Figure 3C:
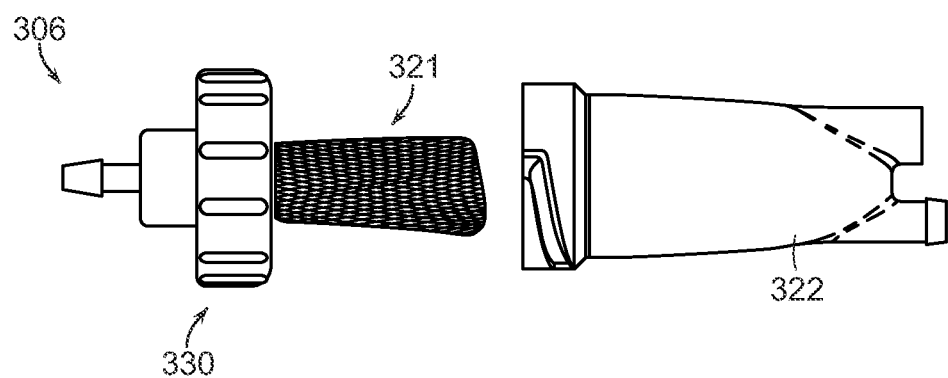

FIGS. 3A-3C are a fully-exploded view, an isometric view, and a partially-exploded view of the clot reservoir 306 of the clot retrieval system 1. With reference to FIG. 3A, the clot reservoir 306 includes a housing 322 defining a chamber 323, a filter 321 configured to be positioned within the housing 322, and a cap assembly 330 configured to be coupled to the housing 322. The housing 322 can include a port 324 configured to be removably, fluidly coupled to the catheter system 200. In some embodiments, a tubing section 326 is coupled to the port 324 during priming of the clot retrieval system 1 and, as described in further detail below with reference to FIGS. 10 and 14, during flushing of the tubing system 300. In certain embodiments the tubing section 326 is semi-permanently coupled to the housing 322 and can be used to fluidly couple the housing 322 to the tubing system 300 and/or the catheter system 200.

In the embodiment illustrated in FIG. 3A, the cap assembly 330 includes a fluid connector (e.g., a barbed outlet) 332 for connecting to the tubing system 300 (e.g., to the tubing section 302d shown in FIGS. 1A and 1B), a nut 333 for releasably securing the cap assembly 330 to the housing 322 (e.g., via a threaded coupling), a first cap portion 334, and a second cap portion 338. In some embodiments, the fluid connector 332 is secured to the first cap portion 334 via an adhesive 331a, and the first cap portion 334 is secured to the nut 333 via a second adhesive 331b. In some embodiments, the first and second adhesives 331a, 331b are the same. The cap assembly 330 can further include a check valve assembly 335 positioned between the first and second cap portions 334, 338 and comprising a piston 336 and a spring 339 (e.g., a passivated compression spring). The check valve assembly 335 provides for one-way fluid flow through the clot reservoir 306, for example, from the catheter system 200 to the reservoir 320 (FIGS. 1A and 1B). The clot reservoir 306 can further include one or more O-rings 337 for sealing the various components.

In operation, blood and clot material flow into the clot reservoir 306 via the port 324 as the lever 104 of the RA device 100 is moved from the first position toward the second position. Clot material is captured within the housing 322 and inhibited from exiting through the cap assembly 330 by the filter 321 while blood is allowed to flow from the port 324 to the fluid connector 332. In particular, the filter 321 inhibits clot material from passing into the check valve assembly 335, which could inhibit function of the check valve assembly 335 and/or macerate the clot material and make it indistinguishable from or difficult to distinguish from other fluids (e.g., blood) aspirated and/or removed from the patient. The check valve assembly 335 subsequently inhibits backflow of fluid through the housing 322 via the fluid connector 332 as the lever 104 of the RA device 100 is moved from the second position toward the first position. With reference to FIGS. 3B and 3C, the cap assembly 330 can be decoupled from the housing 322 to, for example, permit an operator to remove clot material collected in the housing 322. Moreover, as shown, the housing 322 may be made of a transparent material that permits the operator to visualize material within the housing 322. As described in further detail below, in some embodiments, the operator can at least partially determine whether subsequent passes using the interventional device ID are necessary by visualizing the amount of clot material collected in the housing 322.

Additional details of the clot reservoir 306, and associated devices and methods, are described in Appendix A to this application.

III. SELECTED EMBODIMENTS OF ATTACHMENT/VALVE MEMBERS, AND ASSOCIATED DEVICES AND METHODS OF USE

Figure 4:
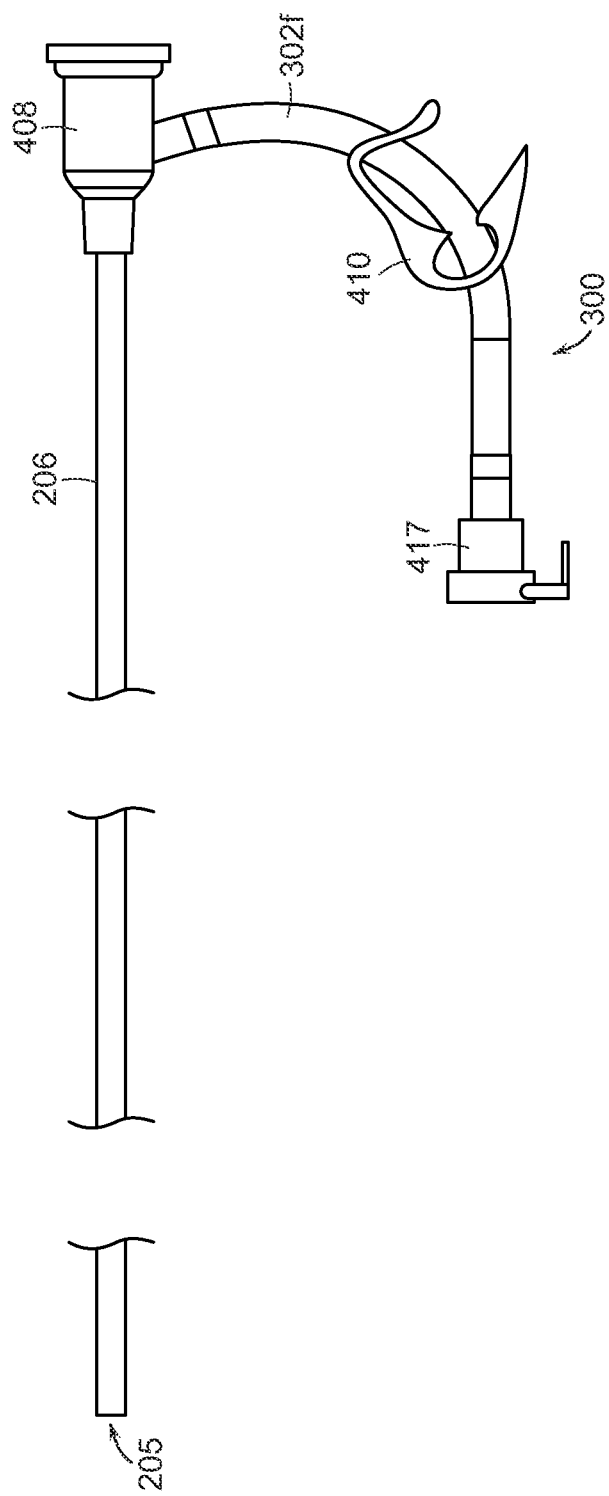
FIG. 4 is a side view of an attachment member and a fluid control unit of the retraction and aspiration system in accordance with embodiments of the present technology.

FIG. 4 is a side view of an attachment/valve member 408 ("attachment member 408") of the catheter system 200 and a second fluid control unit 410 of the tubing system 300 in accordance with embodiments of the present technology. The attachment member 408 and second fluid control unit 410 can have some features generally similar to the features of the attachment/valve member 208 and second fluid control unit 310, respectively, described above with reference to FIGS. 1A and 1B. For example, the attachment member 408 can be integral with or coupled to a proximal portion of the guide catheter 206 and configured to be detachably coupled to the RA device 100 (FIGS. 1A and 1B; e.g., via a snap-fit arrangement) to at least partially secure the catheter system 200 to the RA device 100. When secured to the RA device 100, the attachment member 408 can fluidly couple the lumen 205 (e.g., an aspiration lumen) of the guide catheter 206 to the tubing system 300 of the clot retrieval system 1 via the tubing section 302f. Likewise, the second fluid control unit 410 can be a clamp ("clamp 410") that is externally operable to regulate the flow of liquid through the tubing section 302f. For example, the clamp 410 may be actuated (e.g., compressed or squeezed by the hand of an operator) to partially or fully restrict fluid flow through the tubing section 302f. In some embodiments, the clamp 410 includes features for locking or maintaining the clamp 410 in a position such that it restricts fluid flow through the tubing section 302f. FIG. 4 illustrates the clamp 410 in a position that permits fluid flow through the tubing section 302f.

As further shown in FIG. 4, the tubing system 300 can include a connector 417 that, for example, fluidly connects the tubing section 302f to other portions of the tubing system 300 (e.g., those shown in FIGS. 1A and 1B). In some embodiments, the connector 417 is a quick-release connector that enables rapid coupling/decoupling of the tubing section 302f to the clot reservoir 306 and/or other components of the tubing system 300. In some embodiments, the tubing system 300 can include a flush port adapter that can be removably coupled to the connector 417. The flush port adapter can be configured to, for example, fluidly connect a flushing device (e.g., a syringe) to the catheter system 200 so that the guide catheter 206 can further be flushed with a fluid (e.g., heparinized saline).

Figure 5:
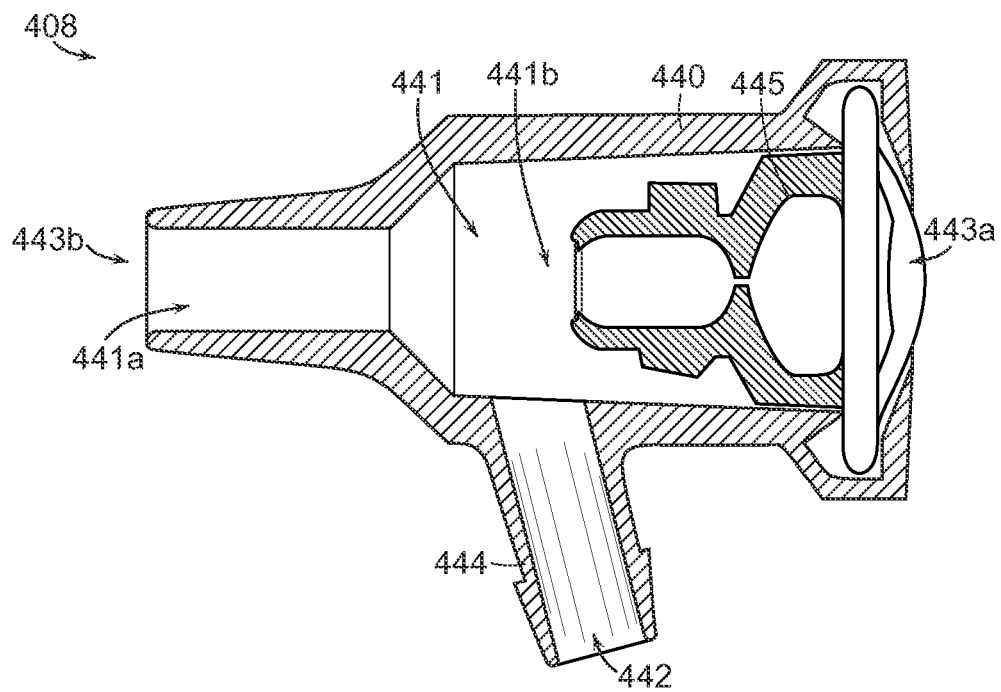
FIG. 5 is a side cross-sectional view of the attachment member shown in FIG. 4.

FIG. 5 is a side cross-sectional view of the attachment member 408 show in FIG. 4. As shown in the embodiment of FIG. 5, the attachment member 408 includes a body or housing 440 having a proximal opening 443a, a distal opening 443b, and a first lumen 441 extending between the proximal and distal openings 443a and 443b. The first lumen 441 further comprises a first portion 441a having a first diameter (e.g., a constant first diameter) and a second portion 441b having a second diameter greater than the first diameter. In some embodiments, the first diameter can be generally the same as the outer diameter of the guide catheter 206. The housing 443 further includes a branch portion 444 configured to be coupled to the tubing section 302f and having a second lumen 442 branching from the first lumen 441. In some embodiments, the second lumen 442 can have a relatively large diameter (e.g., between about 0.098 inch and 0.210 inch, about 0.210 inch, greater than 0.210 inch, etc.) to help inhibit clogging and/or collecting of clot material within the attachment member 408 during, for example, aspiration of the guide catheter 206.

As illustrated in the embodiment of FIG. 5, the attachment member 408 can further include a valve 445 within the second portion 441b of the first lumen 441. The valve 445 can be, for example, a hemostasis valve configured to maintain hemostasis by preventing fluid flow in the proximal direction through the proximal opening 443a of the attachment member 408 as the delivery sheath 204, the pull member 202, the guidewire, the interventional device ID, and/or other components of the catheter system 200 are inserted through the valve 445 for advancement to the treatment site in the blood vessel BV.

Figure 6:
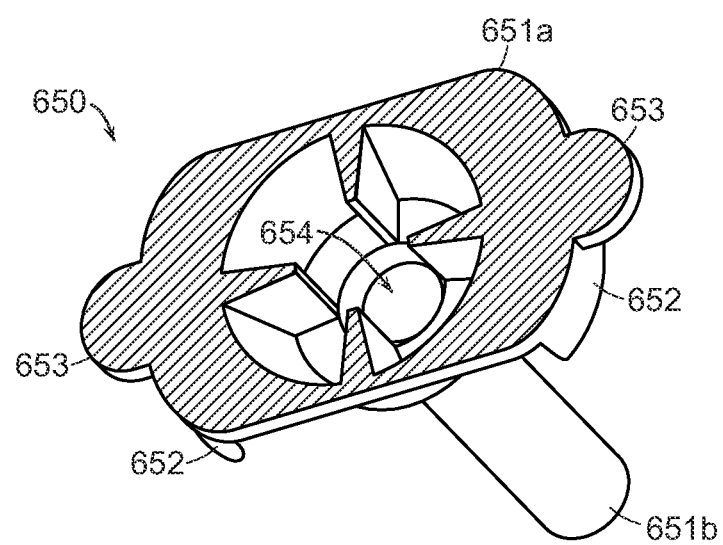
FIG. 6 is an isometric view of a first valve insert in accordance with embodiments of the present technology.
Figure 7A:
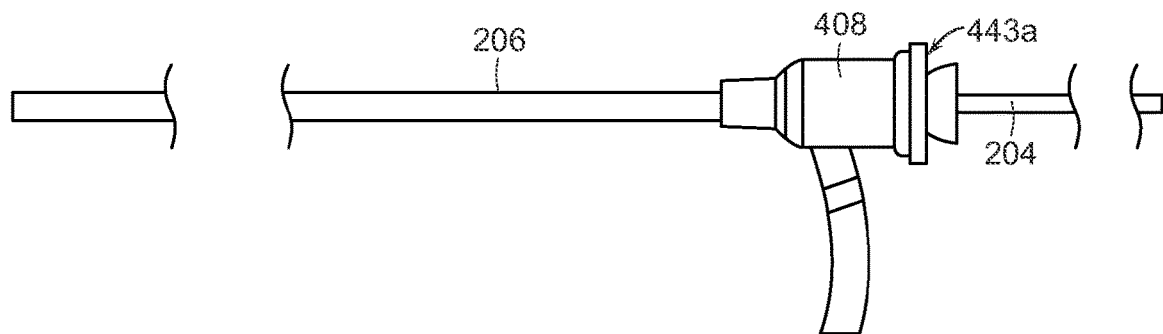
FIGS. 7A and 7B are a side view and a side cross-sectional view, respectively, of the first valve insert shown in FIG. 6 inserted into the attachment member shown in FIG. 4 in accordance with embodiments of the present technology.

FIG. 6 is an isometric view of a first valve insert 650, such as a hub valve insert, in accordance with embodiments of the present technology. The first valve insert 650 is configured to be inserted at least partially into the first lumen 441 of the attachment member 408 (e.g., into the valve 445) through the proximal opening 443a of the attachment member 408. Accordingly, FIGS. 7A and 7B are a side view and a side cross-sectional view, respectively, of the first valve insert 650 inserted into the attachment member 408 in accordance with embodiments of the present technology.

Referring to FIG. 6, the first valve insert 650 includes a proximal portion 651a, a distal portion 651b extending from the proximal portion 651a, and a lumen 654. As illustrated in the embodiment of FIG. 6, the proximal portion 651a can optionally include one or more first engagement features (e.g., flanges, tabs, etc.) 652 configured to engage with the attachment member 408 of the of the catheter system 200 to securely position (e.g., lock, mate, flush, etc.) the first valve insert 650 within the attachment member 408. For example, in some embodiments, the first engagement features 652 can be configured to "snap" into (e.g., mate with) corresponding grooves on the attachment member 408. The proximal portion 651a can further include one or more second engagement features 653 (e.g., flanges, tabs, etc.) configured to be gripped by an operator to enable the operator to, for example, easily manipulate and/or position the first valve insert 650 within the attachment member 408.

Figure 7B:
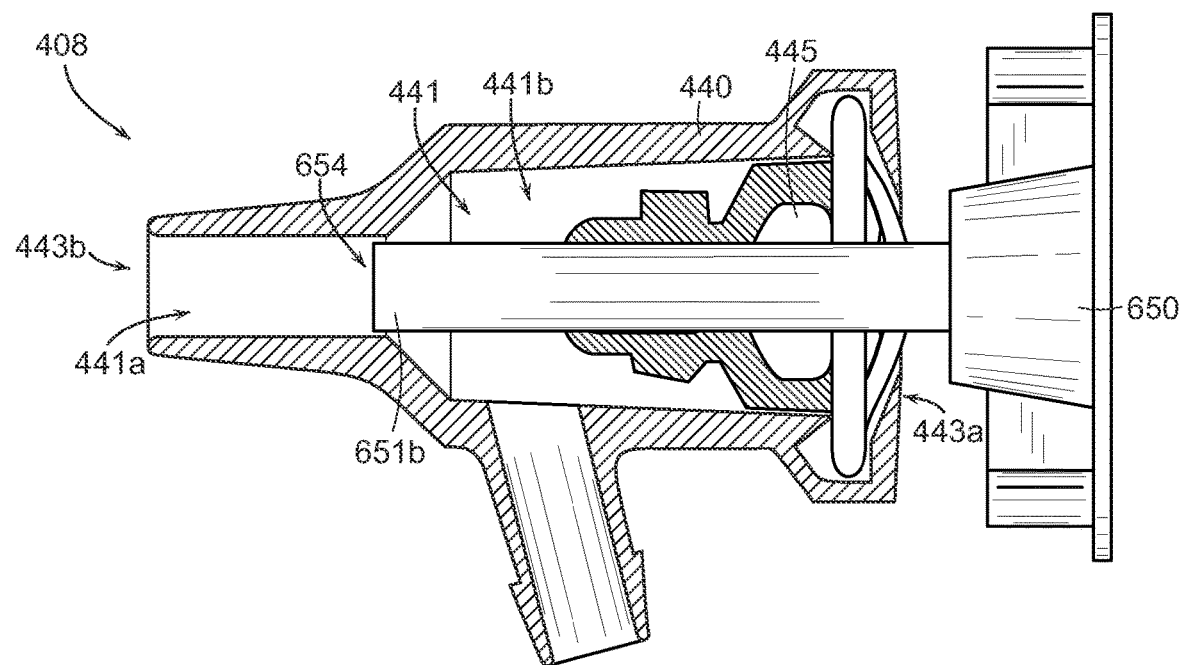

Referring to FIGS. 6-7B together, the distal portion 651b of the first valve insert 650 is configured to be positioned at least partially within the second portion 441b of the first lumen 441 of the attachment member 408. For example, the first valve insert 650 can be advanced distally over the delivery sheath 204 and/or the guidewire of the catheter system 200 to the attachment member 408. Once inserted into the attachment member 408, the first valve insert 650 opens (e.g., exercises) the valve 445. In some embodiments, the lumen 654 of the distal portion 651b of the first valve insert 650 has a generally constant diameter that is generally the same as the first diameter of the first portion 441a of the first lumen 441 of the attachment member 408. In the embodiment illustrated in FIG. 7B, when the first valve insert 650 is within the attachment member 408, the distal portion 651b extends substantially or entirely through the second portion 441b of the first lumen 441 such that the lumen 654 of the first valve insert 650 and the second portion 441a of the first lumen 441 of the attachment member 408 together define a generally continuous lumen extending through the attachment member 408 (e.g., between the distal opening 443b of the attachment member 408 and a proximal terminus of the lumen 654).

In one aspect of the present technology, the continuous lumen formed by inserting the first valve insert 650 into the attachment member 408 can have a generally constant diameter along the length of the lumen configured to accommodate the outer diameter of the guide catheter 206. Accordingly, as described in further detail below, when a clot retaining portion of an interventional device and associated clot material are retracted proximally through the guide catheter 206, the interventional device ID does not greatly change shape (e.g., expand or compress) while passing through the attachment member 408 and the likelihood of clot material being retained within the attachment member 408 is greatly reduced.

Figure 8:
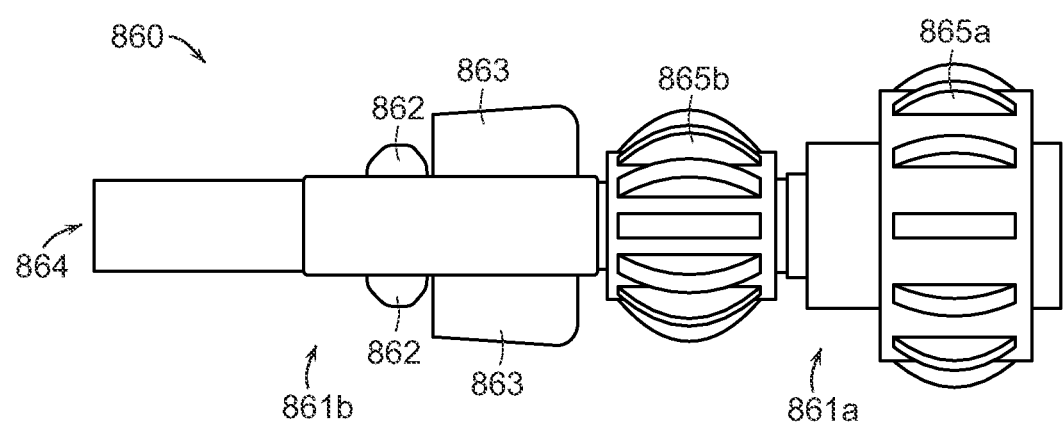
FIG. 8 is a side view of a second valve insert in accordance with embodiments of the present technology.
Figure 9:
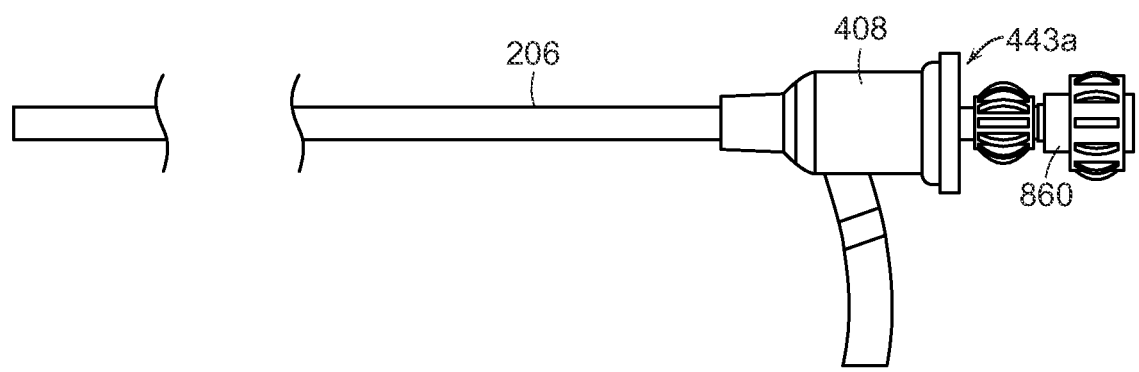
FIG. 9 is a side view of the second valve insert shown in FIG. 8 inserted into the attachment member shown in FIG. 4 in accordance with embodiments of the present technology.

FIG. 8 is a side view of a second valve insert 860 (e.g., an aspiration insert) in accordance with embodiments of the present technology. Similar to the first valve insert 650, the second valve insert 860 is configured to be inserted at least partially into the first lumen 441 of the attachment member 408 (e.g., through the valve 445) through the proximal opening 443a of the attachment member 408. Accordingly, FIG. 9 is a side view of the second valve insert 860 inserted into the attachment member 408 in accordance with embodiments of the present technology.

Referring to FIG. 8, the second valve insert 860 includes a proximal portion 861a, a distal portion 861b extending from the proximal portion 861a, and a lumen 864 extending through the second valve insert 860. As illustrated in the embodiment of FIG. 8, the distal portion 861b can optionally include one or more first engagement features (e.g., flanges, tabs, etc.) 862 configured to engage with the attachment member 408 to securely position (e.g., lock) the second valve insert 860 within the attachment member 408. For example, in some embodiments, the first engagement features 862 can be configured to "snap" into (e.g., mate with) corresponding grooves on the attachment member 408. The proximal portion 861a can further include one or more second engagement features 865a (e.g., flanges, tabs, etc.) configured to be gripped by an operator to enable the operator to, for example, easily manipulate and/or position the second valve insert 860 within the attachment member 408.

The proximal portion 861a can include one or more adjustment features 865 (labeled individually as adjustment features 865a and 865b) for adjusting a diameter of the lumen 864. For example, in some embodiments the second valve insert 860 is a Tuohy Borst Adapter that can be adjusted, via the one or more adjustment features 865, to seal the proximal opening 443a of the attachment member 408 by sealing the lumen 864 against a component of the catheter system 200 inserted therethrough. More particularly, referring to FIGS. 8 and 9 together, the distal portion 861b of the second valve insert 860 is configured to be positioned at least partially within the attachment member 408 (e.g., within the second portion 441b of the first lumen 441). For example, the second valve insert 860 can be advanced distally over the guidewire of the catheter system 200 to the attachment member 408. Once inserted into the attachment member 408, the second valve insert 860 opens (e.g., exercises) the valve 445. By tightening at least one of the adjustment features 865, at least a portion of the lumen 864 can be narrowed until a seal is formed between the second valve insert 860 and the guidewire or other component of the catheter system 200 positioned therein.

As described in further detail below, in some embodiments, the second valve insert 860 may more completely seal against components of the catheter system 200 than the valve 445 of the attachment member 408. Accordingly, use of the second valve insert 860 can improve the efficiency of aspiration of the guide catheter 206 using the RA device 100 (FIGS. 1A and 1B).

Figure 10:
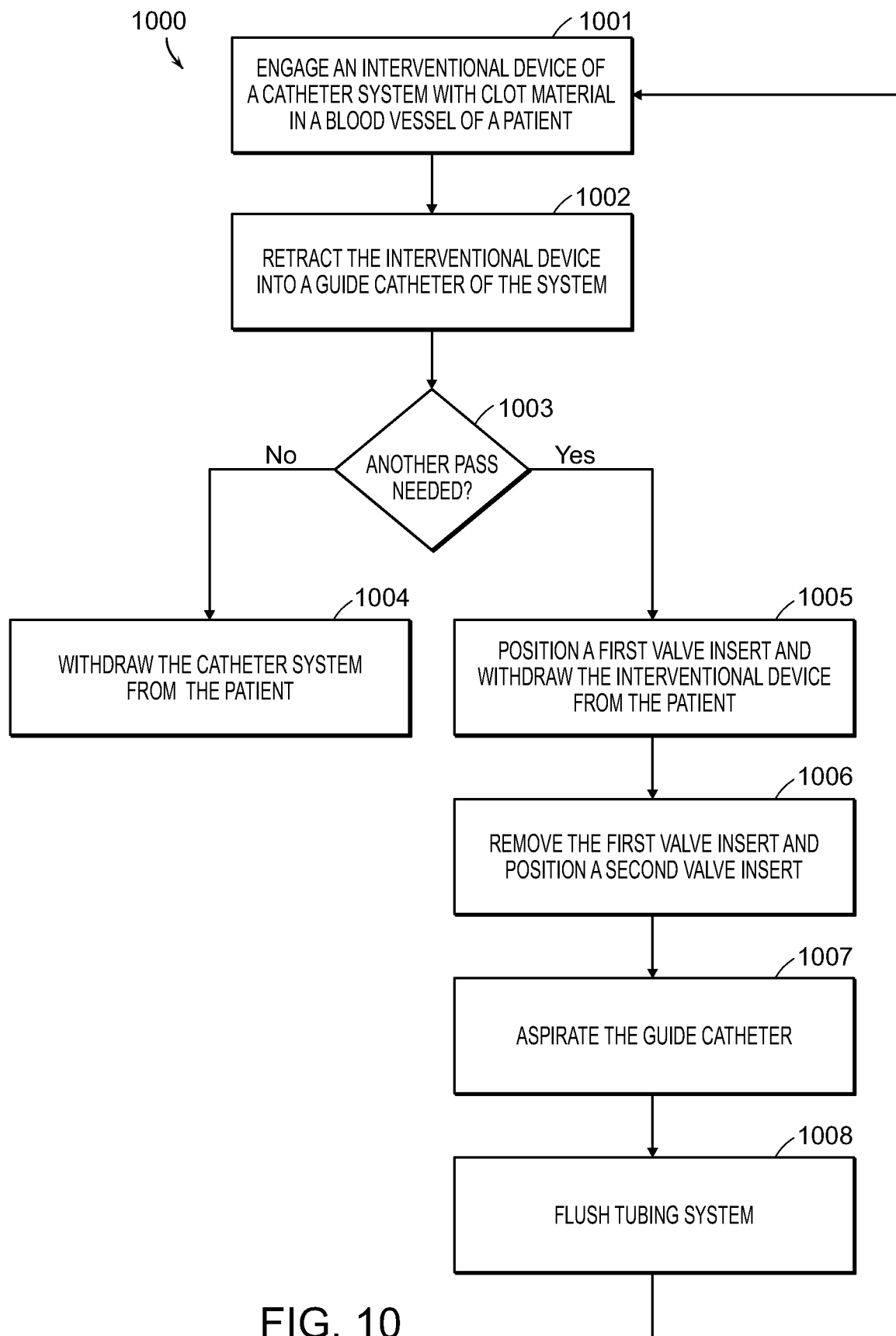
FIG. 10 is a flow diagram of a process or method for operating the retraction and aspiration system in accordance with embodiments of the present technology.

FIG. 10 is a flow diagram of a process or method 1000 for operating the clot retrieval system 1 including the attachment member 408 and the first and second valve inserts 650, 860 to remove clot material from within a blood vessel (e.g., a pulmonary blood vessel) of a human patient in accordance with embodiments of the present technology. Although some features of the method 1000 are described in the context of the embodiments shown in FIGS. 1A-9 for sake of illustration, one skilled in the art will readily understand that the method 1000 can be carried out using other suitable systems and/or devices.

The method 1000 includes engaging the interventional device ID of the catheter system 200 with the clot material PE in the blood vessel BV as, for example, described above with reference to FIGS. 2A-2D (block 1001). In particular, the attachment member 408 (FIGS. 4 and 5) of the catheter system 200 can be attached to the RA device 100, and the interventional device ID can be deployed within at least a portion of the clot material PE by proximally retracting the delivery sheath 204.

The method 1000 continues by proximally retracting the interventional device ID and associated clot material PE into the guide catheter 206 of the catheter system 200 until a distal terminus of the clot material PE is proximal from a distal terminus of the guide catheter 206 as, for example, described above with reference to FIGS. 2E-2G (block 1002). In particular, the RA device 100 can be pumped or cycled one or more times (e.g., one time, three times, five times, etc.) to retract the interventional device ID and/or delivery sheath 204 into the guide catheter 206 while simultaneously aspirating the lumen 205 of the guide catheter 206 to remove clot material PE and blood, which are drawn through the attachment member 408 and into the tubing system 300 (e.g., through the clot reservoir 306 to the reservoir 320).

In some embodiments, the interventional device ID can be retracted proximally into the guide catheter 206 without use of the RA device 100. For example, the operator can manually retract the interventional device ID and associated clot material PE into the guide catheter 206.

After initial deployment of the interventional device ID in blocks 1001 and 1002, the operator can determine whether it is necessary or desirable to redeploy the interventional device ID within the blood vessel BV of the patient in order to remove additional clot material PE that was not removed during a previous pass with the interventional device ID (block 1003). In some embodiments, the operator can visualize the amount of clot material PE collected in the clot reservoir 306 to at least partially determine whether another pass is needed. In other embodiments, the operator can rely on imaging (e.g., fluoroscopic imaging) of the blood vessel BV or other techniques known in the art to determine whether an additional pass is necessary. If another pass is not needed (e.g., the clot material PE was adequately removed), the operator can elect to withdraw the catheter system 200 from the patient (block 1004). If clot material PE remains in the vessel, the operator can prepare to redeploy the interventional device ID.

To redeploy the interventional device ID, the method 1000 includes positioning the first valve insert 650 (FIG. 6) and withdrawing the interventional device ID from the patient (block 1005). In particular, before positioning the first valve insert 650, the catheter system 200 can be decoupled from the RA device by (i) decoupling the attachment member 408 from the distal portion 100b of the RA device 100 and (ii) removing the delivery sheath 204 and/or guidewire from the channel 116. Additionally, in some embodiments, the clamp 410 can be actuated (e.g., closed) to prevent fluid flow from the guide catheter 206 into the tubing system 300 during withdrawal of the interventional device ID.

The first valve insert 650 can be advanced over the delivery sheath 204 and/or guidewire of the catheter system 200 until it is positioned (e.g., seated) at least partially within the attachment member 408 (FIGS. 7A and 7B). Once the first valve insert 650 is positioned within the attachment member 408, the interventional device ID and delivery sheath can be fully withdrawn from the patient. For example, in some embodiments, the operator may grip a portion of the delivery sheath 204 that is exposed proximally from the RA device 100 and pull the delivery sheath 204 and interventional device ID proximally through the guide catheter 206. In some embodiments, the first valve insert 650 is only positioned within the attachment member 408 when the interventional device ID is proximate the attachment member 408. That is, the operator may partially withdraw the delivery sheath 204 and interventional device ID within the guide catheter 206 before advancing the first valve insert 650 into position. In some embodiments, the delivery sheath 204 includes a marking (e.g., a specific color pattern) configured to indicate to the operator that the distal end of the delivery sheath 204 and/or the interventional device ID is near (e.g., proximally approaching) the attachment member 408. In certain embodiments, the guidewire of the catheter system 200 is pinned during withdrawal of the interventional device ID and the delivery sheath 204 such that the guidewire does not move relative to the interventional device ID and the delivery sheath 204. Therefore, in such embodiments, the guidewire does not need to be re-advanced to the treatment site prior to an additional pass.

In operation, the first valve insert 650 helps create a lumen of constant diameter through the attachment member 408 such that a diameter of the interventional device ID does not substantially change (e.g., expand and/or contract) as the interventional device ID is withdrawn proximally through the attachment member 408. In particular, the first valve insert 650 can effectively shield the interventional device ID from the valve 445 of the attachment member 408. Without the first valve insert 650, as the interventional device ID is withdrawn proximally it can expand within the attachment member 408 (e.g., as the interventional device ID passes through the second portion 441b of the first lumen 441) before being squeezed (e.g., radially collapsed) as it passes through the valve 445. Without the first valve insert 650, the valve 445 may strip (e.g., break off, shear, etc.) clot material PE that held by the interventional device ID. This can cause clot material PE to remain in the attachment member 408 after the interventional device ID is fully withdrawn from the patient, which presents a significant risk that remaining clot material PE will be reintroduced into the blood vessel BV of the patient if a second pass is made with the interventional device ID without fully removing the guide catheter 206 from the patient to enable cleaning of the guide catheter 206 and the attachment member 408. The first valve insert 650 of the present technology inhibits clot material PE engaged with the interventional device ID from being stripped by the valve 445 within the attachment member 408 and, therefore, enables a second pass with the interventional device ID to be made without removing the guide catheter 206 from the patient.

The method 1000 includes removing the first valve insert 650 and positioning the second valve insert 860 (FIG. 9) (block 1006). For example, the first valve insert 650 can be withdrawn proximally over the guidewire of the catheter system 200 and the second valve insert 860 can then be advanced distally over the guidewire until it is positioned within the attachment member 408. In some embodiments, the first valve insert 650 is removed and the second valve insert 860 is inserted into the attachment member 408 immediately after the delivery sheath 204 and interventional device ID are withdrawn from the patient. Prompt removal of the first valve insert 650 can restore function of the valve 445 and prevent excess blood from leaking through the lumen 654 of the first valve insert 650 once the delivery sheath 204 and interventional device ID are removed.

Positioning the second valve insert 860 further includes adjusting (tightening) the second valve insert 860 over the guidewire to seal the proximal opening 443a of the attachment member 408. In some embodiments, the method 1000 need not include positioning of the second valve insert 860. Instead, the valve 445 of the attachment member 408 may provide a suitable seal for subsequent aspiration steps. However, in some embodiments, use of the second valve insert 860 can provide a better seal between the guidewire of the catheter system 200 and the attachment member 408, and thus improve the efficiency of aspiration using the RA device 100.

The method 1000 includes aspirating the guide catheter 206 by, for example, pumping or cycling the lever 104 of the RA device 100 one or more times (block 1007). In embodiments where the clamp 410 was previously closed (e.g., at block 1005), prior to pumping the lever 104, the operator can actuate (e.g., open) the clamp 410 to permit fluid flow from the guide catheter 206 into the tubing system 300. Aspirating the guide catheter 206 removes any residual clot material PE remaining in the guide catheter 206. Accordingly, the residual clot material PE is not reintroduced into the blood vessel BV of the patient when the interventional device ID and delivery sheath 204 are subsequently advanced through the guide catheter 206 during another pass. In certain embodiments, the guide catheter 206 can further be flushed with a fluid (e.g., heparinized saline). For example, the connector 417 can be decoupled from the tubing system 300 and the fluid can be introduced from a flushing device (e.g., a syringe) through a flush port adapter coupled (e.g., semi-permanently coupled) to the connector 417.

In some embodiments, the guide catheter 206 can be aspirated without use of the RA device 100. For example, a syringe or other pressure source can be fluidly coupled directly to the connector 417 and used to aspirate the guide catheter 206. In such embodiments, opening of the clamp 410 fluidly connects the syringe to the lumen 205 of the guide catheter 206 and closing of the clamp 410 fluidly disconnects the syringe from the lumen 205 of the guide catheter 206. In some embodiments, the syringe or other pressure source can be pre-charged with a vacuum-such as by drawing a plunger of the syringe with the clamp 410 closed. The clamp 410 can then be opened to instantaneously or nearly instantaneously (e.g., immediately) apply the stored vacuum pressure to the tubing system 300 and to the lumen 205 of the guide catheter 206, thereby generating suction throughout the guide catheter 206. In particular, suction can be generated at a distal portion of the guide catheter 206. In one aspect of the present technology, pre-charging or storing the vacuum before applying the vacuum to the lumen 205 of the guide catheter 206 is expected to generate greater suction forces with a faster ramp time (and correspondingly greater fluid flow velocities) at and/or near a distal portion of the guide catheter 206 as compared to, for example, simply activating the pressure source of the RA device 100 by cycling the lever 104 of the RA device 100. These suction forces generated by application of the stored vacuum can be used to not only aspirate the guide catheter 206, but also to aspirate or otherwise remove some or all of the clot material PE remaining in the blood vessel BV after retraction of the interventional device ID.

The method 1000 includes flushing the tubing system 300 (block 1008). In some embodiments, flushing the tubing system 300 includes (i) actuating (e.g., closing) the clamp 410 to inhibit fluid flow from the guide catheter 206 into the tubing system 300, (ii) disconnecting the tubing section 326 of the clot reservoir 306 from the tubing section 302e and the connector 417 of the tubing system 300, (iii) placing the tubing section 326 into a container of fluid (e.g., saline), and (iv) pumping the lever 104 of the RA device 100 to draw the fluid through the tubing system 300. In some embodiments, the housing 322 of the clot reservoir 306 can be temporarily disconnected (e.g., unscrewed) from the cap assembly 330 so that the clot material PE in the clot reservoir 306 can be removed. In certain embodiments, the tubing system 300 need not be flushed prior to a second pass with the interventional device ID or another interventional device. In some embodiments, flushing the tubing system 300 can include attaching a syringe to the fluid connector 332 of the clot reservoir 306 and/or to the tubing section 302a of the tubing system 300 and using the syringe to generate a negative pressure to draw the fluid through the clot reservoir 306.

After the tubing system 300 has been flushed, the method 1000 can return to block 1001. In particular, the same interventional device ID and delivery sheath 204 can be cleaned and subsequently advanced through the guide catheter 206 and to the remaining clot material PE in the blood vessel BV. In some embodiments, a new interventional device and delivery sheath can be used for each pass to reduce the likelihood of contamination (e.g., reintroduction of clot material PE into the patient). Once the desired amount of clot material PE has been removed from the patient, the catheter system 200 may be fully withdrawn from the patient (block 1004).

In one aspect of the present technology, the method 1000 provides for multiple passes of an interventional device without requiring that the entire guide catheter be removed after each pass. Accordingly, the present technology allows for only a single insertion of a guide catheter during a procedure including multiple passes to remove clot material-increasing the speed of the procedure and reducing trauma to the patient since the guide catheter does not need to be reintroduced (e.g., advanced through the vasculature and past the heart) before each pass.

Moreover, in certain embodiments, the present technology can enable the guide catheter 206 to be relocated to an alternate treatment site within the patient without removing the guide catheter 206 from the patient and, therefore, without reintroducing the guide catheter 206 through the heart. For example, the guide catheter 206 can be relocated to another treatment site within the lungs including a treatment site in the opposite lung. More specifically, (i) a dilator can be reintroduced into the guide catheter 206, (ii) the guide catheter 206 can be withdrawn into the main pulmonary artery, (iii) the guidewire can be redirected to the new treatment site, (iv) the guide catheter 206 can be advanced over the guidewire to the new treatment site, and (v) the dilator can be removed.

Additional details of the systems, devices, and methods described above with reference to FIGS. 4-9 are provided in Appendix B to this application.

IV. OTHER SELECTED EMBODIMENTS OF ATTACHMENT/VALVE MEMBERS, AND ASSOCIATED DEVICES AND METHODS OF USE

Figure 11:
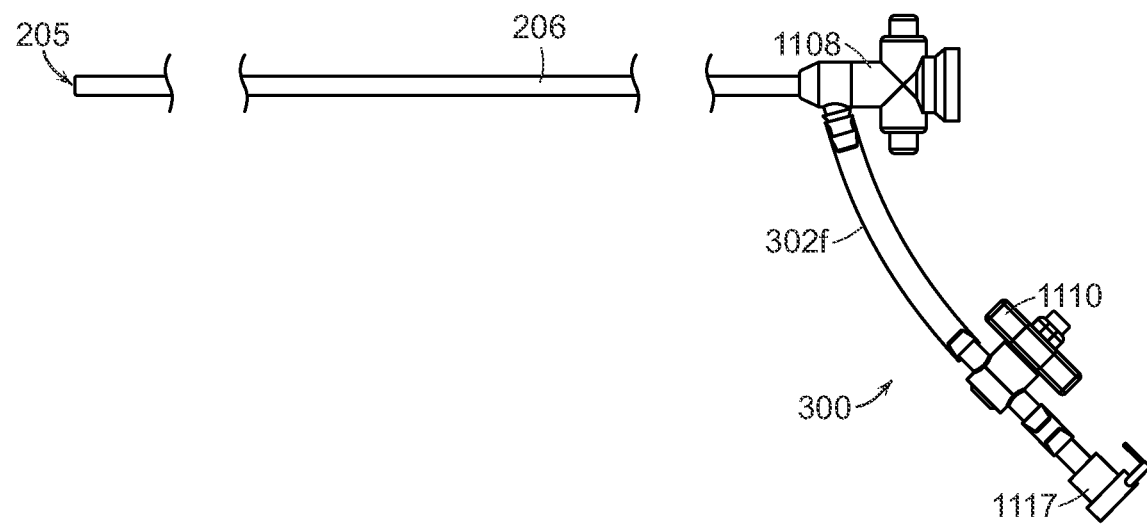
FIG. 11 is a side view of an attachment member and a fluid control unit of the retraction and aspiration system in accordance with embodiments of the present technology.

FIG. 11 is a side view of an attachment/valve member 1108 ("attachment member 1108") of the catheter system 200 and a second fluid control unit 1110 of the tubing system 300 in accordance with embodiments of the present technology. The attachment member 1108 and the second fluid control unit 1110 can have some features generally similar to the features of the attachment members 208, 408 and the second fluid control unit 310, 410, respectively, described above with reference to FIGS. 1A-10. For example, the attachment member 1108 can be integral with or coupled to a proximal portion of the guide catheter 206 and configured to be detachably coupled to the RA device 100 (FIGS. 1A and 1B; e.g., via a snap-fit arrangement) to at least partially secure the catheter system 200 to the RA device 100. When secured to the RA Device 100, the attachment member 1108 can fluidly connect the lumen 205 (e.g., an aspiration lumen) of the guide catheter 206 to the tubing system 300 of the clot retrieval system 1 via the tubing section 302f. Likewise, the second fluid control unit 1110 can be a stopcock ("stopcock 1110") that is externally operable to regulate the flow of fluid through the tubing section 302f.

As further shown in FIG. 11, the tubing system 300 can include a connector 1117 for, for example, fluidly connecting the tubing section 302f and the stopcock 1110 to other portions of the tubing system 300 (e.g., those shown in FIGS. 1A and 1B). In some embodiments, the connector 1117 is a quick-release connector that enables rapid coupling/decoupling of the tubing section 302f and stopcock 1110 to other components of the tubing system 300.

Figure 12:
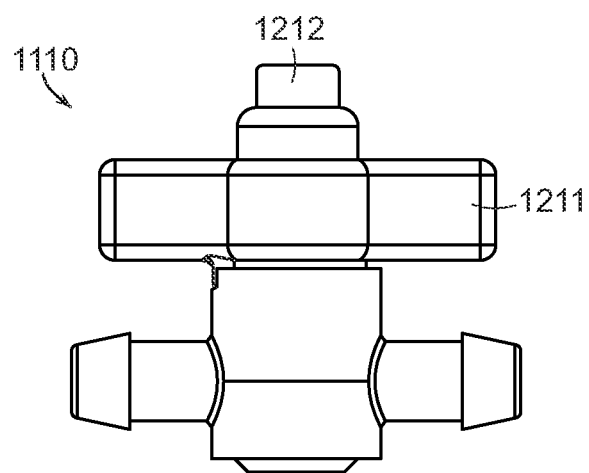
FIG. 12 is a side view of the fluid control unit shown in FIG. 11 in accordance with embodiments of the present technology.

FIG. 12 is a side view of the stopcock 1110 in accordance with embodiments of the present technology. In the embodiment illustrated in FIG. 12, the stopcock 1110 includes a grip member (e.g., a handle, a knob, etc.) 1211 that can be actuated (e.g., twisted by the hand of an operator) to partially or fully restrict fluid flow through the tubing section 302f. In some embodiments, the stopcock 1110 also includes an injection port 1212 (e.g., a needleless injection port) configured to receive a syringe or other fluid delivery member therethrough. In some embodiments, the injection port 1212 permits fluid to be introduced into the attachment member 1108 and the guide catheter 206 without requiring that a connector 1117 be decoupled from the tubing system 300. For example, in some embodiments, an operator can actuate the stopcock 1110 (e.g., twist the grip member 1211) to close the stopcock 1110 and subsequently introduce a syringe at the injection port 1212 to flush the guide catheter 206 with a fluid (e.g., saline) introduced via the syringe.

Figure 13A:
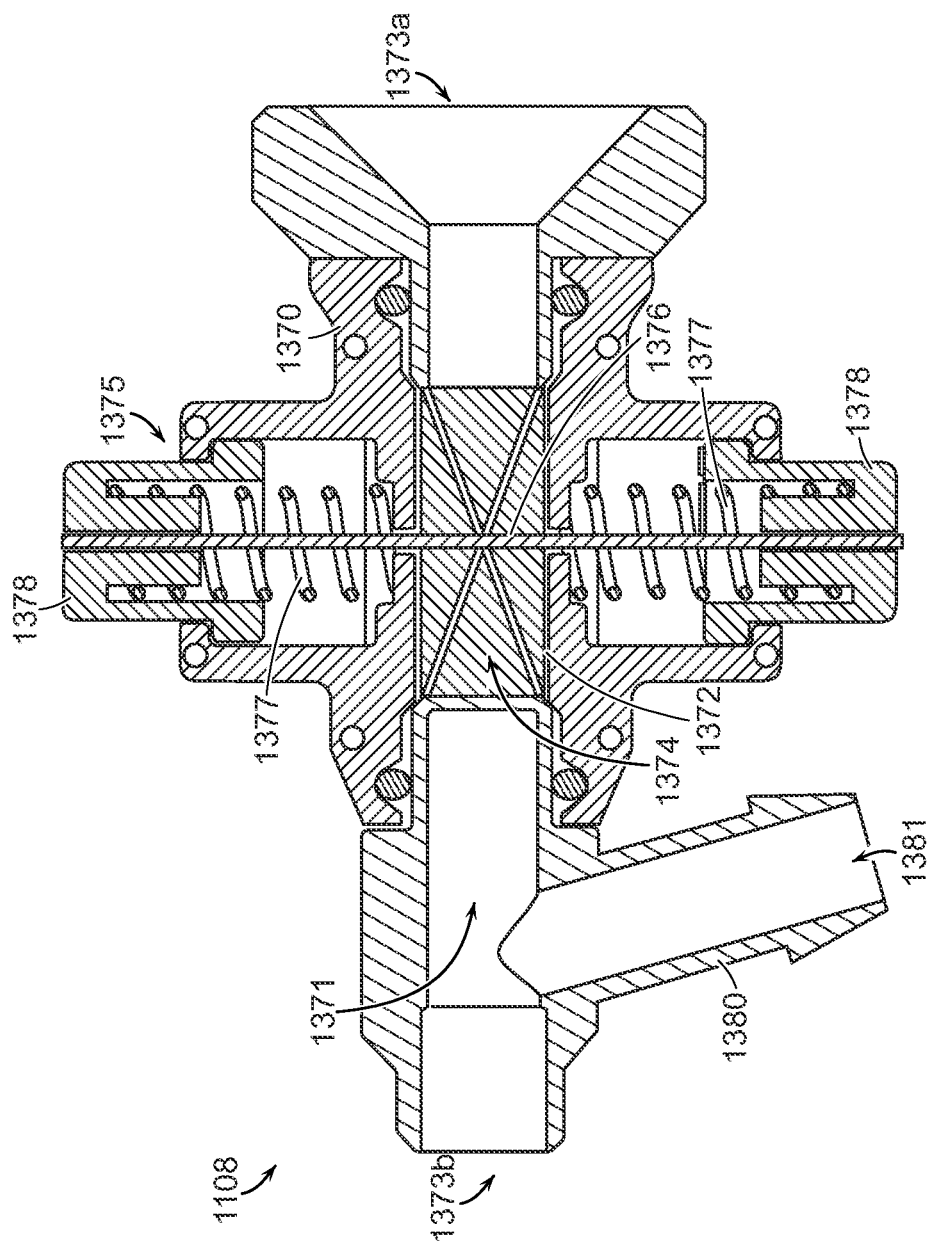
FIGS. 13A and 13B are side cross-sectional views of the attachment member shown in FIG. 11 in a first configuration and a second configuration, respectively, in accordance with embodiments of the present technology.
Figure 13B:
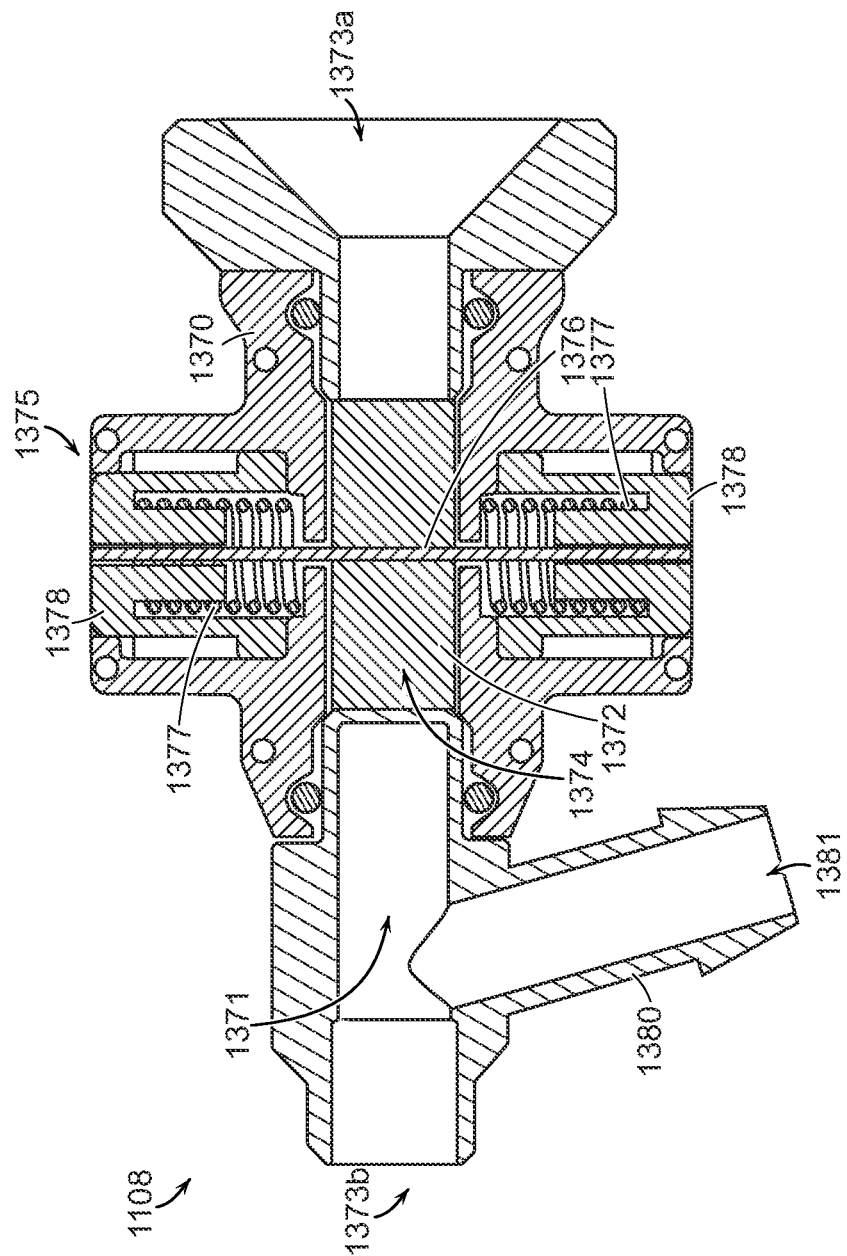

FIGS. 13A and 13B are side cross-sectional views of the attachment member 1108 in a first configuration and a second configuration, respectively, in accordance with embodiments of the present technology. The attachment member 1108 can be, for example, a garrote valve (e.g., a hemostasis valve) as disclosed in provisional U.S. Patent Application No. 62/554,931, filed Sep. 6, 2017, and titled "HEMOSTASIS VALVES AND METHODS OF USE," which is reproduced in Appendix D to this application, and which is incorporated herein by reference in its entirety.

In particular, referring to FIGS. 13A and 13B together, the attachment member 1108 can include a housing 1370 having a proximal opening 1373a and a distal opening 1373b, and defining a first lumen (e.g., an interior channel) 1371 extending between the proximal and distal openings 1373a, 1373b.

The housing 1370 further includes a branch portion 1380 configured to be coupled to the tubing section 302f and defining a second lumen 1381 branching from the first lumen 1371. In some embodiments, the second lumen 1381 can have a relatively large diameter (e.g., between about 0.098 inch and 0.210 inch, about 0.210 inch, greater than 0.210 inch, etc.) to help inhibit clogging and/or collection of clot material within the attachment member 1108 during, for example, aspiration of the guide catheter 206. In one aspect of the present technology, the first lumen 1371 can have a generally constant diameter along its length.

As shown, a tubular member (e.g., an elongate member) 1372 can extend at least partially through the first lumen 1371 to define a central lumen 1374 that is generally coaxial with the first lumen 1371. In some embodiments, the tubular member 1372 can comprise a compliant tubular structure (e.g., a silicon tube) that can be, for example, a thin-walled compliant tubular structure. The thin-walled structure of the tubular member 1372 can facilitate the collapse, and specifically the uniform collapse of the tubular member 1372 and sealing of the tubular member 1372. For example, the attachment member 1108 can further include an actuation mechanism 1375 coupled to the tubular member 1372 and configured to collapse and seal the tubular member 1372 via compression and/or constriction of one or more filaments 1376 coupled to the tubular member 1372.

More specifically, in some embodiments, the actuation mechanism 1375 can be a manual actuator such as one or more buttons 1378. Depression or release of the buttons can, in some embodiments, facilitate sealing of the tubular member 1372 around tools or instruments of a wide range of sizes and/or diameters that fit through the tubular member 1372. For example, FIG. 13A illustrates the attachment member 1108 with the actuation mechanism 1375 in the first configuration in which the tubular member 1372 is in a collapsed and/or sealed state having a minimum diameter (e.g., conformed to a diameter of a portion of a catheter system inserted therethrough). In the embodiment shown in FIG. 13A, the actuation mechanism 1375 is biased (e.g., by one or more springs 1377) to maintain the tubular member 1372 in the collapsed state. Specifically, in the first configuration, the actuation mechanism 1375 can tighten the filament 1376 to constrict or compress the tubular member 1372 to seal the central lumen 1374 of the tubular member 1372. Thus, when the buttons 1378 are not depressed, the attachment member 1108 can provide a hemostatic seal.

As shown in the embodiment of FIG. 13B, the attachment member 1108 is in an expanded (e.g., open) and/or unsealed state having a maximum diameter (e.g., a diameter generally the same as the first lumen 1371). More particularly, one or more of the buttons 1378 may be depressed to, for example, loosen the filament 1376 and allow expansion of the tubular member 1372 to unseal the central lumen 1374 of the tubular member 1372.

Accordingly, the actuation mechanism 1375 and tubular member 1372 of the attachment member 1108 provide for sealing of the attachment member 1108 around, for example, various components of the catheter system 200 (e.g., the delivery sheath 204, the pull member 202, the guidewire, the interventional device ID, etc.) that are inserted through the attachment member 1108 for advancement to the treatment site in the blood vessel BV. Moreover, in the second configuration, the central lumen 1374 of the tubular member 1372 and the first lumen 1371 of the housing 1370 can together provide a continuous lumen of generally constant diameter. As described above, such a constant diameter can prevent clot material PE associated with the interventional device ID from getting stuck in (e.g., remaining in) the attachment member 1108 as the interventional device ID is retracted through the attachment member 1108—thus minimizing the risk of reintroducing clot material to the patient upon a second pass using the interventional device ID (or another interventional device).

Figure 14:
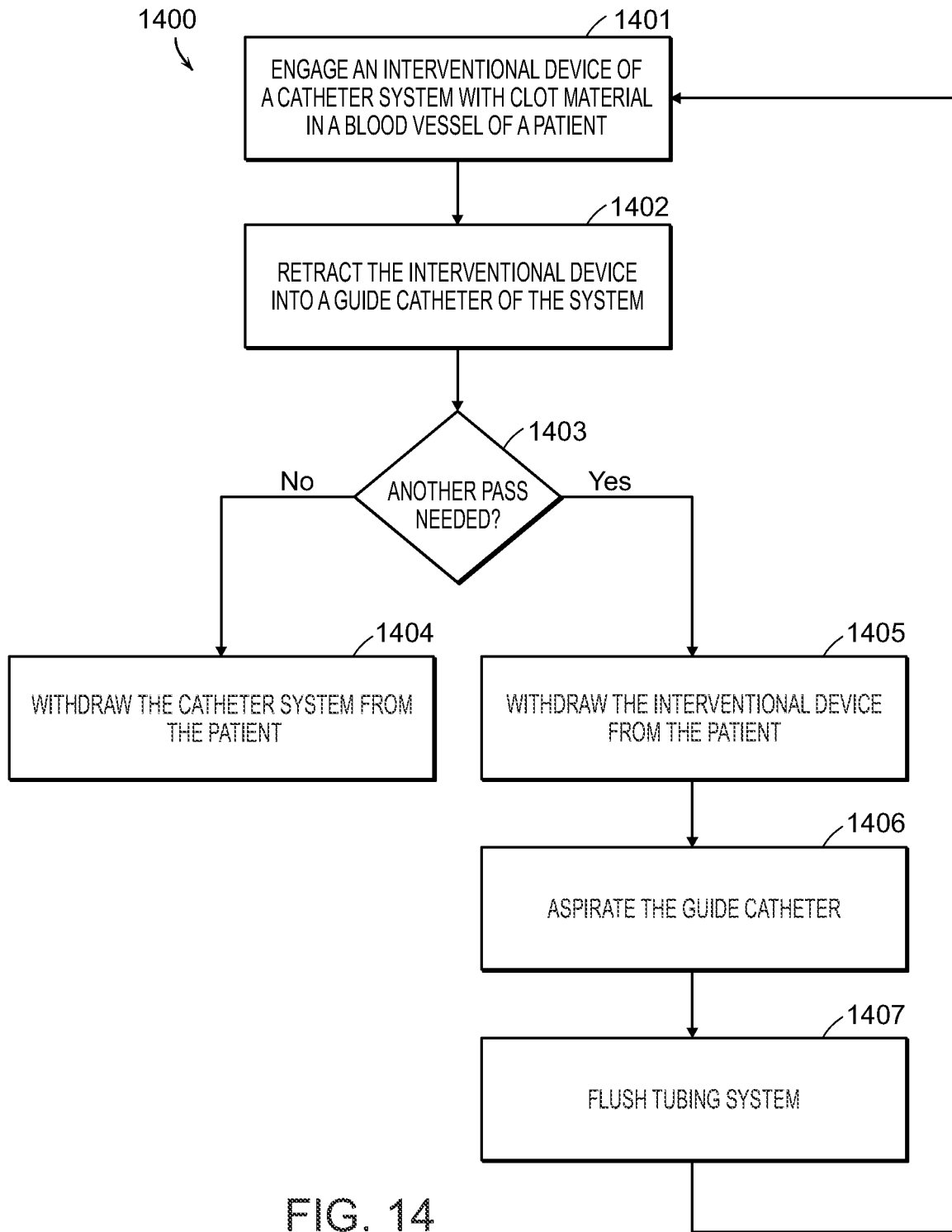
FIG. 14 is a flow diagram of a process or method for operating the retraction and aspiration system in accordance with embodiments of the present technology.

FIG. 14 is a flow diagram of a process or method 1400 for operating the clot retrieval system 1 including the attachment member 1108 to remove clot material from within a blood vessel (e.g., a pulmonary blood vessel) of a human patient in accordance with embodiments of the present technology. Although some features of the method 1400 are described in the context of the embodiments shown in FIGS. 1A, 1B, and 11-13 for sake of illustration, one skilled in the art will readily understand that the method 1400 can be carried out using other suitable systems and/or devices.

The method 1400 includes engaging the interventional device ID of the catheter system 200 with the clot material PE in the blood vessel BV as, for example, described above with reference to FIGS. 2A-2D (block 1401). In particular, the attachment member 1108 of the catheter system 200 can be coupled to the RA device 100, and the interventional device ID can be deployed within at least a portion of the clot material PE by proximally retracting the delivery sheath 204 relative to the interventional device ID.

The method 1400 continues by proximally retracting the interventional device ID and associated clot material PE into the guide catheter 206 of the catheter system 200 until a distal terminus of the clot material PE is proximal from a distal terminus of the guide catheter 206 as, for example, described above with reference to FIGS. 2E-2G (block 1402). In particular, the RA device 100 can be pumped or cycled one or more times (e.g., one time, three times, five times, etc.) to retract the interventional device ID and/or delivery sheath 204 into the guide catheter 206 while simultaneously aspirating the lumen 205 of the guide catheter 206 to remove clot material PE and blood, which are drawn through the attachment member 1108 of the catheter system 200 and into the tubing system 300 (e.g., through the clot reservoir 306 to the reservoir 320).

In some embodiments, the interventional device ID can be retracted proximally into the guide catheter 206 without use of the RA device 100. For example, the operator can manually retract the interventional device ID and associated clot material PE into the guide catheter 206.

After the initial deployment of the interventional device ID in blocks 1401 and 1402, the operator can determine whether it is necessary or desirable to redeploy the interventional device ID within the blood vessel BV of the patient in order to remove additional clot material PE that was not removed during a previous pass with the interventional device ID (block 1403). In some embodiments, the operator can visualize the amount of clot material PE collected in the clot reservoir 306 to at least partially determine whether another pass is needed. In other embodiments, the operator can rely on imaging (e.g., fluoroscopic imaging) of the blood vessel BV or other techniques known in the art to determine whether an additional pass is necessary. If another pass is not needed (e.g., the clot material PE was adequately removed), the operator can elect to withdraw the catheter system 200 from the patient at block 1404. If clot material PE remains in the vessel, the operator can prepare to redeploy the interventional device ID.

To redeploy the interventional device ID, the method 1400 includes withdrawing the interventional device ID from the patient (block 1405). In particular, before withdrawing the interventional device ID, the catheter system 200 can be decoupled from the RA device by (i) decoupling the attachment member 1108 from the distal portion 100b of the RA device 100 and (ii) removing the delivery sheath 204 and/or guidewire from the channel 116 of the RA device 100. Additionally, in some embodiments, the stopcock 1110 can be actuated (e.g., twisted closed) to prevent fluid flow from the guide catheter 206 into the tubing system 300 during withdrawal of the interventional device ID.

The delivery sheath 204 and/or another component of the catheter system 200 may then be manually (e.g., by the operator) or automatically pulled proximally to withdraw the interventional device ID from the patient. Before the interventional device ID and associated clot material PE are withdrawn through the attachment member 1108, the actuation mechanism 1375 of the attachment member 1108 can be actuated (e.g., by depressing the buttons 1378) to move the tubular member 1372 to the second configuration (e.g., to open the tubular member 1372) such that the central lumen 1374 of the tubular member 1372 and the first lumen 1371 of the housing 1370 together provide a continuous lumen of generally constant diameter. Accordingly, the interventional device ID can be fully withdrawn (e.g., retracted proximally) through the attachment member 1108 without causing a significant amount of clot material PE associated with the interventional device ID to remain in the attachment member 1108—thus minimizing the risk of reintroducing clot material to the patient upon an additional pass using the interventional device ID (or another interventional device). Moreover, in certain embodiments, the guidewire of the catheter system 200 is pinned during withdrawal of the interventional device ID and the delivery sheath 204 such that the guidewire does not move relative to the interventional device ID and the delivery sheath 204. Therefore, in such embodiments, the guidewire does not need to be re-advanced to the treatment site prior to an additional pass.

Once the interventional device ID has been fully removed from the guide catheter 206 and the attachment member 1108, the attachment member 1108 can be returned to the first (e.g., sealed) configuration by, for example, releasing the buttons 1378. Next, the method includes aspirating the guide catheter 206 by, for example, pumping or cycling the lever 104 of the RA device 100 one or more times (block 1406). In embodiments where the stopcock 1110 was previously closed (e.g., at block 1405), prior to pumping the lever 104, the stopcock 1110 can be opened to permit fluid flow from the guide catheter 206 into the tubing system 300. Aspirating the guide catheter 206 removes any residual clot material PE remaining in the guide catheter 206. Accordingly, the residual clot material PE is not reintroduced into the blood vessel BV of the patient when the interventional device ID and delivery sheath 204 (or another interventional device ID) are subsequently advanced through the guide catheter 206 during another pass. In certain embodiments, the guide catheter 206 can further be flushed with a fluid (e.g., heparinized saline). For example, the fluid can be introduced through the injection port 1212 while simultaneously pressing the buttons 1378 of the attachment member 1108. In certain embodiments, the stopcock 1110 can be closed (e.g., at block 1406), and a syringe can be connected to the injection port 1212 and used to generate a negative pressure prior to opening the stopcock 1110 to permit fluid flow from the guide catheter 206 into the syringe.

In some embodiments, the guide catheter 206 can be aspirated without use of the RA device 100. For example, a syringe or other pressure source can be fluidly coupled directly to the connector 1117 and used to aspirate the guide catheter 206. In such embodiments, opening of the stopcock 1110 fluidly connects the syringe to the lumen 205 of the guide catheter 206 and closing of the stopcock 1110 fluidly disconnects the syringe from the lumen 205 of the guide catheter 206. In some embodiments, the syringe or other pressure source can be pre-charged with a vacuum-such as by drawing a plunger of the syringe with the stopcock 1110 closed. The stopcock 1110 can then be opened to instantaneously or nearly instantaneously (e.g., immediately) apply the stored vacuum pressure to the tubing system 300 and to the lumen 205 of the guide catheter 206, thereby generating suction throughout the guide catheter 206. In particular, suction can be generated at a distal portion of the guide catheter 206. In one aspect of the present technology, pre-charging or storing the vacuum before applying the vacuum to the lumen 205 of the guide catheter 206 is expected to generate greater suction forces with a faster ramp time (and correspondingly greater fluid flow velocities) at and/or near a distal portion of the guide catheter 206 as compared to, for example, simply activating the pressure source of the RA device 100 by cycling the lever 104 of the RA device 100. These suction forces generated by application of the stored vacuum can be used to not only aspirate the guide catheter 206, but also to aspirate or otherwise remove some or all of the clot material PE remaining in the blood vessel BV after retraction of the interventional device ID.

The method 1400 includes flushing the tubing system 300 (block 1407). In some embodiments, flushing the tubing system 300 includes (i) closing the stopcock 1110 to inhibit fluid flow from the guide catheter 206 into the tubing system 300, (ii) disconnecting the tubing section 326 of the clot reservoir 306 from the tubing section 300e of the tubing system 300, (iii) placing the tubing section 326 into a container of fluid (e.g., saline), and (iv) pumping the lever 104 of the RA device 100 to draw the fluid through the tubing system 300. In some embodiments, the housing 322 of the clot reservoir 306 can be temporarily decoupled (e.g., unscrewed) from the cap assembly 330 so that the clot material PE in the clot reservoir 306 can be removed. In certain embodiments, the tubing system 300 need not be flushed prior to an additional pass with the interventional device ID. In some embodiments, flushing the tubing system 300 can include attaching a syringe to the fluid connector 332 of the clot reservoir 306 and/or to the tubing section 302a of the tubing system 300 and using the syringe to generate a negative pressure to draw the fluid through the clot reservoir 306.

After the tubing system 300 has been flushed, the method 1400 can return to block 1401. In particular, the same interventional device ID and delivery sheath 204 can be cleaned and subsequently advanced through the guide catheter 206 and to the remaining clot material PE in the blood vessel. In some embodiments, a new interventional device ID and delivery sheath 204 can be used for each pass to reduce the likelihood of contamination (e.g., reintroduction of clot material PE). Once the desired amount of clot material PE has been removed from the patient, the catheter system 200 may be fully withdrawn from the patient (block 1404).

In one aspect of the present technology, the method 1400 provides for multiple passes of an interventional device without requiring that the entire guide catheter be removed after each pass. Accordingly, the present technology allows for only a single insertion of a guide catheter during a procedure including multiple passes to remove clot material-increasing the speed of the procedure and reducing trauma to the patient since the guide catheter does not need to be reintroduced (e.g., advanced through the vasculature and past the heart) before each pass.

Moreover, in certain embodiments, the present technology can enable the guide catheter 206 to be relocated to an alternate treatment site within the patient without removing the guide catheter 206 from the patient and, therefore, without reintroducing the guide catheter 206 through the heart. For example, the guide catheter 206 can be relocated to another treatment site within the lungs including a treatment site in the opposite lung. More specifically, (i) a dilator can be reintroduced into the guide catheter 206, (ii) the guide catheter 206 can be withdrawn into the main pulmonary artery, (iii) the guidewire can be redirected to the new treatment site, (iv) the guide catheter 206 can be advanced over the guidewire to the new treatment site, and (v) the dilator can be removed.

Additional details of the systems, devices, and methods described above with reference to FIGS. 11-14 are provided in Appendix C to this application.

V. EXAMPLES

1. A method for the intravascular treatment of clot material from a treatment site within a blood vessel of a human patient, the method comprising:
    engaging a first interventional device with the clot material at the treatment site in the blood vessel;
    retracting the first interventional device and a portion of the clot material into a distal portion of an elongated shaft;
    inserting a first valve insert into an attachment member coupled to a proximal portion of the elongated shaft;
    withdrawing the first interventional device and the portion of the clot material proximally through (a) the elongated shaft, (b) the attachment member, and (c) the first valve insert;
    inserting a second valve insert into the attachment member instead of the first valve insert; aspirating the elongated shaft; and
    advancing a second interventional device distally through the elongated shaft to the treatment site.

2. The method of example 1 wherein, after inserting the first valve insert into the attachment member, the first valve insert and the attachment member together define a lumen having a generally constant diameter.

3. The method of example 2 wherein the diameter of the lumen is generally the same as the diameter of the elongated shaft.

4. The method of any one of examples 1-3 wherein inserting the first valve insert into the attachment member includes exercising a valve of the attachment member.

5. The method of any one of examples 1-4, further comprising actuating the second valve insert to seal the attachment member.

6. The method of any one of examples 1-5 wherein the first interventional device and the second interventional device are the same interventional device, and wherein the method further comprises cleaning the interventional device to remove the portion of the clot material.

7. The method of any one of examples 1-6, further comprising engaging the second interventional device with remaining clot material at the treatment site in the blood vessel.

8. The method of any one of examples 1-7 wherein aspirating the elongated shaft includes aspirating, into the elongated shaft, at least a portion of clot material remaining at the treatment site in the blood vessel.

9. The method of example 8 wherein aspirating the elongated shaft includes
coupling a syringe to the elongated shaft via a fluid control unit, wherein opening of the fluid control unit fluidly connects the syringe to the elongated shaft, and wherein closing of the fluid control device fluidly disconnects the syringe from the elongated shaft;
drawing a plunger of the syringe to generate a vacuum while the fluid control unit is closed; and
opening the fluid control unit to apply the vacuum to the elongated shaft to thereby aspirate the portion of the remaining clot material into the elongated shaft.

10. The method of example 9 wherein the fluid control unit is a clamp.

11. A method for the intravascular treatment of clot material from a treatment site within a blood vessel of a human patient, the method comprising:
engaging a first interventional device with the clot material at the treatment site in the blood vessel;
retracting the first interventional device and a portion of the clot material into a distal portion of an elongated shaft;
withdrawing the interventional device and the portion of the clot material from the blood vessel through the elongated shaft and an attachment member coupled thereto, including—
before withdrawing the interventional device through the attachment member, actuating the attachment member to move the attachment member from a first configuration in which a lumen of the attachment member is sealed to a second configuration in which the lumen of the attachment member is open;
after withdrawing the interventional device through the attachment member, actuating the attachment member to return the attachment member to the first configuration from the second configuration;
aspirating the elongated shaft; and
advancing a second interventional device distally through the elongated shaft to the treatment site.

12. The method of example 11 wherein actuating the attachment member includes pressing one or more buttons on the attachment member.

13. The method of example 11 or 12 wherein in the second configuration, the lumen of the attachment member has a generally constant diameter.

14. The method of example 13 wherein the diameter of the lumen is generally the same as a diameter of the elongated shaft.

15. The method of any one of examples 11-14 wherein the first interventional device and the second interventional device are the same interventional device, and wherein the method further comprises cleaning the interventional device to remove the portion of the clot material.

16. The method of any one of examples 11-15, further comprising engaging the second interventional device with remaining clot material in the blood vessel.

17. The method of one of examples 11-16 wherein aspirating the elongated shaft includes—
coupling a syringe to the elongated shaft via a stopcock, wherein opening of the stopcock fluidly connects the syringe to the elongated shaft, and wherein closing of the stopcock fluidly disconnects the syringe from the elongated shaft;
drawing a plunger of the syringe to generate a vacuum while the stopcock is closed; and
opening the stopcock to apply the vacuum to the elongated shaft to thereby aspirate, into the elongated shaft, at least a portion of clot material remaining at the treatment site in the blood vessel.

18. A method for the intravascular treatment of clot material from a treatment site within a blood vessel of a human patient, the method comprising:
engaging an interventional device with the clot material at the treatment site in the blood vessel;
retracting the interventional device and a portion of the clot material into a distal portion of a lumen of an elongated shaft;
unsealing an attachment member coupled to a proximal portion of the elongated shaft;
withdrawing the interventional device and the portion of the clot material through the lumen of the elongated shaft and through the attachment member;
sealing the attachment member;
aspirating the elongated shaft; and
advancing the same or a different interventional device distally through the lumen of the elongated shaft to the treatment site.

19. The method of example 18 wherein unsealing the attachment member includes exercising a valve of the attachment member such that a lumen of the attachment member has a diameter that is about equal to a diameter of the lumen of the elongated shaft.

20. The method of example 18 or 19, further comprising:
engaging the same or the different interventional device with clot material remaining in the blood vessel; and
retracting the same or the different interventional device interventional device and a portion of the remaining clot material into the distal portion of the lumen of the elongated shaft;
unsealing the attachment member; and withdrawing the same or the different interventional device and the portion of the remaining clot material through the lumen of the elongated shaft and through the attachment member.

VI. CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A clot collection reservoir, comprising:
  a housing defining a sealed chamber and having a first housing end portion and a second housing end portion opposite the first housing end portion;
  a first port configured to be fluidly coupled to an aspiration catheter, wherein the first port is positioned proximate to the first housing end portion and provides a first fluid path to the chamber;
  a second port configured to be fluidly coupled to an aspiration source, wherein the second port provides a second fluid path from the chamber; and
  a filter removably positioned within the chamber, wherein the filter has a substantially cylindrical shape extending from a first filter end portion to a second filter end portion, and wherein the filter extends continuously about the first filter end portion such that the filter encloses an interior region around the second port;
  wherein the aspiration source is configured to generate negative pressure in the chamber via the second port to (a) draw blood and clot material from the aspiration catheter through the first port into the chamber and (b) draw blood through the filter into the interior region and through the second port;
  wherein the filter is configured to inhibit the clot material from passing through the filter into the interior region and through the second port; and
  wherein the housing is at least partially transparent to permit visualization of the clot material in the chamber outside the interior region.

2. The clot collection reservoir of claim 1 wherein the second port is positioned proximate to the second housing end portion.

3. The clot collection reservoir of claim 1, further comprising a cap configured to be releasably coupled to the second housing end portion, wherein the cap is removable from the housing to provide access to the filter.

4. The clot collection reservoir of claim 1 wherein the first filter end portion is curved.

5. The clot collection reservoir of claim 1 wherein the source of aspiration is configured to generate the negative pressure in the chamber via the second port to draw the clot material against the first filter end portion.

6. The clot collection reservoir of claim 1 wherein the housing is entirely transparent, and wherein the first port is integrally formed with the housing.

7. The clot collection reservoir of claim 1 wherein the first filter end portion is positioned closer to the first housing end portion than the second filter end portion, and wherein the second filter end portion is positioned closer to the second housing end portion than the first filter end portion.

8. A clot collection reservoir, comprising:
  a housing defining a sealed chamber and having a first housing end portion and a second housing end portion opposite the first housing end portion;
  a first port configured to be fluidly coupled to an aspiration catheter, wherein the first port is positioned proximate to the first housing end portion and provides a first fluid path to the chamber;
  a second port configured to be fluidly coupled to an aspiration source, wherein the second port provides a second fluid path from the chamber;
  a cap configured to be releasably coupled to the second housing end portion; and
  a filter coupled to the cap and configured to be positioned when the chamber when the cap is releasably coupled to the second housing end portion, wherein the filter has a substantially cylindrical shape extending from a first filter end portion to a second filter end portion, and wherein the filter extends continuously about the first filter end portion such that the filter encloses an interior region around the second port;
  wherein the aspiration source is configured to generate negative pressure in the chamber via the second port to (a) draw blood and clot material from the aspiration catheter through the first port into the chamber and (b) draw blood through the filter into the interior region and through the second port;
  wherein the filter is configured to inhibit the clot material from passing through the filter into the interior region and through the second port;
  wherein the housing is at least partially transparent to permit visualization of the clot material in the chamber outside the interior region; and
  wherein the cap is removable from the housing to provide access to the filter.

9. A clot collection reservoir, comprising:
  a housing defining a sealed chamber and having a first housing end portion and a second housing end portion opposite the first housing end portion;
  a first port configured to be fluidly coupled to an aspiration catheter, wherein the first port is positioned proximate to the first housing end portion and provides a first fluid path to the chamber;
  a second port configured to be fluidly coupled to an aspiration source, wherein the second port provides a second fluid path from the chamber;
  a cap configured to be releasably coupled to the second housing end portion; and
  a filter positioned within the chamber, wherein the filter has a substantially cylindrical shape extending from a first filter end portion to a second filter end portion, and wherein the filter extends continuously about the first filter end portion such that the filter encloses an interior region around the second port;
  wherein the aspiration source is configured to generate negative pressure in the chamber via the second port to (a) draw blood and clot material from the aspiration catheter through the first port into the chamber and (b) draw blood through the filter into the interior region and through the second port;
  wherein the filter is configured to inhibit the clot material from passing through the filter into the interior region and through the second port;
  wherein the housing is at least partially transparent to permit visualization of the clot material in the chamber outside the interior region; and
  wherein the cap and the filter are removable from the housing to provide access to the clot material within the chamber.

10. A clot treatment system, comprising:
an aspiration catheter configured to be intravascularly positioned proximate to clot material within a blood vessel of a patient;
an aspiration source; and
a clot collection reservoir, comprising—
a housing defining a sealed chamber and having a first housing end portion and a second housing end portion opposite the first housing end portion;
a first port configured to be fluidly coupled to the aspiration catheter, wherein the first port is positioned proximate to the first housing end portion and provides a first fluid path to the chamber;
a second port configured to be fluidly coupled to the aspiration source, wherein the second port provides a second fluid path to the chamber; and
a filter positioned within the chamber, wherein the filter has a substantially cylindrical shape extending from a first filter end portion to a second filter end portion, and wherein the filter extends continuously about the first filter end portion such that the filter encloses an interior region around the second port;
wherein the aspiration source is configured to generate negative pressure in the chamber via the second port to (a) draw blood and clot material from the aspiration catheter through the first port into the chamber and (b) draw blood through the filter into the interior region and through the second port;
wherein the filter is configured to inhibit the clot material from passing through the filter into the interior region and through the second port; and
wherein the filter is removably positioned within the chamber to provide access to the clot material within the chamber.

11. The clot treatment system of claim 10 wherein the housing is at least partially transparent to permit visualization of the clot material in the chamber outside the interior region.

12. The clot treatment system of claim 10 wherein the second port is positioned proximate to the second housing end portion.

13. The clot treatment system of claim 10 wherein the clot collection reservoir is spaced apart from the aspiration source, and further comprising at least one tube fluidly coupling the second port to the aspiration source.

14. A clot treatment system, comprising:
an aspiration catheter configured to be intravascularly positioned proximate to clot material within a blood vessel of a patient;
an aspiration source; and
a clot collection reservoir, comprising—
a housing defining a sealed chamber and having a first housing end portion and a second housing end portion opposite the first housing end portion;
a first port configured to be fluidly coupled to the aspiration catheter, wherein the first port is positioned proximate to the first housing end portion and provides a first fluid path to the chamber;
a second port configured to be fluidly coupled to the aspiration source, wherein the second port provides a second fluid path to the chamber;
a cap configured to be releasably coupled to the second housing end portion; and
a filter positioned within the chamber, wherein the filter has a substantially cylindrical shape extending from a first filter end portion to a second filter end portion, and wherein the filter extends continuously about the first filter end portion such that the filter encloses an interior region around the second port;
wherein the aspiration source is configured to generate negative pressure in the chamber via the second port to (a) draw blood and clot material from the aspiration catheter through the first port into the chamber and (b) draw blood through the filter into the interior region and through the second port;
wherein the filter is configured to inhibit the clot material from passing through the filter into the interior region and through the second port; and
wherein the cap and the filter are removable from the housing to provide access to the clot material within the chamber.

15. A clot treatment system, comprising:
an aspiration catheter configured to be intravascularly positioned proximate to clot material within a blood vessel of a patient;
an aspiration source;
a clot collection reservoir, comprising—
a housing defining a sealed chamber and having a first housing end portion and a second housing end portion opposite the first housing end portion;
a first port configured to be fluidly coupled to the aspiration catheter, wherein the first port is positioned proximate to the first housing end portion and provides a first fluid path to the chamber;
a second port configured to be fluidly coupled to the aspiration source, wherein the second port provides a second fluid path to the chamber; and
a filter positioned within the chamber, wherein the filter has a substantially cylindrical shape extending from a first filter end portion to a second filter end portion, and wherein the filter extends continuously about the first filter end portion such that the filter encloses an interior region around the second port; and
a valve positioned between the clot collection reservoir and the aspiration catheter, wherein the valve is user-actuatable to move between (a) an open position in which the first port is fluidly connected to the aspiration catheter and (b) a closed position in which the first port is fluidly disconnected from the aspiration catheter;
wherein the aspiration source is configured to generate negative pressure in the chamber via the second port to (a) draw blood and clot material from the aspiration catheter through the first port into the chamber and (b) draw blood through the filter into the interior region and through the second port; and
wherein the filter is configured to inhibit the clot material from passing through the filter into the interior region and through the second port.

16. The clot treatment system of claim 15 wherein the aspiration source is configured to generate the negative pressure in the chamber with the valve in the closed position, and wherein the valve is configured to be moved to the open position to apply the negative pressure to the aspiration catheter.

17. A clot treatment system, comprising:
an aspiration catheter configured to be intravascularly positioned proximate to clot material within a blood vessel of a patient;
a hemostasis valve coupled to a proximal portion of the aspiration catheter;
at least one tube fluidly coupling the first port to a portion of the aspiration catheter distal of the hemostasis valve;

an aspiration source; and
a clot collection reservoir, comprising—
  a housing defining a chamber and having a first housing end portion and a second housing end portion opposite the first housing end portion;
  a first port configured to be fluidly coupled to the aspiration catheter, wherein the first port is positioned proximate to the first housing end portion;
  a second port configured to be fluidly coupled to the aspiration source; and
  a filter positioned within the chamber, wherein the filter has a substantially cylindrical shape extending from a first filter end portion to a second filter end portion, and wherein the filter extends continuously about the first filter end portion such that the filter encloses an interior region around the second port;
wherein the aspiration source is configured to generate negative pressure in the chamber via the second port to (a) draw blood and clot material from the aspiration catheter through the first port into the chamber and (b) draw blood through the filter into the interior region and through the second port; and
wherein the filter is configured to inhibit the clot material from passing through the filter into the interior region and through the second port.

18. The clot treatment system of claim 17 wherein the hemostasis valve comprises:
  a tubular member;
  a button; and
  a filament coupled to the button and the tubular member, wherein the button is actuatable to loosen the filament to unseal the hemostasis valve.

19. The clot treatment system of claim 17 wherein the aspiration source is fluidly couplable to the at least one tube.

20. The clot treatment system of claim 17 wherein the hemostasis valve is configured to receive an instrument therethrough.

21. The clot treatment system of claim 17 wherein the hemostasis valve and the aspiration catheter are configured to receive and route an instrument therethrough.

22. The clot treatment system of claim 17 wherein the hemostasis valve comprises:
  a tubular member defining a lumen;
  a first filament extending in a first loop around the tubular member;
  a second filament extending in a second loop around the tubular member; and
  a pair of actuators biased to circumferentially constrict the first loop and the second loop to elastically deform the tubular member to a first position in which the lumen is constricted, wherein at least one the actuators is movable to decrease a level of tension in the first filament and a level of tension in the second filament to permit the tubular member to expand against the first loop and the second loop to a second position in which the lumen of the tubular member is at least partially open.

23. The clot treatment system of claim 22 wherein the actuators each comprise a button.

24. The clot treatment system of claim 22 wherein the first filament includes a first portion operably coupled to a first one of the actuators and a second portion operably coupled to a second one of the actuators, and wherein the second filament includes a first portion operably coupled to the first one of the actuators and a second portion operably coupled to the second one of the actuators.

25. The clot treatment system of claim 22 wherein the first filament is flexible, and wherein the second filament is flexible.

26. The clot treatment system of claim 17 wherein the aspiration catheter has a size of at least 16 French.

27. The clot treatment system of claim 17 wherein the aspiration catheter has a size of at least 20 French.

28. The clot treatment system of claim 17 wherein the aspiration catheter has a size of at least 22 French.

\* \* \* \* \*